(12) United States Patent
Ketai et al.

(10) Patent No.: US 10,667,911 B2
(45) Date of Patent: Jun. 2, 2020

(54) METHODS, SYSTEMS AND DEVICES FOR CARDIAC VALVE REPAIR

(71) Applicant: EVALVE, INC., Santa Clara, CA (US)

(72) Inventors: Ted Ketai, San Francisco, CA (US); Chris Bender, Oakland, CA (US); Steven A. Tyler, Portola Valley, CA (US); Troy L. Thornton, San Francisco, CA (US); Eric A. Goldfarb, Belmont, CA (US)

(73) Assignee: EVALVE, INC., Santa Clara, CA (US)

( * ) Notice: Subject to any disclaimer, the term of this patent is extended or adjusted under 35 U.S.C. 154(b) by 0 days.

(21) Appl. No.: 15/943,758

(22) Filed: Apr. 3, 2018

(65) Prior Publication Data

US 2018/0250132 A1    Sep. 6, 2018

Related U.S. Application Data

(60) Division of application No. 15/082,137, filed on Mar. 28, 2016, now abandoned, which is a division of
(Continued)

(51) Int. Cl.
*A61F 2/24* (2006.01)
*A61B 17/00* (2006.01)
(Continued)

(52) U.S. Cl.
CPC ...... *A61F 2/2457* (2013.01); *A61B 17/00234* (2013.01); *A61B 17/0401* (2013.01);
(Continued)

(58) Field of Classification Search
CPC .................................................. A61F 2/2457
See application file for complete search history.

(56) References Cited

U.S. PATENT DOCUMENTS 2,097,018 A   10/1937   Chamberlain
2,108,206 A   2/1938    Meeker
(Continued)

FOREIGN PATENT DOCUMENTS

EP   0 179 562 B1   7/1989
EP   0 558 031      9/1993
(Continued)

OTHER PUBLICATIONS

Abe et al., "De Vega's annuloplasty for acquired tricuspid disease: Early and late results in 110 patients" Ann. Thorac. Surg. (Nov. 1989) 48:670-676.
(Continued)

*Primary Examiner* — Andrew M Iwamaye
(74) *Attorney, Agent, or Firm* — Baker Botts L.L.P.

(57) ABSTRACT

Disclosed are methods, systems, and devices for the endovascular repair of cardiac valves, particularly the atrioventricular valves which inhibit back flow of blood from a heart ventricle during contraction. The procedures described herein can be performed with interventional tools, guides and supporting catheters and other equipment introduced to the heart chambers from the patient's arterial or venous vasculature remote from the heart. The interventional tools and other equipment may be introduced percutaneously or may be introduced via a surgical cut down, and then advanced from the remote access site through the vasculature until they reach the heart.

6 Claims, 49 Drawing Sheets

Related U.S. Application Data application No. 13/852,459, filed on Mar. 28, 2013, now abandoned, which is a division of application No. 12/883,095, filed on Sep. 15, 2010, now abandoned, and a continuation-in-part of application No. 11/349,742, filed on Feb. 7, 2006, now abandoned.

(60) Provisional application No. 61/243,459, filed on Sep. 17, 2009, provisional application No. 60/692,802, filed on Jun. 21, 2005, provisional application No. 60/650,918, filed on Feb. 7, 2005.

(51) Int. Cl.
*A61B 17/04* (2006.01)
*A61B 17/29* (2006.01)

(52) U.S. Cl.
CPC ............ *A61F 2/246* (2013.01); *A61F 2/2412* (2013.01); *A61F 2/2454* (2013.01); *A61F 2/2463* (2013.01); *A61F 2/2478* (2013.01); *A61F 2/2487* (2013.01); *A61B 17/0487* (2013.01); *A61B 17/29* (2013.01); *A61B 2017/00243* (2013.01); *A61B 2017/00783* (2013.01); *A61B 2017/00876* (2013.01); *A61B 2017/0409* (2013.01); *A61B 2017/0412* (2013.01); *A61B 2017/0414* (2013.01); *A61B 2017/0417* (2013.01); *A61B 2017/0427* (2013.01); *A61B 2017/0435* (2013.01); *A61B 2017/0445* (2013.01); *A61B 2017/0454* (2013.01); *A61B 2017/0464* (2013.01); *A61B 2017/0496* (2013.01); *A61F 2/2445* (2013.01); *A61F 2210/009* (2013.01); *A61F 2220/0016* (2013.01)

(56) References Cited

U.S. PATENT DOCUMENTS

| | | |
|---|---|---|
| 3,378,010 A | 4/1968 | Codling |
| 3,671,979 A | 6/1972 | Moulopouslos |
| 3,874,388 A | 4/1975 | King et al. |
| 4,056,854 A | 11/1977 | Boretos et al. |
| 4,064,881 A | 12/1977 | Meredith |
| 4,112,951 A | 9/1978 | Hulka et al. |
| 4,297,749 A | 11/1981 | Davis et al. |
| 4,484,579 A | 11/1984 | Meno et al. |
| 4,498,476 A | 2/1985 | Cerwin et al. |
| 4,510,934 A | 4/1985 | Batra |
| 4,809,695 A | 3/1989 | Gwathmey et al. |
| 4,917,089 A | 4/1990 | Sideris |
| 4,944,295 A | 7/1990 | Gwathmey et al. |
| 4,994,077 A | 2/1991 | Dobben |
| 5,015,249 A | 5/1991 | Nakao et al. |
| 5,042,707 A | 8/1991 | Taheri |
| 5,047,041 A | 9/1991 | Samuels |
| 5,049,153 A | 9/1991 | Nakao et al. |
| 5,061,277 A | 10/1991 | Carpentier et al. |
| 5,069,679 A | 12/1991 | Taheri |
| 5,108,368 A | 4/1992 | Hammerslag et al. |
| 5,125,758 A | 6/1992 | DeWan |
| 5,171,252 A | 12/1992 | Friedland |
| 5,190,554 A | 3/1993 | Coddington et al. |
| 5,195,968 A | 3/1993 | Lundquist et al. |
| 5,209,756 A | 5/1993 | Seedhom et al. |
| 5,226,429 A | 7/1993 | Kuzmak |
| 5,226,911 A | 7/1993 | Chee et al. |
| 5,234,437 A | 8/1993 | Sepetka |
| 5,250,071 A | 10/1993 | Palermo |
| 5,254,130 A | 10/1993 | Poncet et al. |
| 5,261,916 A | 11/1993 | Engelson |
| 5,275,578 A | 1/1994 | Adams |
| 5,312,415 A | 5/1994 | Palermo |
| 5,314,424 A | 5/1994 | Nicholas |
| 5,318,525 A | 6/1994 | West et al. |
| 5,325,845 A | 7/1994 | Adair |
| 5,332,402 A | 7/1994 | Teitelbaum |
| 5,350,397 A | 9/1994 | Palermo et al. |
| 5,359,994 A | 11/1994 | Kreuter et al. |
| 5,368,564 A | 11/1994 | Savage |
| 5,368,601 A | 11/1994 | Sauer et al. |
| 5,383,886 A | 1/1995 | Kensey et al. |
| 5,403,312 A | 4/1995 | Yates et al. |
| 5,403,326 A | 4/1995 | Harrison et al. |
| 5,411,552 A | 5/1995 | Andersen et al. |
| 5,417,699 A | 5/1995 | Klein et al. |
| 5,417,700 A | 5/1995 | Egan |
| 5,423,858 A | 6/1995 | Bolanos et al. |
| 5,423,882 A | 6/1995 | Jackman et al. |
| 5,431,666 A | 7/1995 | Sauer et al. |
| 5,437,681 A | 8/1995 | Meade et al. |
| 5,450,860 A | 9/1995 | O'Connor |
| 5,456,684 A | 10/1995 | Schmidt et al. |
| 5,462,527 A | 10/1995 | Stevens-Wright et al. |
| 5,472,044 A | 12/1995 | Hall et al. |
| 5,476,470 A | 12/1995 | Fitzgibbons, Jr. |
| 5,478,309 A | 12/1995 | Sweezer et al. |
| 5,478,353 A | 12/1995 | Yoon |
| 5,487,746 A | 1/1996 | Yu et al. |
| 5,507,725 A | 4/1996 | Savage et al. |
| 5,507,757 A | 4/1996 | Sauer et al. |
| 5,520,701 A | 5/1996 | Lerch |
| 5,522,873 A | 6/1996 | Jackman et al. |
| 5,527,313 A | 6/1996 | Scott et al. |
| 5,527,322 A | 6/1996 | Klein et al. |
| 5,536,251 A | 7/1996 | Evard et al. |
| 5,540,705 A | 7/1996 | Meade et al. |
| 5,542,949 A | 8/1996 | Yoon |
| 5,554,185 A | 9/1996 | Block et al. |
| 5,562,678 A | 10/1996 | Booker |
| 5,571,085 A | 11/1996 | Accisano, III |
| 5,571,137 A | 11/1996 | Marlow et al. |
| 5,571,215 A | 11/1996 | Sterman et al. |
| 5,582,611 A | 12/1996 | Tsuruta et al. |
| 5,593,424 A | 1/1997 | Northrup, III |
| 5,593,435 A | 1/1997 | Carpentier et al. |
| 5,609,598 A | 3/1997 | Laufer et al. |
| 5,618,306 A | 4/1997 | Roth et al. |
| 5,620,452 A | 4/1997 | Yoon |
| 5,626,588 A | 5/1997 | Sauer et al. |
| 5,634,932 A | 6/1997 | Schmidt |
| 5,636,634 A | 6/1997 | Kordis et al. |
| 5,640,955 A | 6/1997 | Ockuly et al. |
| 5,649,937 A | 7/1997 | Bito et al. |
| 5,669,917 A | 9/1997 | Sauer et al. |
| 5,690,671 A | 11/1997 | McGurk et al. |
| 5,706,824 A | 1/1998 | Whittier |
| 5,713,910 A | 2/1998 | Gordon et al. |
| 5,715,817 A | 2/1998 | Stevens-Wright et al. |
| 5,716,367 A | 2/1998 | Koike et al. |
| 5,718,725 A | 2/1998 | Sterman et al. |
| 5,722,421 A | 3/1998 | Francese et al. |
| 5,741,280 A | 4/1998 | Fleenor |
| 5,769,812 A | 6/1998 | Stevens et al. |
| 5,769,863 A | 6/1998 | Garrison |
| 5,772,578 A | 6/1998 | Heimberger et al. |
| 5,782,845 A | 7/1998 | Shewchuk |
| 5,797,927 A | 8/1998 | Yoon |
| 5,797,960 A | 8/1998 | Stevens et al. |
| 5,810,847 A | 9/1998 | Laufer et al. |
| 5,810,876 A | 9/1998 | Kelleher |
| 5,814,029 A | 9/1998 | Hassett |
| 5,820,592 A | 10/1998 | Hammerslag |
| 5,820,631 A | 10/1998 | Nobles |
| 5,823,956 A | 10/1998 | Roth et al. |
| 5,824,065 A | 10/1998 | Gross |
| 5,827,237 A | 10/1998 | Macoviak et al. |
| 5,829,447 A | 11/1998 | Stevens et al. |
| 5,833,671 A | 11/1998 | Macoviak et al. |
| 5,836,955 A | 11/1998 | Buelna et al. |
| 5,840,081 A | 11/1998 | Andersen et al. |
| 5,843,031 A | 12/1998 | Hermann et al. |
| 5,855,614 A | 1/1999 | Stevens et al. |

(56) References Cited

U.S. PATENT DOCUMENTS

| | | |
|---|---|---|
| 5,860,990 A | 1/1999 | Nobles et al. |
| 5,868,733 A | 2/1999 | Ockuly et al. |
| 5,879,307 A | 3/1999 | Chio et al. |
| 5,885,271 A | 3/1999 | Hamilton et al. |
| 5,891,160 A | 4/1999 | Williamson, IV et al. |
| 5,916,147 A | 6/1999 | Boury |
| 5,928,224 A | 7/1999 | Laufer |
| 5,947,363 A | 9/1999 | Bolduc et al. |
| 5,954,732 A | 9/1999 | Hart et al. |
| 5,972,030 A | 10/1999 | Garrison et al. |
| 5,980,455 A | 11/1999 | Daniel et al. |
| 5,989,284 A | 11/1999 | Laufer |
| 6,019,722 A | 2/2000 | Spence et al. |
| 6,033,378 A | 3/2000 | Lundquist et al. |
| 6,036,699 A | 3/2000 | Andreas et al. |
| 6,045,497 A | 4/2000 | Schweich, Jr. et al. |
| 6,060,628 A | 5/2000 | Aoyama et al. |
| 6,060,629 A | 5/2000 | Pham et al. |
| 6,066,146 A | 5/2000 | Carroll et al. |
| 6,077,214 A | 6/2000 | Mortier et al. |
| 6,086,600 A | 7/2000 | Kortenbach |
| 6,117,144 A | 9/2000 | Nobles et al. |
| 6,123,699 A | 9/2000 | Webster, Jr. |
| 6,132,447 A | 10/2000 | Dorsey |
| 6,136,010 A | 10/2000 | Modesitt et al. |
| 6,143,024 A | 11/2000 | Campbell et al. |
| 6,162,233 A | 12/2000 | Williamson, IV et al. |
| 6,165,183 A | 12/2000 | Kuehn et al. |
| 6,187,003 B1 | 2/2001 | Buysse et al. |
| 6,190,408 B1 | 2/2001 | Melvin |
| 6,203,553 B1 | 3/2001 | Robertson et al. |
| 6,206,893 B1 | 3/2001 | Klein et al. |
| 6,210,432 B1 | 4/2001 | Solem et al. |
| 6,245,079 B1 | 6/2001 | Nobles et al. |
| 6,258,021 B1 | 7/2001 | Wilk |
| 6,267,746 B1 | 7/2001 | Bumbalough |
| 6,269,819 B1 | 8/2001 | Oz et al. |
| 6,299,637 B1 | 10/2001 | Shaolian et al. |
| 6,306,133 B1 | 10/2001 | Tu et al. |
| 6,312,447 B1 | 11/2001 | Grimes |
| 6,319,250 B1 | 11/2001 | Falwell et al. |
| 6,322,559 B1 | 11/2001 | Daulton et al. |
| 6,332,893 B1 | 12/2001 | Mortier et al. |
| 6,355,030 B1 | 3/2002 | Aldrich et al. |
| 6,368,326 B1 | 4/2002 | Dakin et al. |
| 6,402,781 B1 | 6/2002 | Langberg et al. |
| 6,406,420 B1 | 6/2002 | McCarthy et al. |
| 6,461,366 B1 | 10/2002 | Seguin |
| 6,464,707 B1 | 10/2002 | Bjerken |
| 6,482,224 B1 | 11/2002 | Michler et al. |
| 6,537,314 B2 | 3/2003 | Langberg et al. |
| 6,551,331 B2 | 4/2003 | Nobles et al. |
| 6,562,037 B2 | 5/2003 | Paton et al. |
| 6,562,052 B2 | 5/2003 | Nobles et al. |
| 6,575,971 B2 | 6/2003 | Hauck et al. |
| 6,585,761 B2 | 7/2003 | Taheri |
| 6,599,311 B1 | 7/2003 | Biggs et al. |
| 6,616,684 B1 | 9/2003 | Vidlund et al. |
| 6,619,291 B2 | 9/2003 | Hlavka et al. |
| 6,626,899 B2 | 9/2003 | Houser et al. |
| 6,626,930 B1 | 9/2003 | Allen et al. |
| 6,629,534 B1 | 10/2003 | St. Goar et al. |
| 6,641,592 B1 | 11/2003 | Sauer et al. |
| 6,656,221 B2 | 12/2003 | Taylor et al. |
| 6,689,164 B1 | 2/2004 | Seguin |
| 6,695,866 B1 | 2/2004 | Kuehn et al. |
| 6,701,929 B2 | 3/2004 | Hussein |
| 6,702,826 B2 | 3/2004 | Liddicoat et al. |
| 6,709,382 B1 | 3/2004 | Homer |
| 6,709,456 B2 | 3/2004 | Langberg et al. |
| 6,723,038 B1 | 4/2004 | Schroeder et al. |
| 6,726,716 B2 | 4/2004 | Marquez |
| 6,740,107 B2 | 5/2004 | Loeb et al. |
| 6,746,471 B2 | 6/2004 | Mortier et al. |
| 6,752,813 B2 | 6/2004 | Goldfarb et al. |
| 6,755,777 B2 | 6/2004 | Schweich et al. |
| 6,764,510 B2 | 7/2004 | Vidlund et al. |
| 6,767,349 B2 | 7/2004 | Ouchi |
| 6,770,083 B2 | 8/2004 | Seguin |
| 6,797,001 B2 | 9/2004 | Mathis et al. |
| 6,797,002 B2 | 9/2004 | Spence et al. |
| 6,875,224 B2 | 4/2005 | Grimes |
| 6,945,978 B1 | 9/2005 | Hyde |
| 6,949,122 B2 | 9/2005 | Adams et al. |
| 6,966,914 B2 | 11/2005 | Abe |
| 6,986,775 B2 | 1/2006 | Morales et al. |
| 7,011,669 B2 | 3/2006 | Kimblad |
| 7,048,754 B2 | 5/2006 | Martin et al. |
| 7,112,207 B2 | 9/2006 | Allen et al. |
| 7,226,467 B2 | 6/2007 | Lucatero et al. |
| 7,563,267 B2 | 7/2009 | Goldfarb et al. |
| 7,704,269 B2 | 4/2010 | St. Goar et al. |
| 8,142,495 B2 | 3/2012 | Hasenkam et al. |
| 2001/0037084 A1 | 11/2001 | Nardeo |
| 2002/0013571 A1 | 1/2002 | Goldfarb et al. |
| 2002/0035361 A1 | 3/2002 | Houser et al. |
| 2002/0087148 A1 | 7/2002 | Brock et al. |
| 2002/0087169 A1 | 7/2002 | Brock et al. |
| 2002/0156526 A1 | 10/2002 | Hilavka et al. |
| 2002/0161378 A1 | 10/2002 | Downing |
| 2002/0169360 A1 | 11/2002 | Taylor et al. |
| 2002/0183766 A1 | 12/2002 | Seguin |
| 2002/0183835 A1 | 12/2002 | Taylor et al. |
| 2003/0050693 A1 | 3/2003 | Quijano et al. |
| 2003/0069570 A1 | 4/2003 | Witzel et al. |
| 2003/0069593 A1 | 4/2003 | Tremulis et al. |
| 2003/0069636 A1 | 4/2003 | Solem et al. |
| 2003/0074012 A1 | 4/2003 | Nguyen et al. |
| 2003/0078654 A1 | 4/2003 | Taylor et al. |
| 2003/0105519 A1 | 6/2003 | Fasol et al. |
| 2003/0120341 A1 | 6/2003 | Shennib et al. |
| 2003/0130730 A1 | 7/2003 | Cohn et al. |
| 2003/0130731 A1 | 7/2003 | Vidlund et al. |
| 2003/0167071 A1 | 9/2003 | Martin et al. |
| 2003/0187467 A1 | 10/2003 | Schreck |
| 2003/0199975 A1 | 10/2003 | Gabbay |
| 2003/0208231 A1 | 11/2003 | Williamson, IV et al. |
| 2003/0229395 A1 | 12/2003 | Cox |
| 2003/0233038 A1 | 12/2003 | Hassett |
| 2004/0003819 A1 | 1/2004 | St. Goar et al. |
| 2004/0019377 A1 | 1/2004 | Taylor et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0039442 A1 | 2/2004 | St. Goar et al. |
| 2004/0039443 A1 | 2/2004 | Solem et al. |
| 2004/0044350 A1 | 3/2004 | Martin et al. |
| 2004/0049207 A1 | 3/2004 | Goldfarb et al. |
| 2004/0049211 A1 | 3/2004 | Tremulis et al. |
| 2004/0073302 A1 | 4/2004 | Rourke et al. |
| 2004/0078053 A1 | 4/2004 | Berg et al. |
| 2004/0087975 A1 | 5/2004 | Lucatero et al. |
| 2004/0088047 A1 | 5/2004 | Spence et al. |
| 2004/0092962 A1 | 5/2004 | Thorton et al. |
| 2004/0097979 A1 | 5/2004 | Svanidze et al. |
| 2004/0106989 A1 | 6/2004 | Wilson et al. |
| 2004/0111099 A1 | 6/2004 | Nguyen et al. |
| 2004/0122448 A1 | 6/2004 | Levine |
| 2004/0127981 A1 | 7/2004 | Randert et al. |
| 2004/0127982 A1 | 7/2004 | Machold et al. |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0133192 A1 | 7/2004 | Houser et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0138745 A1 | 7/2004 | Macoviak et al. |
| 2004/0143323 A1 | 7/2004 | Chawla |
| 2004/0148021 A1 | 7/2004 | Cartledge et al. |
| 2004/0152947 A1 | 8/2004 | Schroeder et al. |
| 2004/0153144 A1 | 8/2004 | Seguin |
| 2004/0158123 A1 | 8/2004 | Jayaraman |

(56) References Cited

U.S. PATENT DOCUMENTS

| | | |
|---|---|---|
| 2004/0162610 A1 | 8/2004 | Laiska et al. |
| 2004/0167539 A1 | 8/2004 | Kuehn et al. |
| 2004/0186566 A1 | 9/2004 | Hindrichs et al. |
| 2004/0193191 A1 | 9/2004 | Starksen et al. |
| 2004/0215339 A1 | 10/2004 | Drasler et al. |
| 2004/0220593 A1 | 11/2004 | Greenhalgh |
| 2004/0220657 A1 | 11/2004 | Nieminen et al. |
| 2004/0225300 A1 | 11/2004 | Goldfarb et al. |
| 2004/0236354 A1 | 11/2004 | Seguin |
| 2004/0243229 A1 | 12/2004 | Vidlund et al. |
| 2004/0249452 A1 | 12/2004 | Adams et al. |
| 2004/0249453 A1 | 12/2004 | Cartledge et al. |
| 2005/0004583 A1 | 1/2005 | Oz et al. |
| 2005/0004665 A1 | 1/2005 | Aklog |
| 2005/0004668 A1 | 1/2005 | Aklog et al. |
| 2005/0021056 A1 | 1/2005 | St. Goer et al. |
| 2005/0021057 A1 | 1/2005 | St. Goer et al. |
| 2005/0033446 A1 | 2/2005 | Deem et al. |
| 2005/0038508 A1 | 2/2005 | Gabbay |
| 2005/0049698 A1 | 3/2005 | Bolling et al. |
| 2005/0055089 A1 | 3/2005 | Macoviak et al. |
| 2005/0059351 A1 | 3/2005 | Cauwels et al. |
| 2005/0148815 A1 | 7/2005 | Mortier et al. |
| 2005/0149014 A1 | 7/2005 | Hauck et al. |
| 2005/0159810 A1 | 7/2005 | Filsoufi |
| 2005/0177180 A1 | 8/2005 | Kaganov et al. |
| 2005/0197694 A1 | 9/2005 | Pai et al. |
| 2005/0197695 A1 | 9/2005 | Stacchino et al. |
| 2005/0216039 A1 | 9/2005 | Lederman |
| 2005/0228422 A1 | 10/2005 | Machold et al. |
| 2005/0228495 A1 | 10/2005 | Macoviak |
| 2005/0251001 A1 | 11/2005 | Hassett |
| 2005/0267493 A1 | 12/2005 | Schreck et al. |
| 2005/0273160 A1 | 12/2005 | Lashinski et al. |
| 2005/0277966 A1 | 12/2005 | Ewers et al. |
| 2006/0004247 A1 | 1/2006 | Kute et al. |
| 2006/0015003 A1 | 1/2006 | Moaddes et al. |
| 2006/0020275 A1 | 1/2006 | Goldfarb et al. |
| 2006/0030866 A1 | 2/2006 | Schreck |
| 2006/0030867 A1 | 2/2006 | Zadno |
| 2006/0030885 A1 | 2/2006 | Hyde |
| 2006/0058871 A1 | 3/2006 | Zakay et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0089671 A1 | 4/2006 | Goldfarb et al. |
| 2006/0089711 A1 | 4/2006 | Dolan |
| 2006/0195012 A1 | 8/2006 | Mortier et al. |
| 2006/0195183 A1 | 8/2006 | Navia et al. |
| 2006/0229708 A1 | 10/2006 | Powell et al. |
| 2006/0241745 A1 | 10/2006 | Solem |
| 2006/0252984 A1 | 11/2006 | Randert et al. |
| 2006/0287716 A1 | 12/2006 | Banbury et al. |
| 2007/0038293 A1 | 2/2007 | St.Goar et al. |
| 2007/0118151 A1 | 5/2007 | Davidson |
| 2007/0118154 A1 | 5/2007 | Crabtree |
| 2007/0198082 A1 | 8/2007 | Kapadia et al. |
| 2008/0039935 A1 | 2/2008 | Buch et al. |
| 2008/0125860 A1 | 5/2008 | Webler et al. |
| 2008/0125861 A1 | 5/2008 | Webler et al. |
| 2008/0319541 A1 | 12/2008 | Filsoufi |
| 2009/0043382 A1 | 2/2009 | Maurer et al. |
| 2009/0149949 A1 | 6/2009 | Quinn |
| 2009/0177266 A1 | 7/2009 | Powell et al. |
| 2009/0198322 A1 | 8/2009 | Deem et al. |
| 2009/0270858 A1 | 10/2009 | Hauck et al. |
| 2010/0100108 A1 | 4/2010 | Goldfarb et al. |
| 2010/0185276 A1 | 7/2010 | Vidlund et al. |
| 2010/0318184 A1 | 12/2010 | Spence |
| 2011/0029071 A1 | 2/2011 | Zlotnick et al. |
| 2011/0077733 A1 | 3/2011 | Solem |
| 2011/0224784 A1 | 9/2011 | Quinn |
| 2012/0078358 A1 | 3/2012 | Vidlund et al. |
| 2013/0090728 A1 | 4/2013 | Solem |

FOREIGN PATENT DOCUMENTS

| | | |
|---|---|---|
| EP | 0 684 012 | 11/1995 |
| EP | 0 727 239 | 8/1996 |
| EP | 1 674 040 A2 | 6/2006 |
| EP | 1752115 A1 | 2/2007 |
| FR | 2 768 324 A1 | 3/1999 |
| GB | 1 598 111 A | 9/1981 |
| GB | 2 151 142 A | 7/1985 |
| JP | 11-089937 | 4/1999 |
| WO | 81/00668 | 3/1981 |
| WO | 91/01689 | 2/1991 |
| WO | 91/18881 | 12/1991 |
| WO | 92/12690 | 8/1992 |
| WO | 94/18881 | 9/1994 |
| WO | 94/18893 | 9/1994 |
| WO | 97/39688 | 10/1997 |
| WO | 98/07375 | 2/1998 |
| WO | 98/24372 | 6/1998 |
| WO | 98/30153 | 7/1998 |
| WO | 98/35638 | 8/1998 |
| WO | 99/00059 | 1/1999 |
| WO | 99/01377 | 1/1999 |
| WO | 99/07354 | 2/1999 |
| WO | 00/03759 | 1/2000 |
| WO | 00/59382 | 10/2000 |
| WO | 00/60995 | 10/2000 |
| WO | 01/26557 | 4/2001 |
| WO | 01/26586 | 4/2001 |
| WO | 01/28432 | 4/2001 |
| WO | 01/54618 | 8/2001 |
| WO | 02/003892 | 1/2002 |
| WO | WO 02/085251 A1 | 10/2002 |
| WO | 03/001893 | 1/2003 |
| WO | 03/003930 A1 | 1/2003 |
| WO | 03/020179 | 3/2003 |
| WO | 03/028558 | 4/2003 |
| WO | 03/037171 | 5/2003 |
| WO | 03/047467 | 6/2003 |
| WO | 03/049619 | 6/2003 |
| WO | 03/073913 | 9/2003 |
| WO | 03/105667 | 12/2003 |
| WO | 04/004607 A1 | 1/2004 |
| WO | 04/012583 A1 | 2/2004 |
| WO | 04/012789 A1 | 2/2004 |
| WO | 04/019811 A2 | 3/2004 |
| WO | 04/030570 A2 | 4/2004 |
| WO | 2004/030568 A2 | 4/2004 |
| WO | 04/037317 A2 | 5/2004 |
| WO | 04/045370 A2 | 6/2004 |
| WO | 04/045378 A2 | 6/2004 |
| WO | 04/045463 A2 | 6/2004 |
| WO | 04/047679 A2 | 6/2004 |
| WO | 04/062725 A1 | 7/2004 |
| WO | 04/082523 A2 | 9/2004 |
| WO | 2004/082538 A2 | 9/2004 |
| WO | 04/093730 A2 | 11/2004 |
| WO | 04/112651 A2 | 12/2004 |
| WO | 2004/112585 A2 | 12/2004 |
| WO | 05/002424 A2 | 1/2005 |
| WO | 05/018507 A2 | 3/2005 |
| WO | 05/027797 A1 | 3/2005 |
| WO | 05/032421 A2 | 4/2005 |
| WO | 05/062391 A2 | 7/2005 |
| WO | 05/112792 A2 | 12/2005 |
| WO | 2006/019521 A2 | 2/2006 |
| WO | 06/086434 A1 | 8/2006 |
| WO | 06/105008 A1 | 10/2006 |
| WO | 06/105009 A1 | 10/2006 |
| WO | 06/115875 A2 | 11/2006 |
| WO | 06/115876 A2 | 11/2006 |
| WO | 06/116558 A2 | 11/2006 |
| WO | 06/127509 A2 | 11/2006 |
| WO | 08/141322 A2 | 11/2008 |

(56) References Cited

FOREIGN PATENT DOCUMENTS

| WO | 09/064998 A1 | 5/2009 |
|---|---|---|
| WO | 09/072114 A2 | 6/2009 |

OTHER PUBLICATIONS

Abe et al., "Updated: De Vega's annuloplasty for acqiuried tricuspid-disease: Early and late results in 110 patients" Ann. Thorac. Surg. (Dec. 1996) 62:1876-1877.
Agricola et al., "Mitral valve reserve in double orifice technique: an exercise echocardiographic study," Journal of Heart Valve Disease, (Sep. 2002) 11(5):637-643.
Alfieri et al., "An effective technique to correct anterior mitral leaflet prolapse," J. Card. Surg., (Nov./Dec. 1999) 14(6): 468-470.
Alfieri et al., "Novel suture device for beating heart mitral leafletapproximation," Annals of Thoracic Surgery, (Nov. 2002) 74: 1488-1493.
Alfieri et al., "The double orifice technique in mitral valve repair: a simple solution for complex problems," Journal of Thoracic CardiovascularSurgery, (Oct. 2001) 122: 674-681.
Alfieri, "The edge to edge repair of the mitral valve," [Abstract] 6th Annual New Era Cardiac Care: Innovation & Technology,Heart Surgery Forum, (Jan. 2003) pp. 103.
Alvarez et al., "Repairing the Degenerative Mitral Valve: Ten- to Fifteen-Year Follow-up," J. Thorac. Cardiovasc. Surg. (Aug. 1996) 112:238-247.
Arisi et al., "Mitral valve repair with Alfieri technique in mitral regurgitation of diverse etiology: early echocardiographic results," Circulation Supplement II, (Oct. 2001) 104(17):3240.
Bach et al., "Early improvement in congestive heart failure after correction of secondary mitral regurgitation in end-stagecardiomyopathy," Am. Heart J., (Jun. 1995) 129:1165-1170.
Bach et al., "Improvement following correction of secondary mitral regurgitation in end-stage cardiomyopathy with mitral annuloplasty," Am. J. Cardiol., (Oct. 1996) 78:966-969.
Bailey, "Surgery of the Heart," Chapter 20, (1995) pp. 686-737.
Bernal et al., "The 'Valve Racket': a new and different concept of atrioventricular valve repair," Eur. J. Cardio-thoracic Surgery 29:1026-29 (Jun. 2006).
Bhudia, S., "Edge-to-edge mitral repair: a versatile mitral repair technique," The Cleveland Clinic Foundation, Cleveland, Ohio, www.ctsnet.org/doc/7007 (accessed on Dec. 14, 2004).
Bolling et al., "Surgery for acquired heart disease" (Apr. 1995) 109:676-683.
Borghetti et al., "Preliminary observations on haemodynamics during physiological stress conditions following 'double-orifice' mitral valve repair," European Journal of Cardio-thoracic Surgery, Apr. 18, 2001 20: 262-269.
Castedo, "Edge-to-edge tricuspid repair for redeveloped valve incompetence after DeVega's annuloplasty," Ann Thora Surg., (Feb. 2003) 75:605-606.
Communication dated Jun. 29, 2017, from the European Patent Office in counterpart European Application No. 06734547.0.
Communication dated Mar. 12, 2015, issued by the European Patent Office in counterpart European application No. 10 757 366.9.
Communication dated Mar. 22, 2017, from the European Patent Office in counterpart European Application No. 16180035.4.
Communication dated Sep. 28, 2015 from the Canadian Intellectual Property Office in counterpart application No. 2,822,801.
Dec et al., "Idiopathic dilated cardiomyopathy," N. Engl. J.Med. (Dec. 1994) 331:1564-1575.
Derwent citing French language patent, FR2768324 published Mar. 19, 1999, for: "Surgical instrument for joining soft tissues through percutaneous access" WPI Acc No: 1999231954/199920.
Derwent citing German language patent, EP 684012 published Nov. 12, 1995, for: "Thread for constructing surgical seam—has flexible section with two ends, with lower fastening part on thread first end having hollow cylinder with continuous hole through which surgical needle threads".
Derwent citing Japanese language patent, JP 11089937 published Jun. 4, 1999, for: "Catheter for mitral regurgitation test—includes jet nozzles provided on rear side of large diametered spindle shaped portion attached to end of narrow diametered tube".
Dottori et al., "Echocardiographic imaging of the Alfieri type mitral valve repair," Ital. Heart J., (Apr. 2001) 2(4): 319-320.
Downing et al., "Beating heart mitral valve surgery: Preliminary model and methodology," Journal of Thoracic and Cardiovascular Surgery, (Jun. 2002) 123(6):1141-1146.
Falk et al., "Computer-enhanced mitral valve surgery: toward a total endoscopic procedure," Seminars in thoracic and cardiovascular surgery, (Jul. 1999) 11(3): 224-249.
Filsoufi et al., "Restoring Optimal Surface of Coaptation With a Mini Leaflet Prosthesis: A New Surgical Concept for the Correction of Mitral Valve Prolapse," Intl. Soc. For Minimally Invasive Cardiothoracic Surgery (Sep. 2006) 1(4):186-87.
Fucci et al., "Improved results with mitral valve repair using new surgical techniques", Eur. J. Cardiothorac. Surg. (Nov. 1995) 9:621-627.
Fundaro et al., "Chordal placation and free edge remodeling for mitral anterior leaflet prolapse repair: 8-year follow-up," Annals of ThoracicSurgery, (Nov. 2001) 72:1515-1519.
G. Noera et al "Tricuspid Valve Incompetence Caused by Nonpenetrating Thoracic Trauma", Annals of Thoracic Surgery 51(2) (1991) p. 320-22.
Garcia-Rinaldi et al., "Left ventricular volume reduction and reconstruction is ischemic cardiomyopathy," Journal of Cardiac Surgery, (May/Jun. 1999) 14:199-210.
Gateliene, "Early and postoperative results results of metal and tricuspid valve insufficiency surgical treatment using edge-to-edge central coaptation procedure," (Oct. 2002) 38 (Suppl 2):172-175.
Gatti et al., "The edge to edge technique as a trick to rescue an imperfect mitral valve repair," Eur. J. Cardiothorac Surg, (Nov. 2002) 22(5): 817-20.
Gillinov et al., "Is minimally invasive heart valve surgery a paradigm for the future?," Current Cardiology Reports, (Nov. 1999) 1:318-322.
Gundry et al., "Facile Minimally Invasive Cardiac Surgery via Ministemotomy," Ann. Thorac. Surg. 65: 1100-1104(1998).
Ikeda et al., "Batista's operation with coronary artery bypass grafting and mitral valve plasty for ischemic dilated cardiomyopathy," The Japanese Journal of Thoracic and Cardiovascular Surgery, (Nov. 2000) 48:746-749.
Izzat et al., "Early experience with partial left ventriculectomy in the Asis-Pacific Region," Annals of Thoracic Surgery, (Jun. 1999) 67: 1703-1707.
Kallner et al., "Transaortic approach for the Alfieri Stitch," Ann Thorac Surg, (Jan. 2001) 71: 378-380.
Kameda et al., "Annuloplasty for severe mitral regurgitation due to dilated cardiomyopathy," Am. Thorac. Surg. (Jun. 1996) 61:1829-1832.
Kavarna et al., "Transaortic repair of mitral regurgitation," Presented at the third annualNew Era Cardiac Care conference, San Diego, CA, Jan. 13-16, 2000,http://www.hsforum.com/vol3/issue1/2000-2389print.html.
Kaza et al., "Ventricular reconstruction results in improved left ventricular function and amelioration of mitral insufficiency," Annals of Surgery, (Jun. 2002) 235(6): 828-832.
Khan et al. "Blade atrial septostomy: Experience with the first 50 procedures" Cathet. Cardiovasc. Diagn. (Aug. 1991) 23: 257-262.
Kherani, "The edge-to-edge mitral valve repair: the Columbia Presbyterian experience," Ann. Thorac. Surg. 78: 73-76 (2004).
Konertz et al., "Results after partial left venticulectomy in a European heart failure population," Journal of Cardiac Surgery, (Mar./Apr. 1999) 14(2): 129-135.
Kron et al., "Surgical relocation of the posterior papillary muscle in chronic ischemic mitral regurgitation," Annals. of Thoracic Surgery, (Aug. 2002) 74:600-601.
Kruger et al., "Edge to edge technique in complex mitral valve repair," Thorac Cardiovasc Surg. 48 (Supplement I): p. 106 (abstract p. 73) (2000).

(56) References Cited

OTHER PUBLICATIONS

Langer et al., "Posterier mitral leaflet extensions: An adjunctive repair option for ischemic mitral regurgitation?," J Thorac Cardiovasc Surg, (Apr. 2006) 131:868-77.

Lorusso et al., "'Double-Orifice' technique to repair extensive mitral valve excision following acute endocarditis," J. Card Surg, (Jan. 1998) 13:24-26.

Lorusso et al., The double-orifice technique for mitral valve construction: predictors ofpostoperative outcome, Eur J. Cardiothorac Surg, May 23, 2001; 20(3):583-589.

Maisano et al., "The double orifice repair for Barlow Disease: a simple solution for a complex repair," Supplement I Circulation, (Nov. 1999); 100(18):1-94.

Maisano et al., "The double orifice technique as a standardized approach to treat mitral regurgitation due to severe myxomatous disease: surgical technique," European Journal of Cardiothoracic Surgery, Jan. 18, 2000; 17:201-215.

Maisano et al., "The edge-to-edge technique: A simplified method to correct mitral insufficiency" Eur. J. Cardiothorac. Surg., (Mar. 1998) 13:240-246.

Maisano et al., "The hemodynamic effects of double-orifice valve repair for mitral regurgitation: a 3D computational model," European Journal of Cardio-thoracic Surgery, (Apr. 1999); 15: 419-425.

Maisano et al., "Valve repair for traumatic tricuspid regurgitation," Eur. J. Cardio-thorac Surg, (Oct. 1996) 10: 867-873.

Mantovani et al., "Edge-to-edge repair of congenital familiar tricuspid regurgitation: case report," J. Heart Valve Dis., (Sep. 2000) 9(5):641-643.

McCarthy et al., "Partial left ventriculectony and mitral valve repair for end-stage congestive heart failure," European Journal of CardiothoracicSurgery, (Apr. 1998) 13:337-343.

McCarthy et al., "Tricuspid Valve Reapir with the Cosgrove-Edwards Annuloplasty System," Ann. Thorac. Surg., (Jul. 1997) 64:267-268.

Moainie et al., "Correction of traumatic tricuspid regurgitation using the double orifice technique," Annals of Thoracic Surgery, (Mar. 2002) 73: 963-965.

Morales et al., "Development of an off bypass mitral valve repair," The Heart Surgery Forum #1999-4693, (Apr. 1999) 2(2):115-120.

Nakanishi et al., "Early outcome with the Alfieri mitral valve repair," J.Cardiol., (May 2001); 37(5): 263-266, [Abstract in English; Article in Japanese].

Nielsen et al., "The edge-to-edge mitral repair: tension of the approximating suture and leaflet deformation during acute ischemic mitral regurgitation in the ovine heart," Circulation, (Sep. 2001); 104(Suppl I):I-29-I-35.

Noera et al., "Tricuspid Valve Incompetence Caused by Nonpenetrating Thoracic Trauma", Annals of Thoracic Surger, 1991, 51 (2), 320-322.

Osawa et al., "Partial left ventriculectomy in a 3 year old boy with dilated cardiomyopathy," Japanese Journal of Thoracic and Cardiovascular Surg, Sep. 2000, 48(9):590-593.

Park et al., "Clinical use of a blade atrial septostomy" Circulation (Oct. 1978) 58:600-608.

Privitera et al., "Alfieri Mitral Valve Repair: Clinical Outcome and Pathology," Circulation, (Nov. 2002) 106:173.

Redaelli et al., "A computational study of the hemodynamics after 'edge-to-edge' mitral valve repair," Journal of Biomechanical Engineering, (Dec. 2001) 123:565-570.

Reul et al., "Mitral valve reconstruction for mitral insufficiency," Progress in Cardiovascular Diseases, (May/Jun. 1997) vol. XXXIX, No. 6, pp. 567-599.

Ricchi et al., "Linear segmental annuloplasty for mitral valve repair" Ann. Thorac. Surg., (Jun. 1997) 63:1805-1806.

Tager et al., "Long-term follow-up of rheumatic patients undergoing left-sided valve replacement with tricuspid annuloplasty—Validity of preoperative echocardiographic criteria in the decision to perform tricuspid annuloplasty," Am. J. Cardiol., (Apr. 1998) 81:1013-1016.

Tamura et al., "Edge to edge repair for mitral regurgitation on a patient with chronic hemodialysis: report of a case," Kyobu Geka, (Aug. 2001) 54(9):788-790.

Timek et al., "Edge-to-edge mitral repair: gradients and three-dimensional annular dynamics in vivo during inotropic stimulation," Eur J. of Cardiothoracic Surg., Jan. 9, 2001; 19:431-437.

Timek, "Edge-to-edge mitral valve repair without ring annuloplasty for acute ischemic mitral regurgitation," Circulation 108 (Supplement II): 11-122-11-127 (2003).

Totaro, "Mitral valve repair for isolated prolapse of the anterior leaflet: an 11-year follow-up," European Journal of Cardio-thoracic Surgery, (Feb. 1999) 15: 119-126.

Uchida et al., "Percutaneous cardiomyotomy and valvulotomy with angioscopic guidance," Am. Heart J., (Apr. 1991) 121:1221-1224.

Umana et al., "'Bow-tie' mitral valve repair successfully addresses subvalvular dysfunction in ischemic mitral regurgitation," (Oct. 1997) Surgical Forum, pp. 279-280.

Umana et al., "'Bow-tie' mitral valve repair: An Adjuvant technique for ischemic regurgitation" Ann. Thorac. Surg., (Nov. 1998) 66:1640-1646.

Votta et al., "3-D computational analysis of the stress distribution on the leaflets after edge-to-edge repair of mitral regurgitation," Journal of Heart Valve Disease, (Nov. 2002) 11: 810-822.

European Search Report dated Jun. 13, 2019 in Application No. EP19160744.

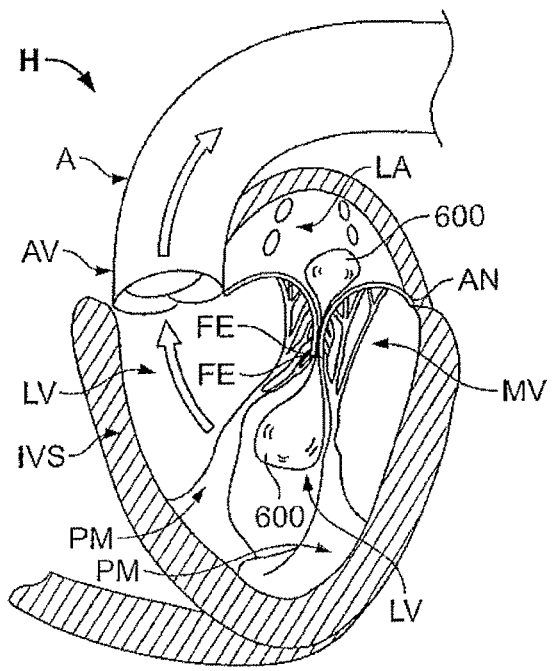 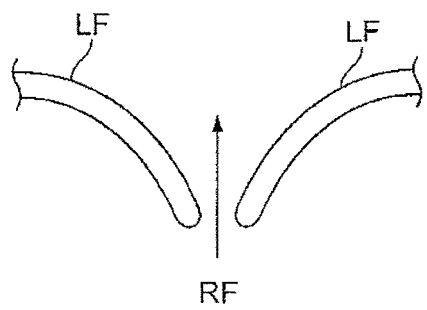
FIG. 7A  FIG. 7B
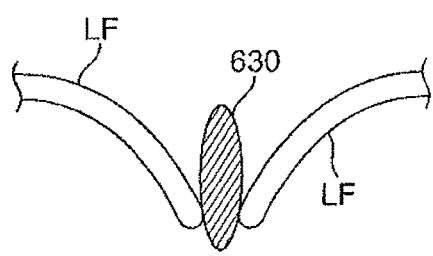 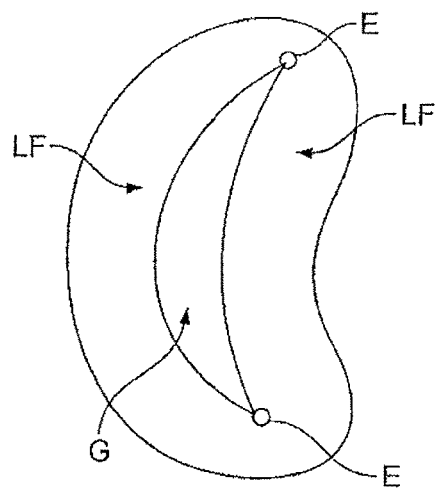
FIG. 7C  FIG. 7D

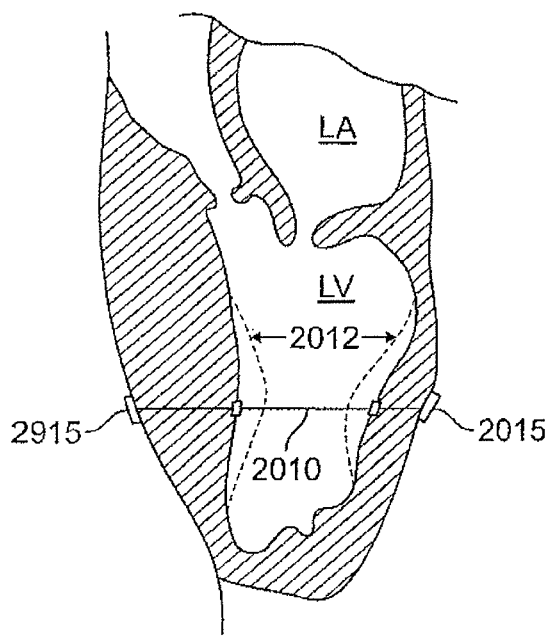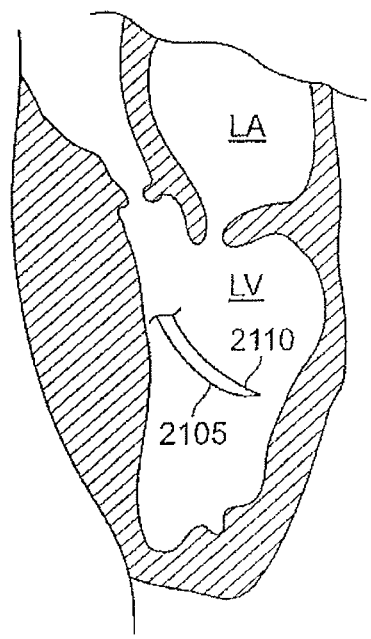
FIG. 20      FIG. 21
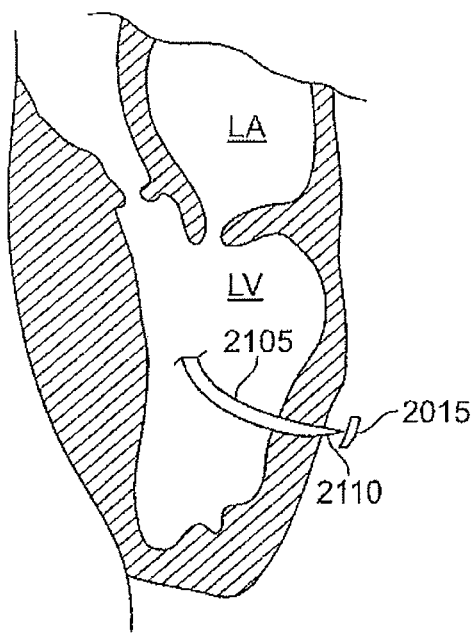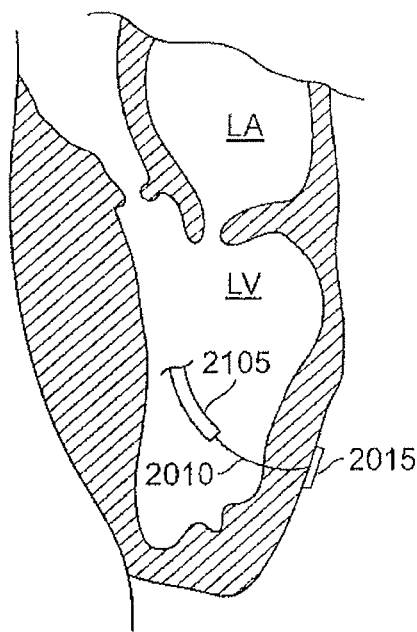
FIG. 22      FIG. 23

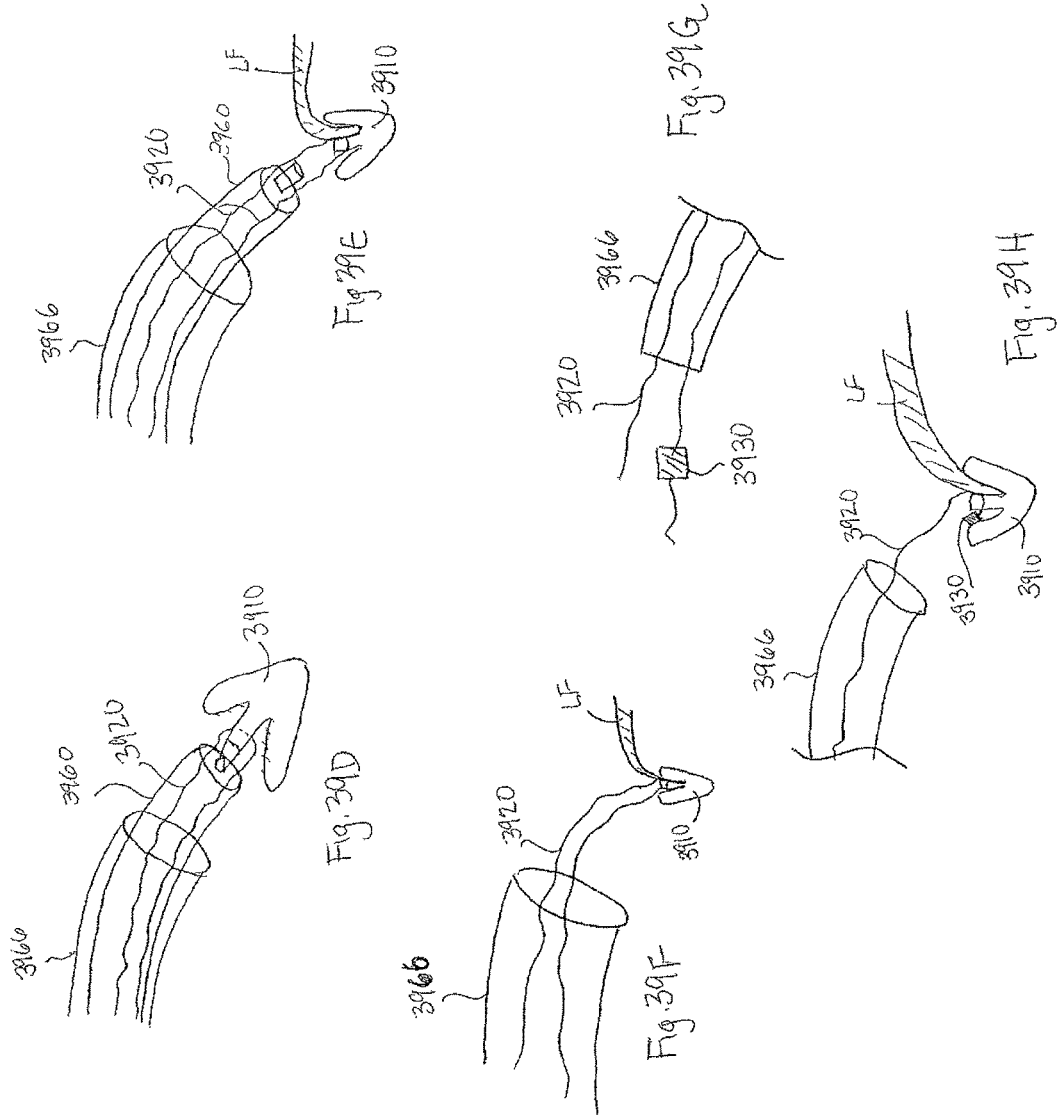

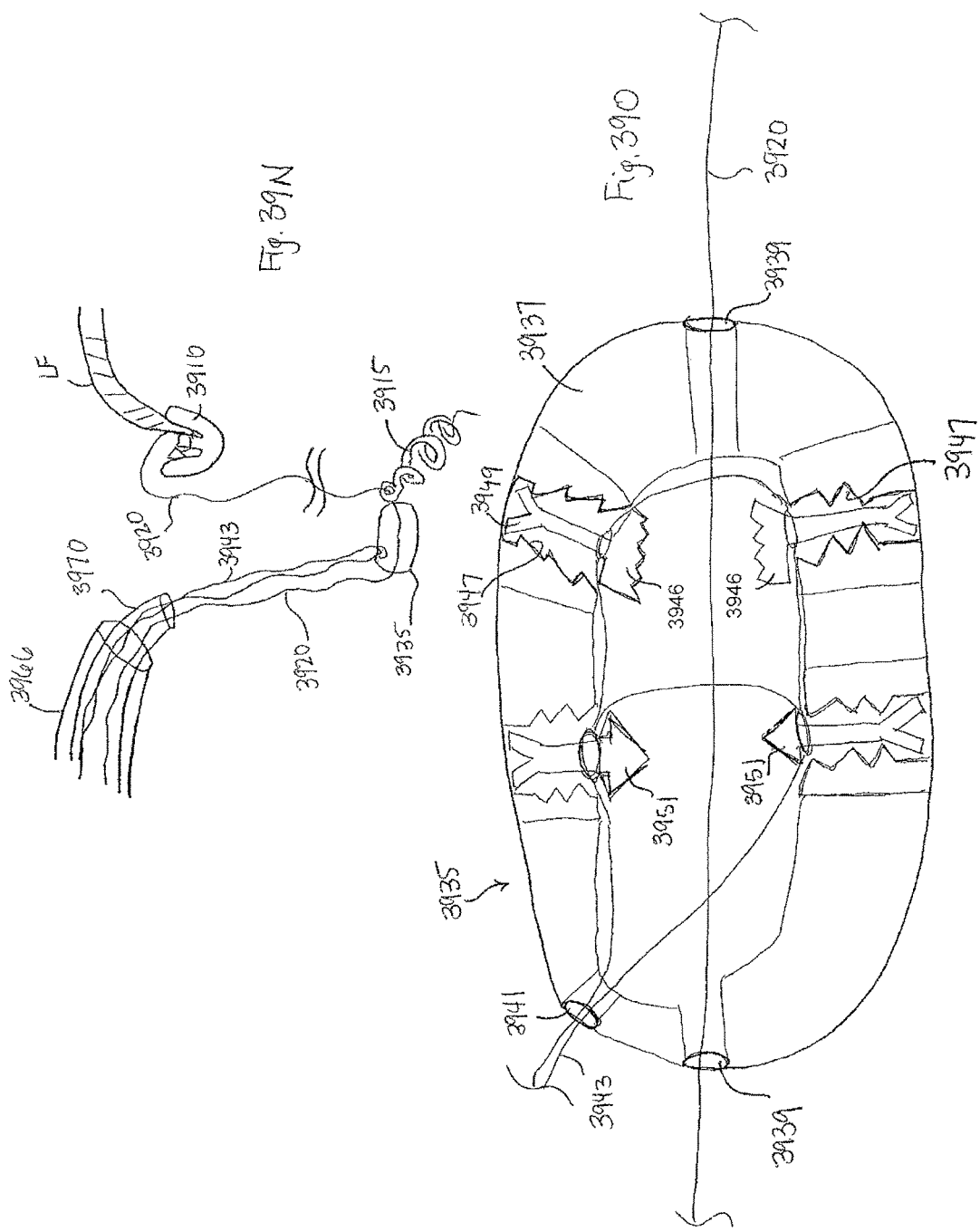

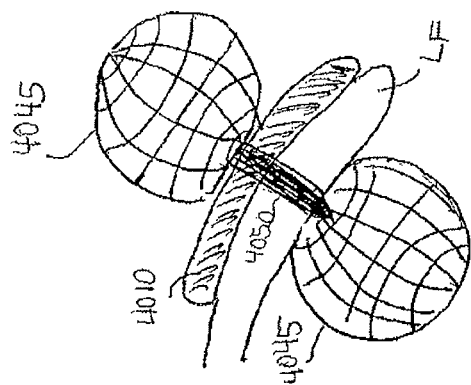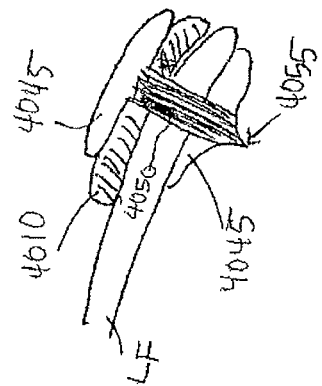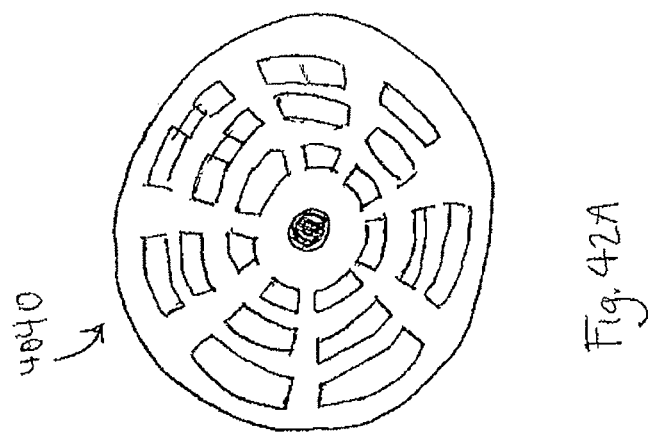

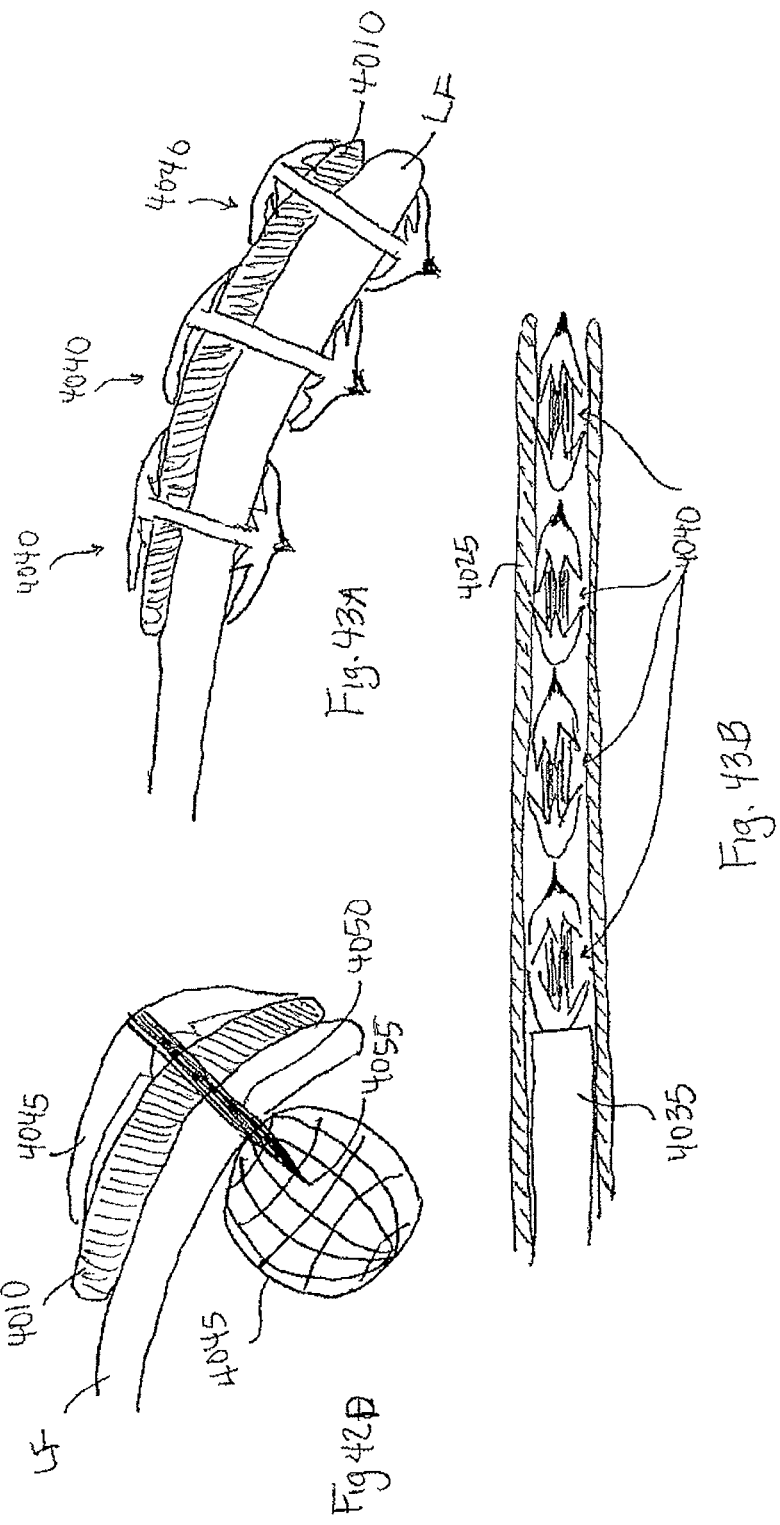

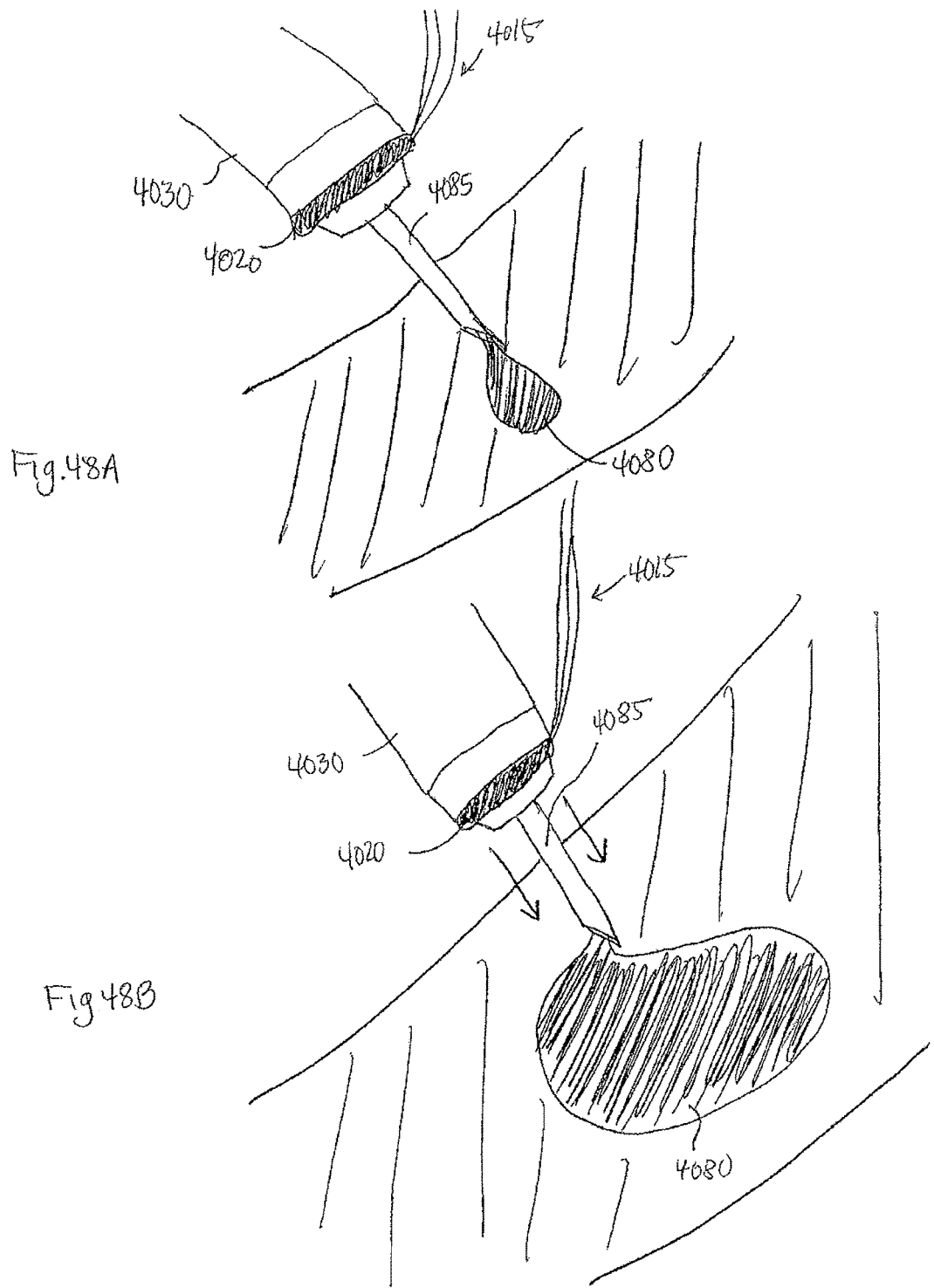

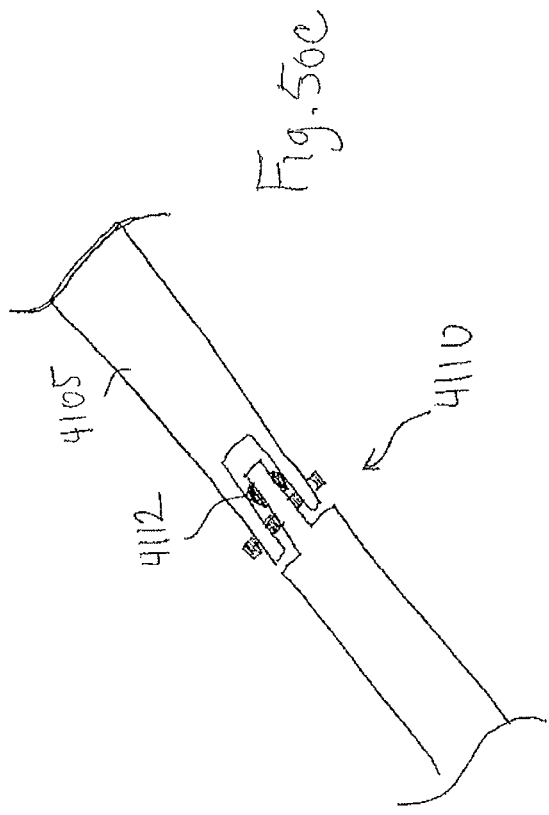
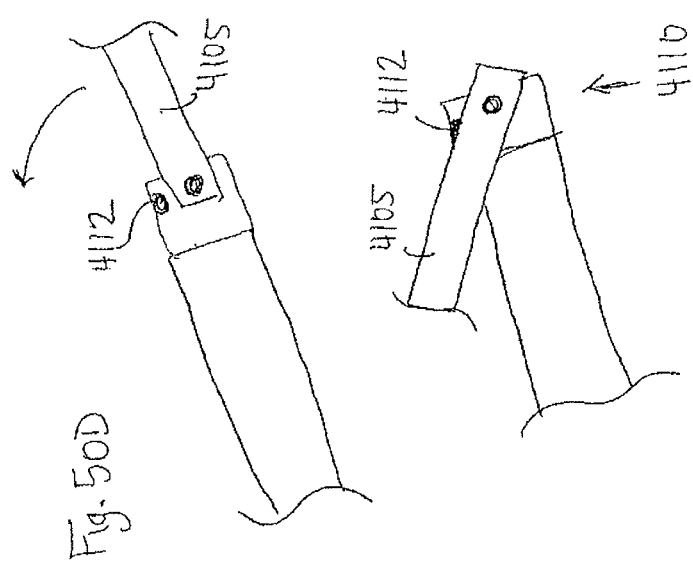

METHODS, SYSTEMS AND DEVICES FOR CARDIAC VALVE REPAIR

CROSS-REFERENCE TO RELATED APPLICATIONS

The present application is a divisional of U.S. patent application Ser. No. 15/082,137 filed Mar. 28, 2016 (pending) which is a divisional application of Ser. No. 13/852,459 filed Mar. 28, 2013 (abandoned), which is a divisional application of Ser. No. 12/883,095 filed Sep. 15, 2010 (abandoned), which claims the benefit of priority under 35 U.S.C. § 119(e) of U.S. Provisional Patent Application Ser. No. 61/243,459, filed Sep. 17, 2009. U.S. patent application Ser. No. 13/852,459 is also a continuation-in-part of U.S. patent application Ser. No. 11/349,742, filed on Feb. 7, 2006 (abandoned), which claims the benefit of priority under 35 U.S.C. § 119(e) of U.S. Provisional Patent Application Ser. No. 60/650,918 entitled "Methods, Systems and Devices for Cardiac Valve Repair," filed Feb. 7, 2005, and U.S. Provisional Patent Application Ser. No. 60/692,802 entitled "Methods, Systems and Devices for Cardiac Valve Repair," filed Jun. 21, 2005. Priority of the aforementioned filing dates is hereby claimed, and the full disclosures of the aforementioned applications are hereby incorporated by reference in their entirety.

BACKGROUND

The present invention relates generally to medical methods, devices, and systems. In particular, the present invention relates to methods, devices, and systems for the endovascular or minimally invasive surgical repair of the atrioventricular valves of the heart, particularly the mitral valve.

Mitral valve regurgitation is characterized by retrograde flow from the left ventricle of a heart through an incompetent mitral valve into the left atrium. During a normal cycle of heart contraction (systole), the mitral valve acts as a check valve to prevent flow of oxygenated blood back into the left atrium. In this way, the oxygenated blood is pumped into the aorta through the aortic valve. Regurgitation of the valve can significantly decrease the pumping efficiency of the heart, placing the patient at risk of severe, progressive heart failure.

Mitral valve regurgitation can result from a number of different mechanical defects in the mitral valve. The valve leaflets, the valve chordae which connect the leaflets to the papillary muscles, or the papillary muscles themselves may be damaged or otherwise dysfunctional. Commonly, the valve annulus may be damaged, dilated, or weakened limiting the ability of the mitral valve to close adequately against the high pressures of the left ventricle. In some cases the mitral valve leaflets detach from the chordae tendinae, the structure that tethers them to the ventricular wall so that they are positioned to coapt or close against the other valve leaflet during systole. In this case, the leaflet "flails" or billows into the left atrium during systole instead of coapting or sealing against the neighboring leaflet allowing blood from the ventricle to surge into the left atrium during systole. In addition, mitral valve disease can include functional mitral valve disease which is usually characterized by the failure of the mitral valve leaflets to coapt due to an enlarged ventricle, or other impediment to the leaflets rising up far enough toward each other to close the gap or seal against each other during systole.

The most common treatments for mitral valve regurgitation rely on valve replacement or strengthening of the valve annulus by implanting a mechanical support ring or other structure. The latter is generally referred to as valve annuloplasty. A recent technique for mitral valve repair which relies on suturing adjacent segments of the opposed valve leaflets together is referred to as the "bow-tie" or "edge-to-edge" technique. While all these techniques can be very effective, they usually rely on open heart surgery where the patient's chest is opened, typically via a sternotomy, and the patient placed on cardiopulmonary bypass. The need to both open the chest and place the patient on bypass is traumatic and has associated morbidity.

SUMMARY

For the foregoing reasons, it would be desirable to provide alternative and additional methods, devices, and systems for performing the repair of mitral and other cardiac valves, including the tricuspid valve, which is the other atrioventricular valve. In some embodiments of the present invention, methods and devices may be deployed directly into the heart chambers via a trans-thoracic approach, utilizing a small incision in the chest wall, or the placement of a cannula or a port. In other embodiments, such methods, devices, and systems may not require open chest access and be capable of being performed endovascularly, i.e., using devices which are advanced to the heart from a point in the patient's vasculature remote from the heart. Still more preferably, the methods, devices, and systems should not require that the heart be bypassed, although the methods, devices, and systems should be useful with patients who are bypassed and/or whose heart may be temporarily stopped by drugs or other techniques. At least some of these objectives will be met by the inventions described hereinbelow.

In an aspect, disclosed herein is a chordal replacement device having a proximal anchor including a flexible patch and a leaflet attachment device. The flexible patch is affixed to an upper surface of a portion of a flailing leaflet with the leaflet attachment device. The device also includes a distal anchor extending and affixed to a distal attachment site in a ventricle; and a flexible tether coupled to and tensioned between the proximal and distal anchors.

In another aspect, there is a chordal replacement device having a proximal anchor including a flexible crimp clip having one or more barbs that embed into and affix to a portion of a flailing leaflet; a distal anchor extending and affixed to a distal attachment site in a ventricle; and a flexible tether coupled to and tensioned between the proximal and distal anchors.

The device can include a leaflet attachment device having a pair of expandable elements interconnected by a central attachment rod. The pair of expandable elements can sandwich the flexible patch and the leaflet. The leaflet attachment device can include an expandable element. The expandable element can be self-deploying and can include a star-shaped barb, a mesh web, or a mesh ball. The proximal anchor can further include a mesh stent deployable within an atrium. The mesh stent can be coupled to a flexible rod that extends through a valve commissure into the ventricle. The distal end of the flexible rod can couple to the distal anchor and provide consistent tension on the tether during a heart cycle. The flexible rod can have a deflectable, spring-formed shape. The flexible rod can be jointed. The distal anchor and tensioned flexible tether can apply a downward force on the flailing leaflet. The distal anchor can include a weight, barb, adhesive, screw, or fluid-filled element. The distal attachment site can include a portion of the ventricle wall, ventricular septum or papillary muscle. The distal anchor can fine-tune the tension of the tether after the distal anchor is affixed to the distal attachment site. The distal anchor can include a coil screw and wherein rotation of the coil screw fine-tunes the tension on the tether. The distal anchor can include a balloon and wherein infusion of fluid into the balloon increases tension on the tether.

The flexible tether can have a length that can be adjusted to a desired tension to apply a downward force on the flailing leaflet. The flexible tether can include one or more loops of a flexible material. The one or more loops can be drawn together at a distal end region with an enclosed element. The enclosed element can couple the one or more loops to the distal anchor. The one or more loops can be coupled to the proximal and distal anchors such that the one or more loops self-equalize and evenly distribute tension on the flailing leaflets and on distal attachment site.

In another aspect, disclosed is a chordal replacement device including a proximal anchor comprising a flexible crimp clip having one or more barbs that embed into and affix to a portion of a flailing leaflet; a distal anchor extending and affixed to a distal attachment site in a ventricle; and a flexible tether coupled to and tensioned between the proximal and distal anchors.

The distal anchor and flexible tether can hold down the flailing leaflet. The distal anchor can include a weight, barb, adhesive, screw, or fluid-filled element. The distal attachment site can include a portion of the ventricle wall, ventricular septum or papillary muscle. The distal anchor can fine-tune the tension of the tether after the distal anchor is affixed to the distal attachment site. The distal anchor can include a coil screw and wherein rotation of the coil screw fine-tunes the tension on the tether. The distal anchor can include a balloon and wherein infusion of fluid into the balloon increases tension on the tether. The tether can have a length that can be adjusted to a desired tension to hold the leaflet down.

In another aspect, disclosed is a method for repairing a cardiac valve including accessing a patient's vasculature remote from the heart; advancing an interventional tool through an access sheath to a location near the cardiac valve, the interventional tool comprising a distal flange; affixing a chordal replacement device to a portion of a flailing leaflet, the chordal replacement device including a flexible patch; one or more leaflet attachment devices; a distal anchor; and a flexible tether coupled to and tensioned between the flexible patch and the distal anchor. The method also includes coupling the distal anchor to a distal attachment site in a ventricle; and applying a downward force on the flailing leaflet with the tether and distal anchor so as to prevent flail of the leaflet into the atrium.

Affixing a chordal replacement device can further include positioning the flexible patch on an upper surface of a flailing leaflet, piercing the patch and the leaflet with the one or more leaflet attachment devices, and sandwiching the leaflet and the patch between a pair of expandable elements. The pair of expandable elements can be self-deploying. The distal anchor can include a weight, barb, adhesive, coil screw or fluid-filled element. The distal attachment site can include a portion of the ventricle wall, ventricular septum or papillary muscle. The method can further include observing flow through the cardiac valve to determine if leaflet flail, valve prolapse or valve regurgitation are inhibited. The method can further include adjusting tension of the tether coupled to and tensioned between the flexible patch and the distal anchor. The distal anchor can include a coil screw and wherein adjusting the tension of the tether comprises rotating the coil screw. The distal anchor can include a balloon and wherein adjusting the tension of the tether comprises infusing fluid into the balloon. The method can further include sensing contact between the distal anchor and the distal attachment site.

Other features and advantages should be apparent from the following description of various embodiments, which illustrate, by way of example, the principles of the disclosure.

BRIEF DESCRIPTION OF THE DRAWINGS

FIG. 7A shows a cross-sectional view of a heart with a bladder device positioned partially within the left ventricle and partially within the left atrium.

FIG. 7B shows a schematic side view of the mitral valve leaflets failing to coapt.

FIG. 7C shows a schematic side view of the mitral valve leaflets with a bladder positioned between the leaflets.

FIG. 7D shows a plan view of the mitral valve with the leaflets in an abnormal closure state such that a gap is present between the leaflets.

FIG. 20 shows a cross-sectional view of the left ventricle with a tether positioned therein.

FIG. 21 shows a cross-sectional view of the left ventricle with a delivery catheter positioned therein.

FIG. 22 shows a cross-sectional view of the left ventricle with the delivery catheter penetrating a wall of the left ventricle.

FIG. 23 shows a cross-sectional view of the left ventricle with the delivery catheter delivering a patch to the wall of the left ventricle.

FIGS. 39A-39M show another embodiment of a chordal replacement device.

FIGS. 39N-39O show an embodiment of a dual function clamp and deployment of an embodiment of a chordal replacement device.

FIGS. 42A-42D show various embodiments of an expandable feature of an attachment device.

FIGS. 43A-43B show an embodiment of attachment devices fixing a patch to a valve leaflet.

FIGS. 48A-48B illustrate another embodiment of fine-tuning the tension on the artificial chordae.

FIGS. 50C-50E show an embodiment of a jointed rod having mechanical locking feature.

DETAILED DESCRIPTION

Figure 1B:
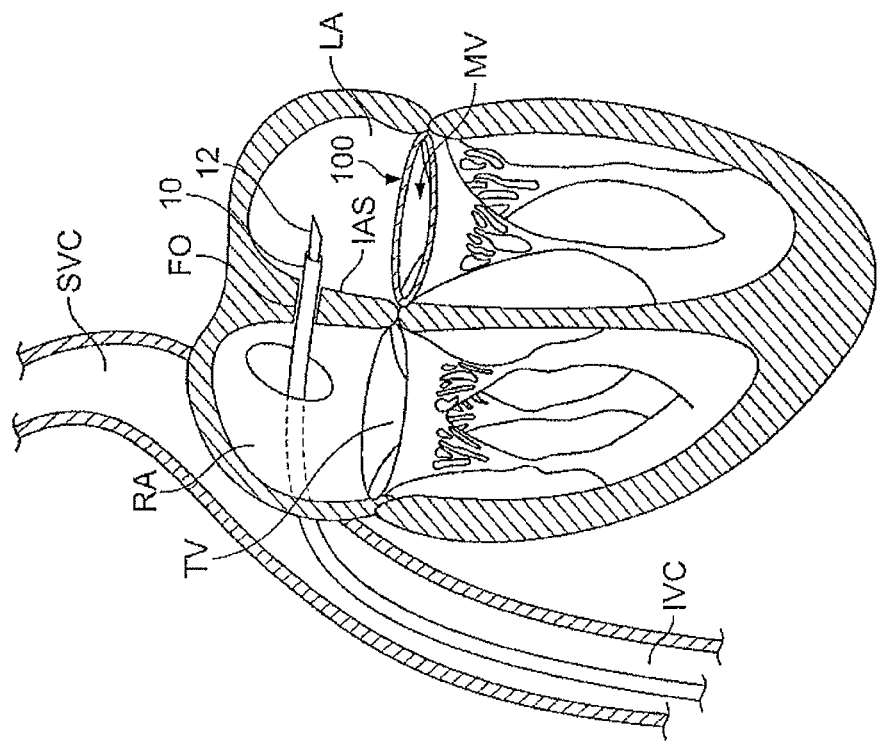
FIG. 1B shows a cross-sectional view of the heart wherein a flexible stent is positioned at or near the mitral valve.

The present invention provides methods, systems, and devices for the endovascular repair of cardiac valves, particularly the atrioventricular valves which inhibit back flow of blood from a heart ventricle during contraction (systole), most particularly the mitral valve between the left atrium and the left ventricle. By "endovascular," it is meant that the procedure(s) of the present invention are performed with interventional tools, guides and supporting catheters and other equipment introduced to the heart chambers from the patient's arterial or venous vasculature remote from the heart. The interventional tools and other equipment may be introduced percutaneously, i.e., through an access sheath, or may be introduced via a surgical cut down, and then advanced from the remote access site through the vasculature until they reach the heart. Thus, the procedures of the present invention will generally not require penetrations made directly through the exterior heart muscle, i.e., myocardium, although there may be some instances where penetrations will be made interior to the heart, e.g., through the interatrial septum to provide for a desired access route.

While the procedures of the present invention will usually be percutaneous and intravascular, many of the tools will find use in minimally invasive and open surgical procedures as well that includes a surgical incision or port access through the heart wall. In particular, the tools for capturing the valve leaflets prior to attachment can find use in virtually any type of procedure for modifying cardiac valve function.

The atrioventricular valves are located at the junctions of the atria and their respective ventricles. The atrioventricular valve between the right atrium and the right ventricle has three valve leaflets (cusps) and is referred to as the tricuspid or right atrioventricular valve. The atrioventricular valve between the left atrium and the left ventricle is a bicuspid valve having only two leaflets (cusps) and is generally referred to as the mitral valve. In both cases, the valve leaflets are connected to the base of the atrial chamber in a region referred to as the valve annulus, and the valve leaflets extend generally downwardly from the annulus into the associated ventricle. In this way, the valve leaflets open during diastole when the heart atria fill with blood, allowing the blood to pass into the ventricle.

During systole, however, the valve leaflets are pushed together and closed to prevent back flow of blood into the atria. The lower ends of the valve leaflets are connected through tendon-like tissue structures called the chordae, which in turn are connected at their lower ends to the papillary muscles. Interventions according to the present invention may be directed at any one of the leaflets, chordae, annulus, or papillary muscles, or combinations thereof. It will be the general purpose of such interventions to modify the manner in which the valve leaflets coapt or close during systole so that back flow or regurgitation is minimized or prevented.

Figure 1A:
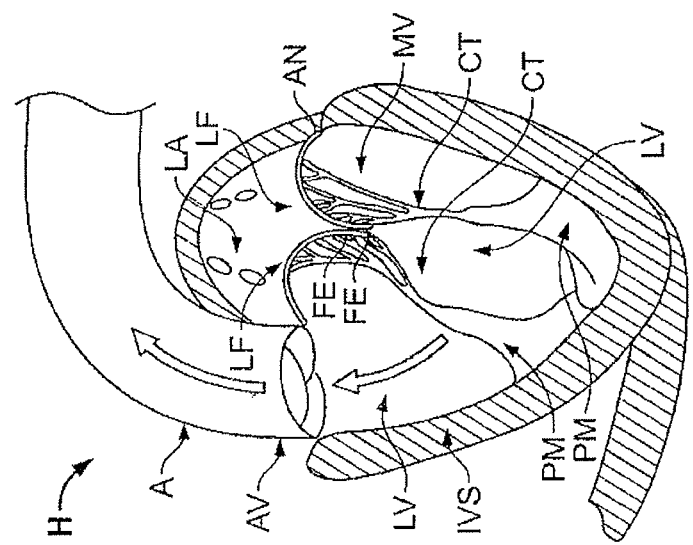
FIG. 1A is a schematic illustration of the left ventricle of a heart showing blood flow during systole with arrows.

The left ventricle LV of a normal heart H in systole is illustrated in FIG. 1A. The left ventricle LV is contracting and blood flows outwardly through the tricuspid (aortic) valve AV in the direction of the arrows. Back flow of blood or "regurgitation" through the mitral valve MV is prevented since the mitral valve is configured as a "check valve" which prevents back flow when pressure in the left ventricle is higher than that in the left atrium LA. The mitral valve MV comprises a pair of leaflets having free edges FE which meet evenly to close, as illustrated in FIG. 1A. The opposite ends of the leaflets LF are attached to the surrounding heart structure along an annular region referred to as the annulus AN. The free edges FE of the leaflets LF are secured to the lower portions of the left ventricle LV through chordae tendineae CT (referred to hereinafter as the chordae) which include plurality of branching tendons secured over the lower surfaces of each of the valve leaflets LF. The chordae CT in turn, are attached to the papillary muscles PM which extend upwardly from the lower portions of the left ventricle and interventricular septum IVS.

While the procedures of the present invention will be most useful with the atrioventricular valves, at least some of the tools described hereinafter may be useful in the repair of other cardiac valves, such as peripheral valves or valves on the venous side of the cardiac circulation, or the aortic valve.

The methods of the present invention can comprise accessing a patient's vasculature at a location remote from the heart, advancing an interventional tool through the vasculature to a ventricle and/or atrium, and engaging the tool against a tissue structure which forms or supports the atrioventricular valve. By engaging the tool against the tissue structure, the tissue structure is modified in a manner that reduces valve leakage or regurgitation during ventricular systole. The tissue structure may be any of one or more of the group consisting of the valve leaflets, chordae, the valve annulus, and the papillary muscles, atrial wall, ventricular wall or adjacent structures. Optionally, the interventional tool will be oriented relative to the atrioventricular valve and/or tissue structure prior to engaging the tool against the tissue structure. The interventional tool may be self-orienting (e.g., pre-shaped) or may include active mechanisms to steer, adjust, or otherwise position the tool.

Alternatively, orientation of the interventional tool may be accomplished in whole or in part using a separate guide catheter, where the guide catheter may be pre-shaped and/or include active steering or other positioning means such as those devices set forth in United States Patent Publication Numbers 2004/0044350, 2004/0092962, and 2004/0087975, all of which are expressly incorporated by reference herein. In all cases, it will usually be desirable to confirm the position prior to engaging the valve leaflets or other tissue structures. Such orienting step may comprise positioning the tool relative to a line of coaptation in the atrioventricular valve, e.g., engaging positioning elements in the valve commissures and confirming the desired location using a variety of imaging means such as magnetic resonant imaging (MRI), intracardiac echocardiography (ICE), transesophageal echo (TEE), fluoroscopy, endoscopy, intravascular ultrasound (IVUS) and the like.

In some embodiments, heart disease in general, and valve repair in particular, are treated by targeting the pacing of the heartbeat. In one embodiment, heart disease is treated by introducing one or more pacing leads into a heart chamber. The pacing leads are placed in contact with a heart muscle and are in electrical communication with a power source. The power source provides paced electrical stimuli to the heart muscle. The electrical stimuli are provided during or immediately after systole to extend systolic contraction of the heart, thereby extending the range of systole during each heartbeat. This extension of systole extends the amount of time in which the heart muscle tightens when it would otherwise be relaxing, when there is most mitral regurgitation in diseased mitral valves.

Other embodiments are directed to annuloplasty to treat heart disease in general and valve repair in particular. In one embodiment, shown generally in FIG. 1B, a stent is used to treat the mitral valve. FIG. 1B shows a cross-sectional view of the heart wherein a flexible stent 100 is positioned at or near the mitral valve MV. The stent 100 is annular and is sized and shaped to be positioned on the annulus of the mitral valve. The stent 100 can transition between a collapsed state of reduced size and an expanded state of enlarged size relative to the collapsed state.

The flexible stent 100 can be percutaneously introduced into an individual's heart while being biased toward the collapsed state. The stent is advanced partially through the annulus of the mitral valve so that it is coaxially positioned within the annulus, as shown in FIG. 1B. The stent 100 is then secured to the annulus such that the stent exerts an inward force on the annulus thereby causing the annulus to resist dilation during diastole of the heart.

In yet another embodiment, a device is disclosed for treating the mitral valve. The device can be a stent, such as the stent 100, that is sized to fit coaxially within an annulus of a mitral valve. The stent includes a hollow frame. The frame can be annular such that it has a cross-sectional diameter that is sized such that an outer surface of the frame is in continuous coaxial contact with the annulus. The frame also includes one or more anchors protruding from it for securing the stent to the annulus. The anchors can be prongs, barbs, protrusions, or any structure adapted to secure the stent to the annulus. The stent is flexible between an expanded configuration and a contracted configuration and is biased toward the contracted configuration so that it exerts an inward force on the annulus.

In one embodiment, the stent 100 is delivered using a delivery catheter 10 that is advanced from the inferior vena cava IVC into the right atrium RA. Once the catheter 10 reaches the anterior side of the interatrial septum IAS, a needle 12 may be advanced so that it penetrates through the septum at the fossa ovalis FO or the foramen ovale into the left atrium LA. At this point, a delivery device can be exchanged for the needle and the delivery device used to deliver the stent 100. The catheter 10 can also approach the heart in other manners.

Figure 2A:
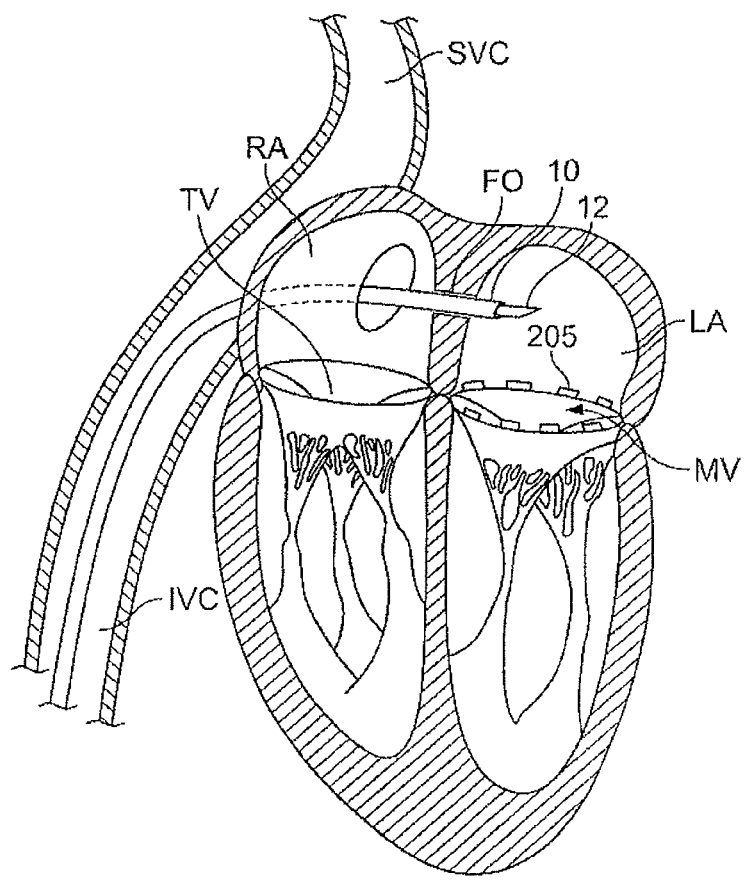
FIG. 2A shows a cross-sectional view of the heart showing one or more magnets positioned around the annulus of the mitral valve.
Figure 2B:
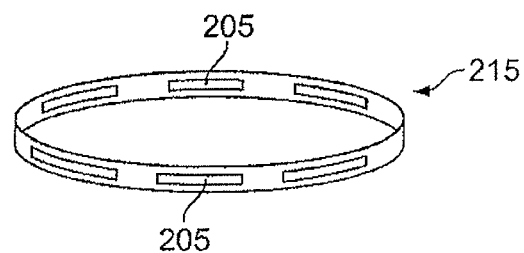
FIG. 2B shows an annular band with magnets that can be positioned on the mitral valve annulus.

FIG. 2A shows a cross-sectional view of the heart showing one or more magnets 205 positioned around the annulus of the mitral valve MV. A corresponding method of treating heart disease involves the use of magnets. The method includes percutaneously introducing at least a first magnet 205 into an individual's heart and securing it to the mitral valve MV annulus. At least a second magnet 205 is percutaneously introduced into the heart and advanced so that it is within a magnetic field of the first magnet. The second magnet is secured to the heart. The polarity of one of the two magnets is then cyclically changed in synchronization with the heart beat so that the magnets attract and repel each other in synchronization with the heart beat. The first magnet therefore moves in relation to the second magnet and exerts an inward closing force on the mitral valve during systole. The magnets 205 can be positioned on an annular band 215 (shown in FIG. 2B) that is sized and shaped to be implanted on the annulus of the mitral valve. The band 215 can be, for example, a stent.

In one embodiment, the magnets 205 or the annular band 215 are delivered using a delivery catheter 10 that is advanced from the inferior vena cava IVC into the right atrium RA, as described above with reference to FIG. 1. Any of the devices described herein can be percutaneously delivered into the heart by coupling the device to a delivery device, such as a steerable delivery catheter.

In yet another embodiment involving magnets, two or more magnets are percutaneously introduced into an individual's coronary sinus such that they attract or repel each other to reshape the coronary sinus and an underlying mitral valve annulus.

Figure 3:
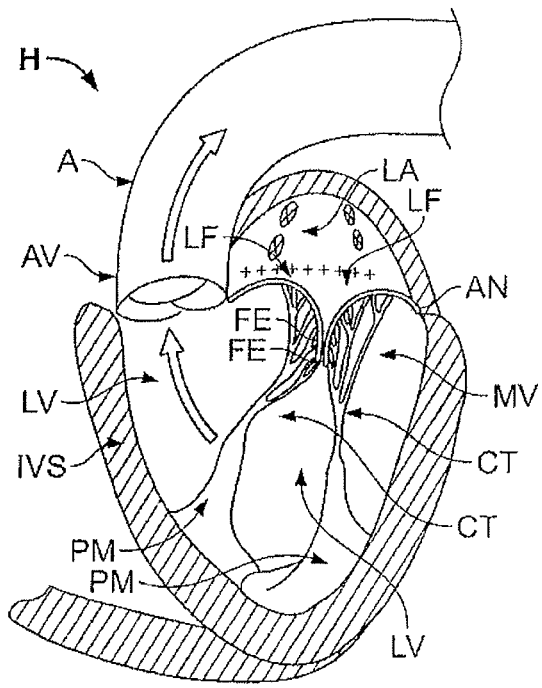
FIG. 3 shows a cross-sectional view of the heart identifying locations for placement of valves.

Other embodiments involve various prosthetics for treating heart disease in general and defective or diseased mitral valves in particular. In one embodiment, a method of treatment includes placing one or more one-way valves in one or more pulmonary veins of an individual either near the ostium of the vein or at some point along the length of the PV. Valves that may be used, for example may be stentless valves such as designs similar to the TORONTO SPV® (Stentless Porcine Valve) valve, mechanical or tissue heart valves or percutaneous heart valves as are known in the art provided they are sized appropriately to fit within the lumen of the pulmonary vein, as shown in FIG. 3. In FIG. 3, the locations in the left atrium LA where valves can be positioned in pulmonary vein orifices are represented by an "X". In addition, certain venous valve devices and techniques may be employed such as those described in U.S. Pat. Nos. 6,299,637 and 6,585,761, and United States Patent Publication Numbers 2004/0215339 and 2005/0273160, the entire contents of which are incorporated herein by reference. A valve prosthesis for placement in the ostia of the pulmonary vein from the left atrium may be in the range of 6-20 mm in diameter. Placement of individual valves in the pulmonary vein ostia (where the pulmonary veins open or take off from the left atrium) may be achieved by obtaining trans septal access to the left atrium with a steerable catheter, positioning a guidewire through the catheter and into the targeted pulmonary vein, and deploying a valve delivery catheter over the guidewire and deploying the valve out of the delivery catheter. The valve may be formed of a deformable material, such as stainless steel, or of a self-expanding material such as NiTi, and include tissue leaflets or leaflets formed of a synthetic material, such as is known in the art. A line of +++++ symbols in FIG. 3 represents a mid-atrial location above the mitral valve where a single valve can be positioned as disclosed later in this specification.

The following references, all of which are expressly incorporated by reference herein, describe devices (such as steerable catheters) and methods for delivering interventional devices to a target location within a body: United States Patent Publication Numbers 2004/0044350, 2004/0092962 and 2004/0087975.

Figure 4:
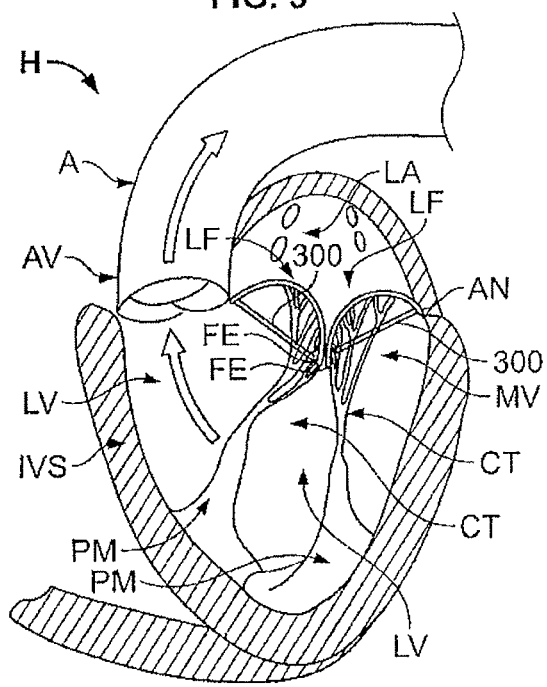
FIG. 4 show a cross-sectional view of the heart with a pair of flaps mounted at or near the mitral valve.
Figure 5A:
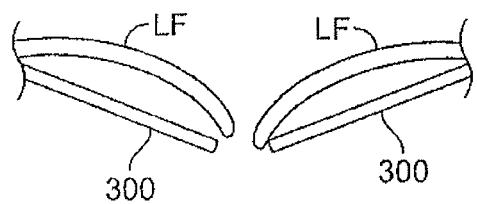
FIG. 5A shows a schematic side view of the mitral valve leaflets with a flap positioned immediately below each leaflet.
Figure 5B:
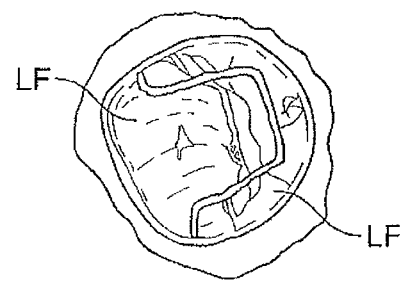
FIG. 5B shows a downward view of the mitral valve with a pair of exemplary flaps superimposed over the leaflets.
Figure 5C:
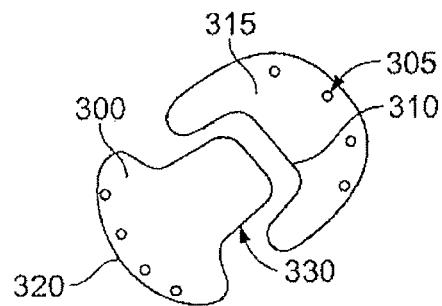
FIG. 5C shows a pair of mitral valve leaflet flaps having complementary shapes.

FIG. 4 show a cross-sectional view of the heart with a pair of flaps mounted at or near the mitral valve. FIG. 5A shows a schematic side view of the mitral valve leaflets LF with a flap 300 positioned immediately below each leaflet. The flap 300 can be contoured so as to conform at least approximately to the shape of a leaflet, or the flap 300 can be straight as shown in FIG. 4. FIG. 5B shows a downward view of the mitral valve with a pair of exemplary flaps superimposed over the leaflets LF. As shown in FIG. 5C, the flaps can have complementary shapes with a first flap having a protrusion that mates with a corresponding recess in a second flap.

In corresponding method of treatment, shown in FIGS. 4 and 5C, a first flap 300 with an attachment end 305 and a free end 310 is provided. The attachment end 305 of the first flap 300 is secured to the inside wall of the ventricle below the mitral valve. A second flap 315 with an attachment end 320 and a free end 330 is provided and is also secured to the inside wall of the ventricle below the mitral valve. The first and second flaps 300, 315 are oriented so that they face each other and the free ends 310, 330 are biased toward each other and approximate against each other during systole. This system provides a redundant valving system to assist the function of the native mitral valve.

Figure 6A:
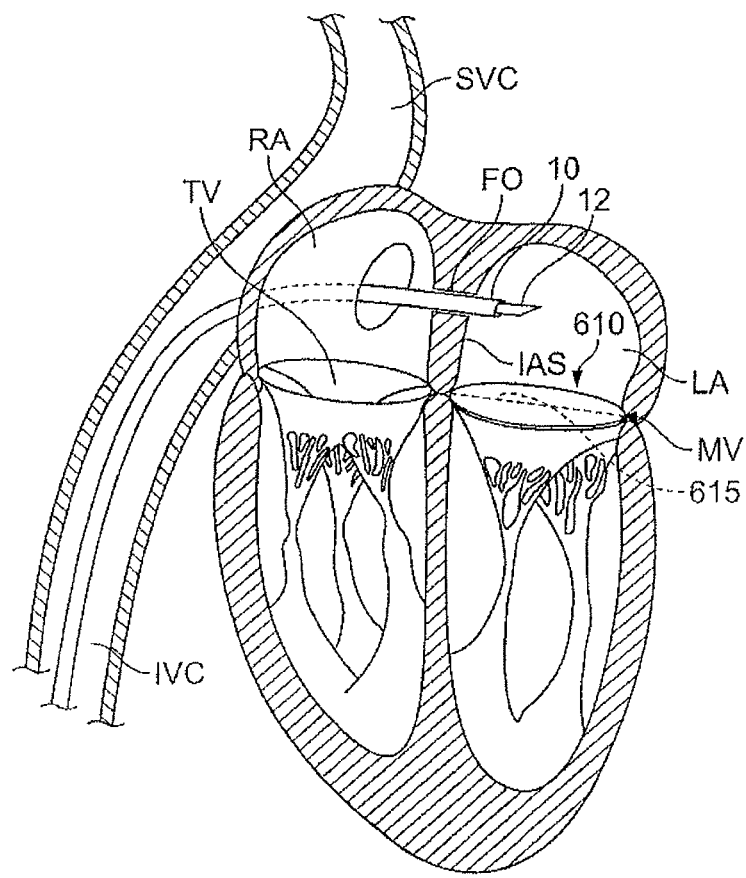
FIG. 6A shows a cross-sectional view of the heart with a membrane ring positioned at the mitral valve annulus.
Figure 6B:
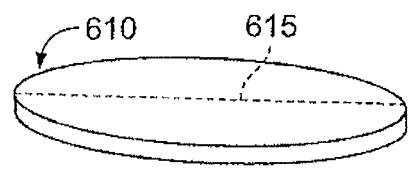
FIG. 6B shows a schematic view of the membrane ring, which includes an annular ring on which is mounted a membrane.

In other embodiments, devices and methods that involve prosthetic discs are disclosed. For example, FIG. 6A shows a cross-sectional view of the heart with a membrane ring 610 positioned at the mitral valve annulus. FIG. 6B shows a schematic view of the membrane ring 610, which includes an annular ring on which is mounted a membrane. The membrane includes a series of perforations 615 extending through the membrane surface. One or more anchor devices, such as prongs, can be located on the ring for securing the ring to the mitral valve.

In one embodiment, a device for treating heart disease in general and defective or diseased mitral valves in particular includes a disc having a ring, a membrane stretched across an opening of the ring, and one or more anchors for securing the disc to an annulus of a mitral valve. The disc is sized to cover the annulus of the mitral valve, and the membrane includes one or more perforations that permit one way fluid flow through the disc. Methods of treatment using the device are also provided.

In other embodiments, devices and methods that involve fluid-filled bladders are disclosed. FIG. 7A shows a cross-sectional view of a heart with a bladder device positioned partially within the left ventricle and partially within the left atrium. A device for treating heart disease in general and defective or diseased mitral valves in particular includes a fluid-filled bladder 600. The bladder 600 is placed across the mitral valve between the left atrium and the left ventricle. Upon compression of the left ventricle, the volume of the bladder is expanded on the left atrial side of the heart, providing a baffle or sealing volume to which the leaflets of the mitral valve coapt. The bladder may also act as a blocking device in the case of flail of a leaflet, blocking said flailing leaflet from billowing into the left atrium causing regurgitation. The bladder also includes one or more anchors for securing the bladder to an annulus of a mitral valve, or may be formed on a cage or other infrastructure to position it within the line of coaptation of the mitral valve.

A bladder can also be used to treat functional mitral valve disease. As mentioned, functional mitral valve disease is usually characterized by the failure of the mitral valve leaflets to coapt due to an enlarged ventricle, or other impediment to the leaflets rising up far enough toward each other to close the gap or seal against each other during systole. FIG. 7B shows a schematic side view of the mitral valve leaflets LF failing to coapt such that regurgitation can occur (as represented by the arrow RF.) With reference to FIG. 7C, a baffle or bladder 630 is positioned between the leaflets LF along the line of coaptation of the leaflets. The bladder 630 provides a surface against which at least a portion of the leaflets LF can seal against. The bladder 630 thus serves as a coaptation device for the leaflets. The bladder can be attached to various locations adjacent to or on the mitral valve. FIG. 7D shows a plan view of the mitral valve with the leaflets LF in an abnormal closure state such that a gap G is present between the leaflets. In one embodiment, the bladder is attached or anchored to the mitral valve at opposite edges E of the gap G.

Methods of treatment using the bladder include providing the bladder and inserting it through an annulus of a mitral valve such that the bladder is coaxially positioned through the mitral valve. An atrial portion of the bladder extends into the left atrium, and a ventricular portion of the bladder extends into the left ventricle. A mid portion of the bladder may be secured to the annulus of the mitral valve such that the mid portion remains stationery while the atrial and ventricular portions expand and contract passively between the atrium and ventricle based on pressure differentials during systole and diastole.

Figure 8:
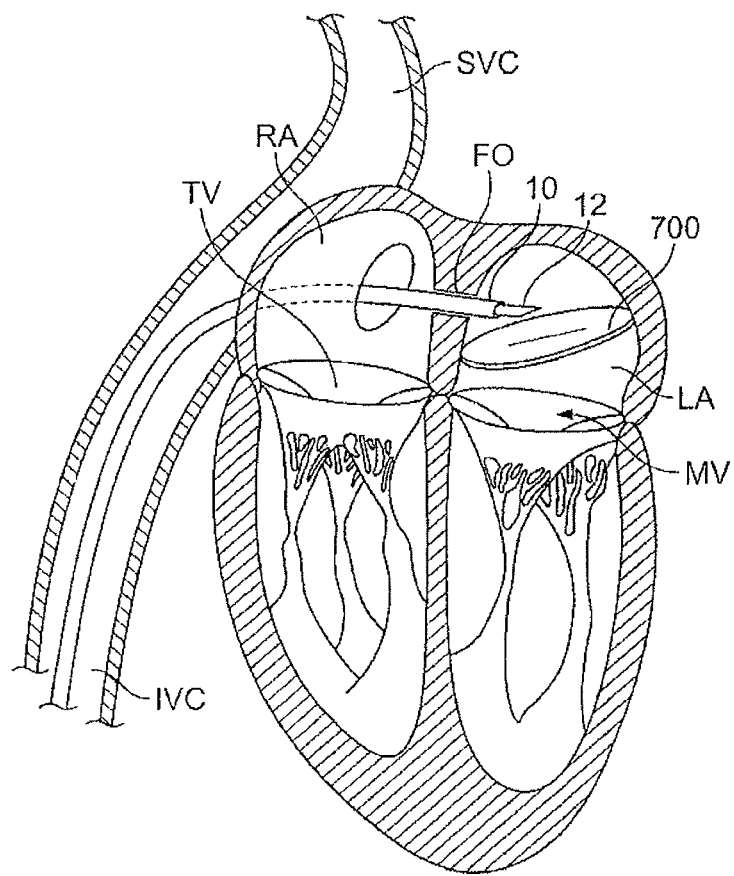
FIG. 8 shows a cross-sectional view of the heart wherein a one-way valve device is located in the left atrium.

FIG. 8 shows a cross-sectional view of the heart wherein a one-way valve device 700 is located in the left atrium. The valve device is represented schematically in FIG. 8. A corresponding method of treating heart disease includes introducing a one-way valve device 700 into the left atrium of an individual's heart proximal the mitral valve. The valve device 700 is configured to permit fluid flow in one direction while preventing fluid flow in an opposite direction. The valve device can have various structures. For example, the device can comprise a valve that is mounted on a stent that is sized to be positioned in the left atrium. Valves that may be used, for example may be stentless valves such as the TORONTO SPV® (Stentless Porcine Valve) valve, mechanical or tissue heart valves or percutaneous heart valves as are known in the art. The outer wall of the one-way valve device is sealed to the inner wall of the atrium so that a fluid-tight seal is formed between the outer wall of the one-way valve device and the inner wall of the left atrium. In this regard, the valve device can include a seal member that is configured to seal to the inner wall of the atrium.

Figure 9A:
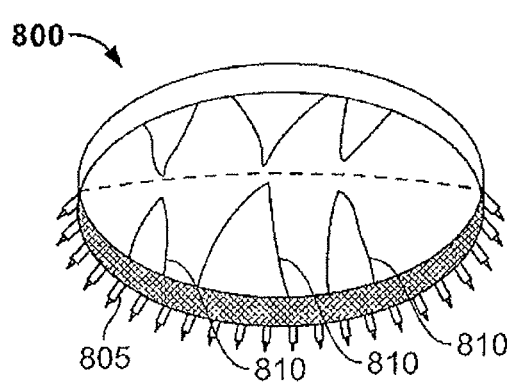
FIG. 9A shows a prosthetic ring that is sized to fit within a mitral valve.
Figure 9B:
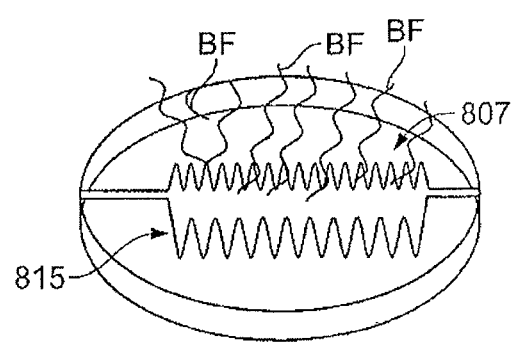
FIG. 9B shows another embodiment of a prosthetic ring wherein a one-way valve is positioned inside the ring.

Another embodiment involves a prosthetic for treating heart disease in general and defective or diseased mitral valves in particular. FIG. 9A shows a prosthetic ring 800 that is sized to fit within a mitral valve annulus The ring includes one or more anchors 805 that extend around the periphery of the ring 800. In addition, one or more struts 810 struts extend across the diameter of the ring, and can be made of a material that includes Nitinol or magnetic wires for selectively adjusting the shape of the ring. The struts can also be instrumental in baffling mitral valve leaflet "flail". FIG. 9B shows another embodiment of a prosthetic ring 807 wherein a one-way valve 815 is positioned inside the ring such that blood flow BF can flow through the valve in only one direction. The valve can be manufactured of various materials, such as silicone.

Figure 10:
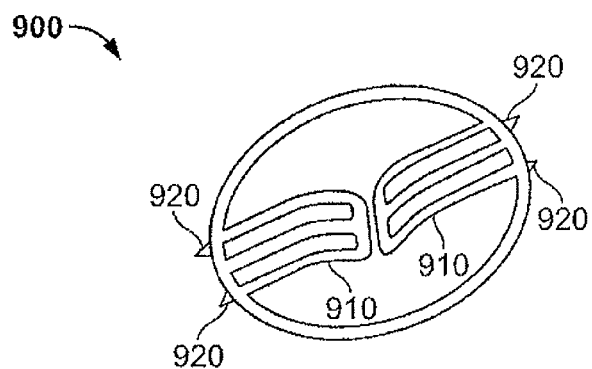
FIG. 10 shows a prosthetic with one or more tongues or flaps that are configured to be positioned adjacent the flaps of the mitral valve.

FIG. 10 shows a prosthetic with one or more tongues or flaps that are configured to be positioned adjacent the flaps of the mitral valve. The prosthetic includes a ring 900 sized to fit within a mitral valve annulus. At least two tongues 910 project from the ring 900 in a caudal direction when the ring is implanted into a heart of an individual. The ring is flexible between an expanded configuration and a contracted configuration and is biased toward the contracted configuration. One or more anchors 920 protrude from the flexible ring for coupling the ring coaxially to the annulus such that the contracted configuration of the ring exerts an inward force to the annulus. Alternatively, or in addition, the two tongues can each have a length sufficient to prevent prolapse of a mitral valve when the ring is placed atop the leaflets of the mitral valve. In a further embodiment the tongue elements may be attached at a central point.

In yet another embodiment, a prosthetic for treating heart disease in general and a defective or diseased mitral valve in particular includes a wedge. The wedge has a length that is about equal to a length of the line of coaptation of a mitral valve. The wedge has a depth sufficient to prevent prolapse of a mitral valve when the wedge is placed atop an annulus of the mitral valve along the line of coaptation, and may provide a point of coaptation for each leaflet. One or more anchors protrude from the wedge for coupling the wedge to the annulus of the mitral valve. Methods of treatment using the wedge are also disclosed. The methods include inserting the wedge into an individual's heart, placing the wedge lengthwise along the line of coaptation of the mitral valve. The wedge is then secured to an annulus of the mitral valve along the line of coaptation. The wedge may be positioned also just under one segment of the leaflet (likely P2 in the case of functional MR).

Figure 11A:
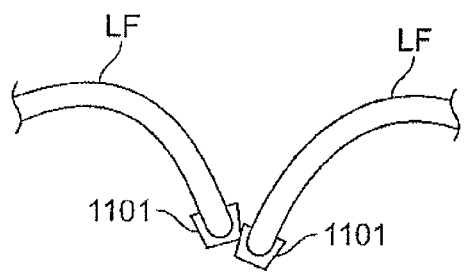
FIG. 11A shows an exemplary embodiment of one or more clips that are positioned on free edges of the leaflets.

In yet another embodiment, a device for treating heart disease includes a clip for attachment to a free end of a heart valve leaflet. FIG. 11A shows an exemplary embodiment of one or more clips 1101 that are positioned on free edges of the leaflets LF. Each of the clips 1101 has a shape that prevents flail of the leaflet by catching against an underside of an opposing leaflet. Methods of treatment using the clip are also disclosed. The methods include introducing the clip into an individual's heart and attaching the clip to a free end of a heart valve leaflet opposite the free end of an opposing leaflet of the heart valve so that the clip catches to the underside of the opposing leaflet during systole. In a further embodiment, a clip may be placed on both leaflets such that the clips meet or catch when the leaflets are in proximity. The clips may attach momentarily during systole, and then detach during diastole, or may clip permanently resulting in a double orifice mitral valve anatomy. The clips of this embodiment may include a magnetic element, or one may be magnetic and the other of a metal material attracted to said electromagnetic field of the magnetic clip.

Figure 11B:
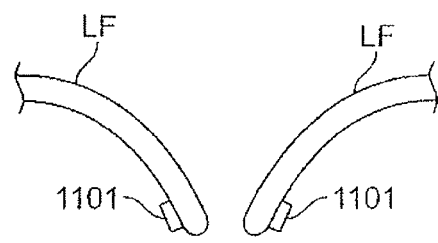
FIG. 11B shows pair of leaflets with a magnetic clip attached to the underside of each leaflet.
Figure 11C:
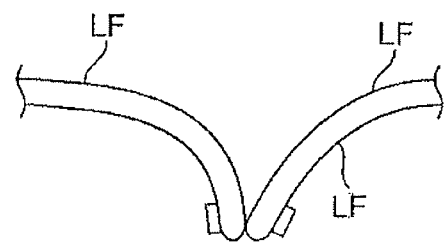
FIG. 11C shows the leaflets coapted as a result of the magnetic attraction between the magnetic clips.

In the case of magnetic clips, the clip elements may be placed on the underside of the leaflets (e.g. not necessarily on the free edge of the leaflet), provided that the magnetic field of the clip is sufficient to attract the opposing magnetic or metal clip element. This is further described with reference to FIG. 11B, which shows pair of leaflets LF with a clip 1101 attached to the underside of each leaflet. At least one of the clips is magnetic, while the other clip is of an opposite magnetic polarity than the first clip or of a metal attracted to the magnetic field of the first clip. The magnetic field is sufficiently strong such that the clips 1101 can attach to one another either momentarily or permanently to coapt the leaflets, as shown in FIG. 11C.

Figure 11D:
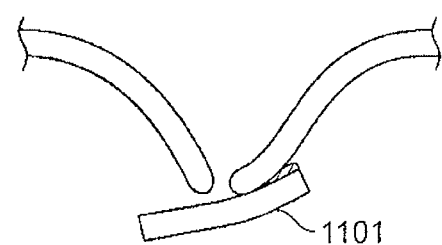
FIG. 11D shows a pair of leaflets with a single clip attached to one of the leaflets.

In another embodiment, shown in FIG. 11D, a single clip 1101 is attached to one of the leaflets. The clip 1101 is sufficiently long to increase the likelihood that the clip 1101 will coapt with the opposite leaflet.

Figure 12:
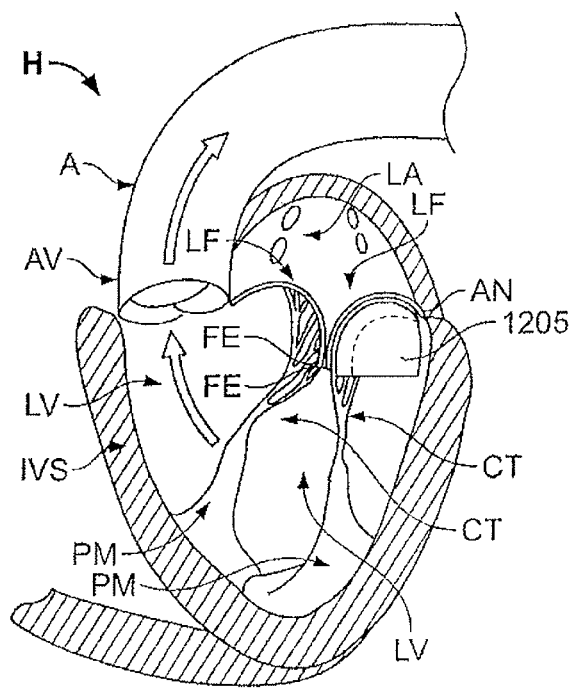
FIG. 12 shows a schematic, cross-sectional view of the heart with a wedge positioned below at least one of the leaflets of the mitral valve.

In yet another embodiment, a device for treating heart disease includes a wedge for placement under a heart valve leaflet. FIG. 12 shows a schematic, cross-sectional view of the heart with a wedge 1205 positioned below at least one of the leaflets of the mitral valve. The wedge 1205 can be positioned below one or both of the leaflets. The wedge 1205 is sized to fit under the valve leaflet and caudal the annulus of the heart valve. The wedge 1205 can have a shape that is contoured so as to provide support to a lower surface of the leaflet. (In FIG. 12, the left atrium is labeled LA and the left ventricle is labeled LV.) An anchor is attached to the wedge for coupling the wedge to a wall of the heart chamber adjacent the heart valve. The wedge forms a fixed backstop against the bottom side of the heart valve leaflet, thereby providing a location for the leaflet to coapt against, and/or providing support or "pushing up" a restricted leaflet.

Other embodiments are directed to altering the size, shape, chemistry, stiffness, or other physical attributes of heart valve leaflets. In one embodiment in particular, a method of treating heart disease includes obtaining access to a heart valve leaflet and injecting a stiffening agent into the leaflet to stiffen the leaflet and minimize flail.

Other embodiments are directed to the chordae that connect heart valve leaflets to the inner walls of the heart. In one embodiment in particular, a method of treating heart disease includes obtaining access to a heart valve chord and cutting it mechanically or with energy such as a laser, or by heating the chordae to elongate them, thereby allowing the previously restricted leaflet to be less restricted so that it can coapt with the opposing leaflet.

In another embodiment directed to the chordae that connect heart valve leaflets to the inner walls of the heart, a cam-shaped ring is disclosed. The cam-shaped ring is sized to fit within a left ventricle of a heart. The ring forms a hole that is sized to receive two or more chordae tendineae. The ring is formed by connecting two detachable ends of the ring.

Methods of treatment using the cam-shaped ring are also disclosed. One method in particular includes introducing the ring into a left ventricle of a heart. One or more chordae tendineae are then surrounded by the ring, and the two ends of the ring are then attached to form a closed ring around the chordae tendineae. The ring is then rotated such that one or more of the chordae tendineae are shifted away from their initial orientation by the rotation of the cam-shaped ring. The ring may then be fixed in the rotated or tightened position.

Figure 13A:
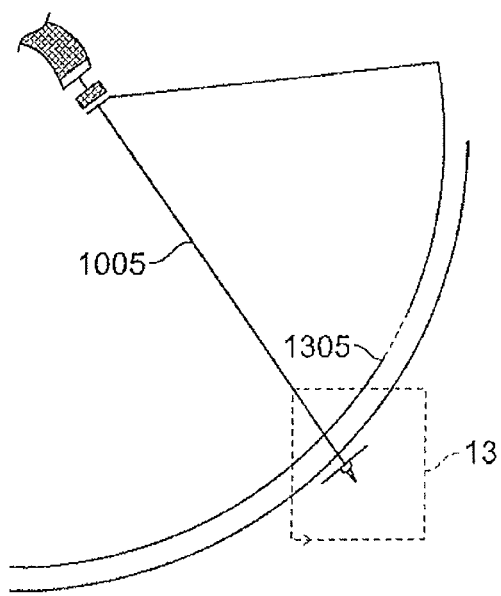
FIG. 13A shows an artificial chordae tendon.

An embodiment directed at the chordae of heart valve leaflets is now described. FIG. 13A shows a device that can be used to alter a chordae. A method includes obtaining access to a chordae tendinea (chord) within an individual's heart chamber. The chordae is then cut at a point along its length so that a length of the chordae tendinea is freed from the heart chamber leaving behind a length of chordae tendinea having a free end and an end attached to an edge of a heart valve.

With reference to FIG. 13A, a synthetic chord 1005 of greater length than the free length of chordae is introduced into the heart chamber. One end of the synthetic chordae 1005 is connected to a wall 1305 of the heart chamber or to a muscle attached to the wall of the heart chamber. Another end of the synthetic chord is attached to the free end of the chorda tendinea or to the leaflet.

Figure 13B:
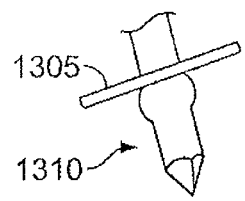
FIGS. 13B and 13C show attachment devices for attaching the artificial chordae tendon to a heart wall.
Figure 13C:
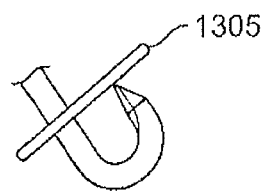

In this regard, the end of the chord 1005 that is attached the wall 1305 can have any of a variety of devices that facilitate such attachment. FIGS. 13B and 13C show enlarged views of attachment devices contained within box 13 of FIG. 13A. The attachment devices can be used to attach the chord 1005 to the wall 1305. In FIG. 13B, the attachment device 1310 is an enlarged ball having a distal trocar for penetrating the wall 1305. In FIG. 13C, the attachment device 1310 is a hook that is configured to penetrate through the wall 1305. It should be appreciated that the attachment device 1310 can have other structures and it not limited to the structures shown in FIGS. 13B and 13C. In variations of these embodiments, it may be advantageous to adjust the length of the chordae (synthetic, or modified), determine the therapeutic effect of the shortening or lengthening, and then fix the chordae at the most efficacious location.

Valve regurgitation due to flail or broken chordae can occur. Such valve impairments can be treated percutaneously through chordal replacement or the supplementing of the chordae tendineae of the mitral valve. Although the embodiments described herein are with reference to treating mitral valve impairments it should be appreciated that other valves could similarly be treated with the embodiments described herein. The configuration of the chordal replacement devices described herein can vary. Features of the various devices and their anchoring systems can be used in combination with any of the embodiments described herein.

The chordal replacement devices described herein can be delivered using interventional tools, guides and supporting catheters and other equipment introduced to the heart chambers from the patient's arterial or venous vasculature remote from the heart. The chordal replacement devices described herein can be compressed to a low profile for minimally-invasive or percutaneous delivery. They can be advanced from the remote access site through the vasculature until they reach the heart. For example, the chordal replacement devices can be advanced from a venous site such as the femoral vein, jugular vein, or another portion of the patient's vasculature. It is also appreciated that chordal replacement devices can be inserted directly into the body through a chest incision. A guidewire can be steered from a remote site through the patient's vasculature into the inferior vena cava (IVC) through the right atrium so that the guidewire pierces the interatrial septum. The guidewire can then extend across the left atrium and then downward through the mitral valve MV to the left ventricle. After the guidewire is appropriately positioned, a catheter can be passed over the guidewire and used for delivery of a chordal replacement device.

Embodiments of the chordal replacement devices described herein can also be delivered using a catheter advanced through retrograde access through, for example an artery, across the aortic arch and the aortic valve and to the mitral valve by way of the ventricle. Alternative delivery methods of chordal replacement device embodiments described herein can include inserting the device through a small access port such as a mini-thoracotomy in the chest wall and into the left ventricle apex. From there, the chordal replacement device can be advanced through the left ventricle into the left atrium. It should be appreciated the device can also be delivered via the left atrial apex as well. Positioning of the tool and/or chordal replacement devices described herein can be confirmed using a variety of imaging means such as magnetic resonant imaging (MRI), intracardiac echocardiography (ICE), transesophageal echo (TEE), fluoroscopy, endoscopy, intravascular ultrasound (IVUS) and the like.

Figure 38A:
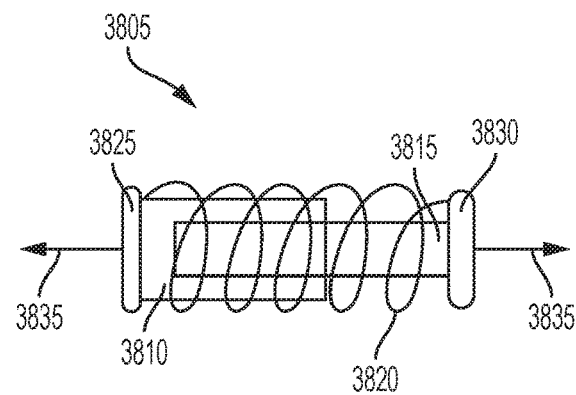
FIGS. 38A-38C show an embodiment of a chordal replacement device.
Figure 38B:
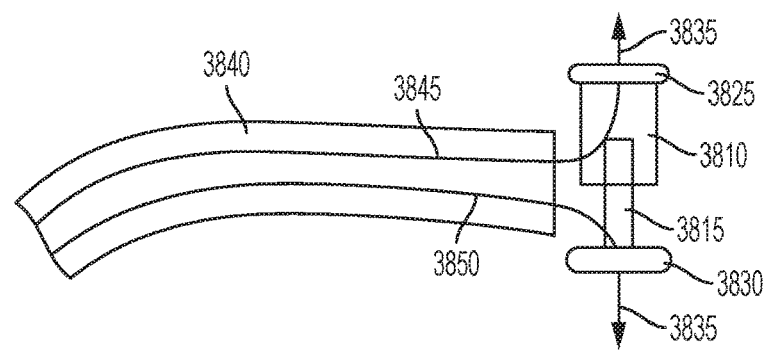
Figure 38C:
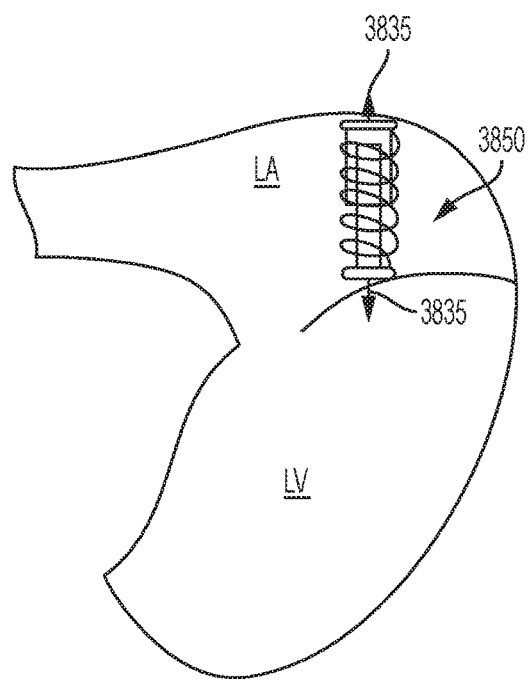

In an embodiment and as shown in FIGS. 38A-38C, a chordal replacement device 3805 can include a laterally-stabilized spring or flexible rod. In one embodiment, the device 3805 can include a first portion 3810 that receives and/or is movable with respect to a second portion 3815. The first and second portions 3810, 3815 can be surrounded by a spring 3820. Each of the first and second portions 3810, 3815 of the device 3805 can have a platform region 3825, 3830, respectively between which the spring 3820 extends. The platform regions 3825, 3830 can be of sufficient surface area or diameter that they can push against the heart wall and the leaflet surface without damaging or puncturing the surfaces. In an embodiment, the platform regions 3825, 3830 can also each have one or more barbs 3835 or another fixation device on an external surface that can implant and attach the device 3805 between the valve leaflet and the roof of the atrium (see FIG. 38C). It should also be appreciated that other attachment mechanisms for attaching one or more of the platform sections to the valve leaflet and/or the roof of the atrium are possible and that the device is not limited to including barbs. For example, one or more of the platforms can include clips such as a clip similar to the Mitraclip® to grasp the leaflet, and an adhesive or screw to attach to the roof of the atrium.

The chordal replacement device 3805 can be delivered into the left atrium through a guide catheter 3840 (see FIG. 38B). A tether 3845 can hold the device 3805 normal to the tip of the guide catheter 3840. The tether 3845 can be threaded through the guide catheter 3840, through the implant 3805, and back out the guide catheter 3840. When the procedure is completed, the tether 3845 can be pulled out of the guide catheter 3840 from either end releasing the implant, allowing deployment. Other mechanisms of attachment to the implant 3805 are considered herein. For example, the tether 3845 can be replaced by a flexible rod having, for example threads at a distal end. The threads of the rod can attach to corresponding threads on the implant 3805. The threaded region of the implant can be rotatable such that the implant 3805 can rotate perpendicular to the guide catheter 3840 (see the position shown in FIG. 38B) in order to couple and uncouple with the rod through rotational threading and unthreading.

As shown in FIG. 38B, a second tether 3850 can be used to longitudinally compress the spring 3820 between the platforms 3825, 3830 such that they approximate one another and the first portion 3810 receives a greater length of the second portion 3815 than it receives in the uncompressed state and the overall length of the device 3805 is reduced as defined by the distance between the barbs. This second tether 3850 can thread through the guide catheter 3840 in a similar manner as the first tether 3845 as described above. The second tether 3850 can be tensioned to compress the spring 3820 and after removal can be withdrawn similarly as the first tether 3845. In an embodiment, a barb 3835 can be planted into a portion of the flailing valve leaflet and another barb 3835 can be planted into the roof of the left atrium LA. The barbs can be planted by actuating the distal curved section of the guide catheter so as to guide the barbs 3835 into the desired locations.

The device 3805 can exert a force between the atrium roof and the valve leaflet through the spring 3820 to hold the leaflet down and prevent flail up into the left atrium LA. The tension can be adjusted by varying the spring coupled to the device prior to inserting it into the body. Alternatively, the desired length of the device after implantation can be adjusted and tuned prior to introduction with an adjustable bolt and nut type design that limits how far one platform can move in relation to the other. It should be appreciated that the embodiments of chordal replacement devices described herein are exemplary and that variations are possible.

Figure 39A:
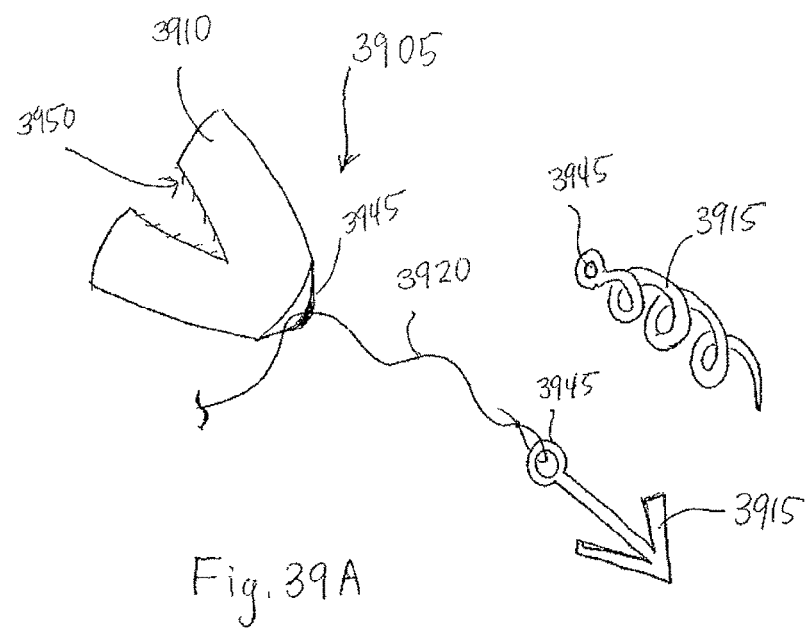

In another embodiment shown in FIGS. 39A-39O, a chordal replacement device 3905 can include a clip 3910, a distal anchor 3915 and a tether 3920 extending therebetween. The clip 3910 can attach to a portion of a flailing leaflet LF and the distal anchor 3915 can extend into the ventricle such that the flailing leaflet is held down. For example, the anchor 3915 can be implanted in the left ventricular wall or septum or papillary head or other appropriate tissue site. The length of the tether 3920 can be variable and/or adjusted such that the tension applied to the leaflet LF by the chordal replacement device 3905 is tailored to an individual patient's needs. For example, once the clip 3910 is positioned, the tether 3920 can be tensioned, tied and trimmed as will be described in more detail below.

The clip 3910 can be an elastic element that can be deformed to attach it to a portion of the leaflet LF, such as by crimping. In an embodiment, the clip 3910 can be attached to a portion of the valve leaflet LF where flail occurs, for example it can be fastened to an edge of the anterior or posterior mitral valve leaflet with the damaged chord. The clip 3910 can have surface feature 3950, such as small barbs or a textured surface, that aids in the capture of the leaflet LF upon deforming the clip 3910 to the leaflet LF. As best shown in FIG. 39A, the clip 3910 can also include an eyelet, aperture or other attachment feature 3945 that provides a location for coupling to or extending the tether 3920 through a portion of the clip 3910. The distal anchor 3915 can similarly include an eyelet, aperture or attachment feature 3945 that provides a location for the tether 3920 to couple to or extend through a portion of the anchor 3915 (see FIG. 39A, for example).

Figure 39B:
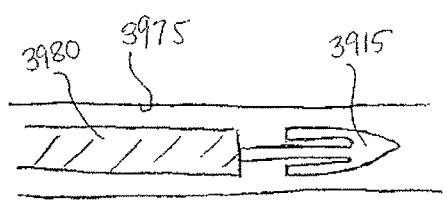
Figure 39C:
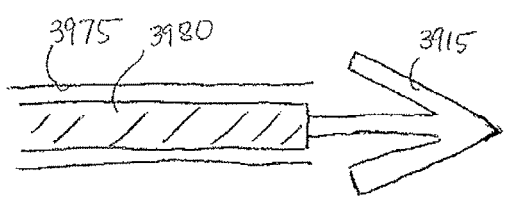
Figure 39I:
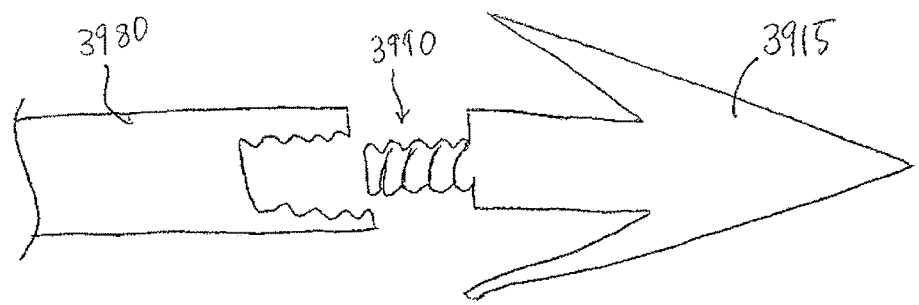
Figure 39J:
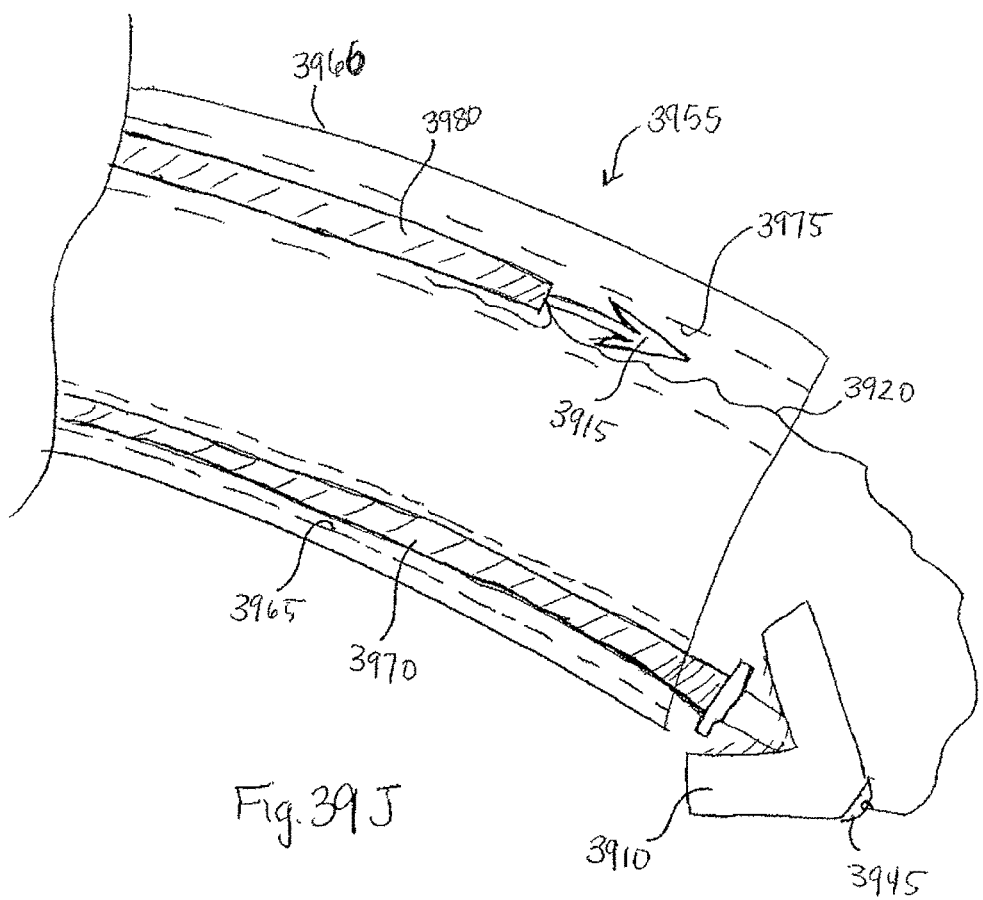
Figure 39K:
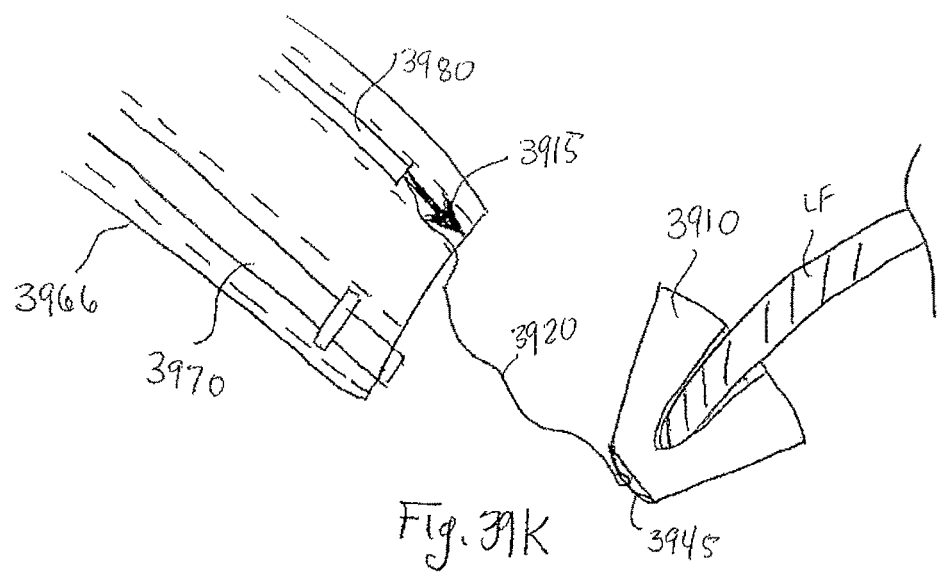

The anchor 3915 can vary in configuration and can include a weight, barb, corkscrew, adhesive or other mechanism such that the tether 3920 extends down and is secured in place within the ventricle. In an embodiment, the anchor 3915 extends into the ventricle from the clip 3910 and is secured to the bottom of the ventricle or toward the ventricular septum or papillary head. In an embodiment, the barbs of the anchor 3915 can be collapsible such that they conform to a narrow configuration and fit within the lumen of the guide catheter and expand upon being advanced out of the guide catheter (see FIGS. 39B-39C).

As mentioned above, the tether 3920 can attach to the clip 3910 in a variety of ways. The clip 3910 can include an attachment feature 3945 that provides a location for coupling the clip 3910 to the tether 3920. For example and as shown in FIG. 39D-39H, a knot or crimp 3930 can be applied to one end of the tether 3920 such that end will lodge into a portion of the clip 3910 or will lodge into the attachment feature 3945. The opposite, unknotted end of the tether 3920 can extend through the delivery catheter 3960 and be retracted until the crimp 3930 lodges with the attachment feature 3945 on the clip 3910, which is attached to the leaflet LF. The delivery catheter 3960 can be used to deploy the clip 3910 to the leaflet (FIG. 39E) and can then be withdrawn (FIG. 39F). At this stage the tether 3920 can still have both ends extending outside the body (FIG. 39G). An anchor 3915 also coupled to the tether 3920 can be loaded over the tether 3920 and delivered to the ventricle as will be described in more detail below.

In another embodiment shown in FIG. 39J-39M, the delivery system 3955 for the chordal replacement device 3905 can include a guide catheter 3966 having a lumen 3965 for a clip delivery catheter 3970 and a lumen 3975 for an anchor pusher or mandrel 3980 used to push the anchor 3915 out of the delivery system 3955. The anchor 3915 is shown as a barbed anchor, but it should be appreciated that other configurations are considered herein. The anchor 3915 can be attached to a distal end of the mandrel 3980 such as by corresponding threads 3990 or another coupling mechanism. Upon being pushed out the distal end of the guide catheter 3966, the anchor 3915 can be uncoupled from the mandrel 3980 (such as by an unthreading rotation) and released in its position within the heart. Alternatively, the anchor 3915 can be unattached to the mandrel 3980 and simply pushed out the distal end of the guide catheter 3966. Once the anchor 3915 is implanted, the mandrel 3980 can be withdrawn.

Figure 39L:
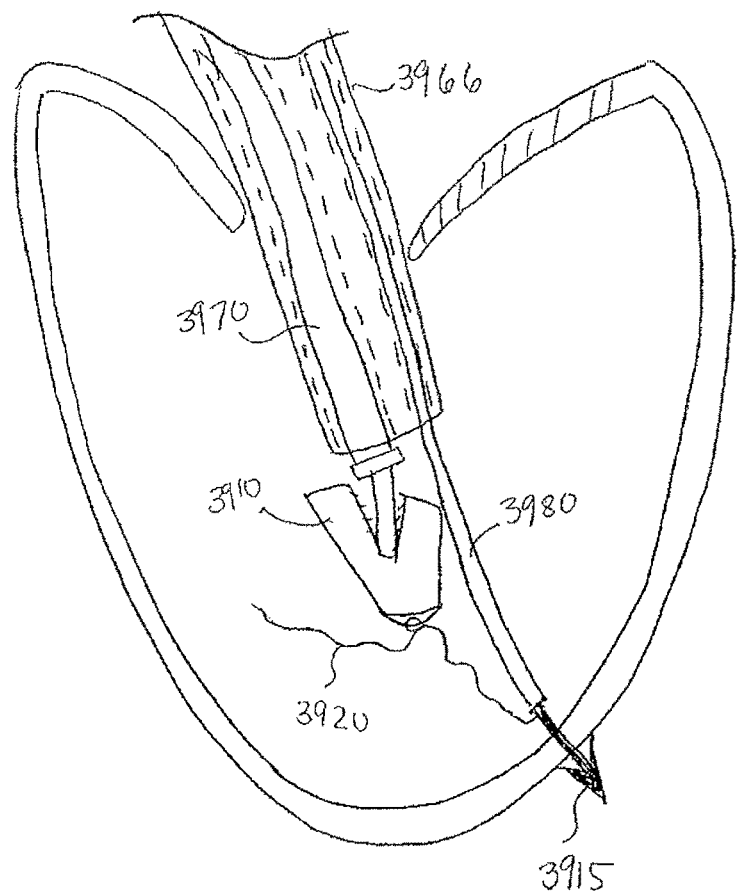
Figure 39M:
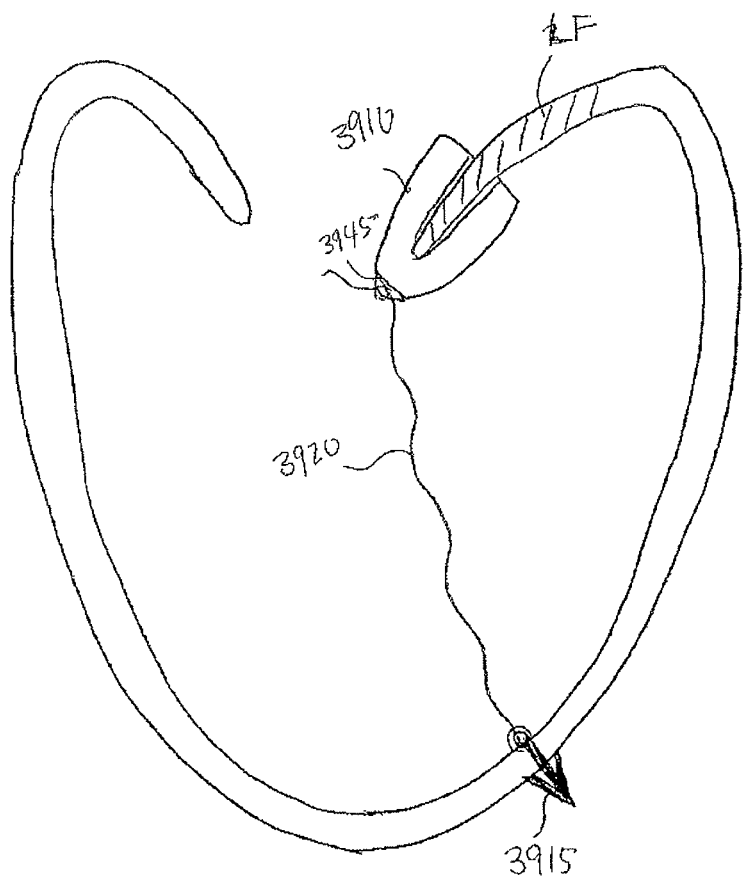

It should be appreciated that the clip 3910 can be deployed prior to, during or after delivery of the anchor 3915. The embodiments of FIGS. 39D-39H and FIG. 39K illustrate the deployment of the clip 3910 prior to the anchor 3915 being delivered. FIGS. 39L-39M illustrate an embodiment in which the clip 3910 is deployed after the anchor 3915 is delivered.

As mentioned above, once the clip 3910 is positioned on the leaflet LF and the anchor 3915 deployed and secured within the ventricle, the tether 3920 can be tensioned. For example, the tether 3920 can be pulled manually to tension an end of the tether 3920 extending outside the body, to the desired tension to hold the leaflet LF down. Tension on the tether 3920 can be tuned and adjusted until an appropriate tension on the leaflet LF is achieved evidenced by the tether 3920 simulating the tension of a healthy chord. The appropriate tension can be assessed as is known in the art. For example, an echocardiogram can be performed to assess leaflet flail or prolapse as well as the effect on mitral regurgitation. Once the appropriate tension is achieved, the tether 3920 can be clamped and cut to remove the excess length of the tether 3920. FIGS. 39N-39O illustrate an embodiment of a dual-function cutting clamp 3935 having the tether 3920 extending therethrough. The cutting clamp 3935 can have dual functions and can be used to clamp onto the tether 3920 to secure it near the distal end and it can also be used to cut the tether 3920 proximal of the secured section. As best shown in FIG. 39O, the cutting clamp 3935 can have an outer shell 3937 that can be coupled or attached to the anchor 3915. The shell 3937 of the cutting clamp 3935 can have apertures or slots 3939 at opposite ends through which the tether 3920 can extend into an inner region of the shell 3937. From one end of the shell 3937, the tether 3920 extends towards the clip 3910. At the opposite end of the shell 3937, the tether 3920 extends back through the delivery catheter 3970 to the outside of the body. The cutting clamp 3935 can also include an aperture or slot 3941 through which an actuator line 3943 can pass and extend to the outside of the body. The actuator line 3943 can be actuated to effect clamping and/or cutting of the tether 3920 with the cutting clamp 3935.

Still will respect to FIG. 39O, the cutting clamp 3935, which may or may not already be coupled to the anchor 3915 can be actuated such that the tether 3920 is engaged by a ratcheting clamp mechanism. The ratcheting clamp mechanism prevents the release of the tension on the tether 3920. The ratcheting clamp mechanism can include opposing clamp elements 3946 that extend inward from a ratchet recess 3947 open at an inner surface of the shell 3937. The opposing clamp elements 3946 have textured surfaces at one end that are designed to come together to releasably engage the tether 3920. At an opposite end the opposing clamp elements 3946 can have a ratchet mechanism 3949 that engages corresponding features in the ratchet recess 3947 of the shell 3937. The opposing clamp elements 3946 can be actuated by pulling the actuator line 3943 at the outside of the body. The actuator line 3943 engages the opposing clamp elements 3946 such that they extend out from the ratchet recess 3947 and approach one another until the tether 3920 is caught between their textured surfaces. After the opposing clamp elements 3946 are engaged with one another and the tension on the tether 3920 is maintained, the actuation line 3943 can be actuated further until the opposing cutting elements 3951 are engaged by the actuation line 3943, extend from their respective ratchet recess 3947 until their cutting surfaces come in contact to cut the tether 3920 therebetween. Once the tether 3920 is cut by the opposing cutting elements 3951 the actuation line 3943 can be released and the loose end of the tether 3920 can be removed from outside the body. In an embodiment, multiple chordal replacement devices 3905 can be used to attach to the chordae on the opposite or same side as the flailing leaflet. The second chordal replacement device 3905 can incorporate a similar cutting clamp as described above.

Figure 40A:
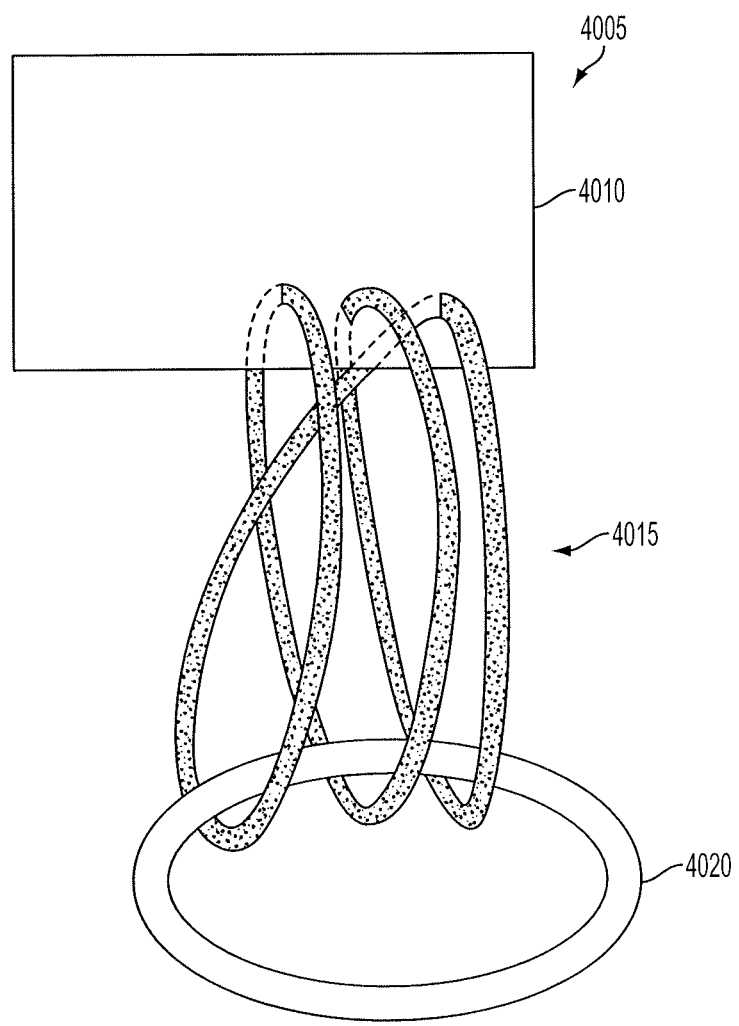
FIGS. 40A-40B show another embodiment of a chordal replacement device.
Figure 40B:
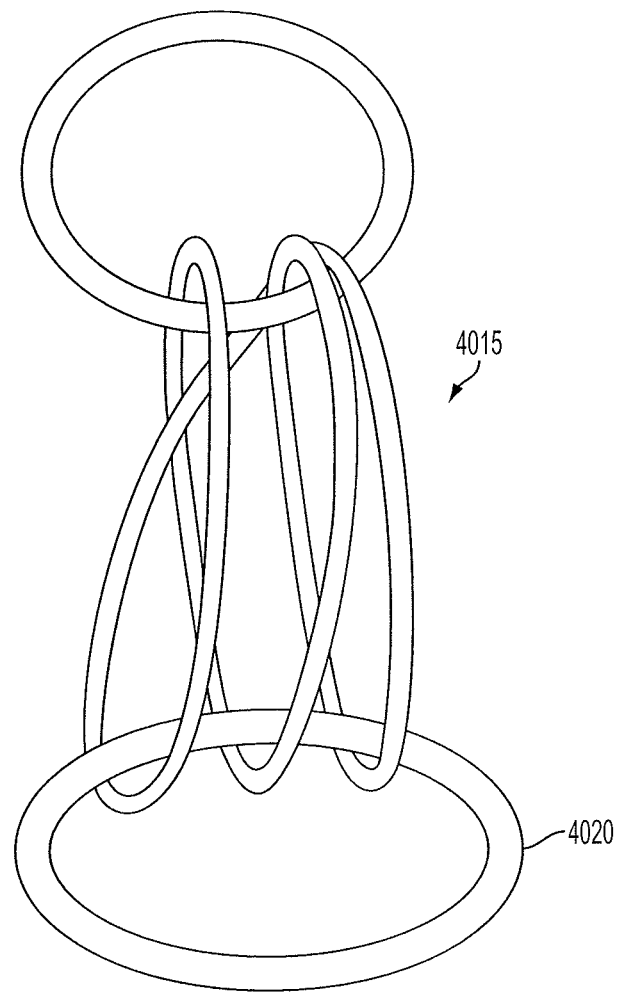

In another embodiment as shown in FIG. 40A-40B, a chordal replacement device 4005 can include a flexible material or patch 4010 that can be attached to the valve leaflet LF. A single strand of artificial chordae 4015 can loop through and underneath the patch 4010. The strand of artificial chordae 4015 can include one, two, three or more individual loops and can be made of suture or another flexible material. The loops of artificial chordae 4015 can be drawn together at one end with a ring 4020 or other enclosed shape going through the loops of artificial chordae 4015. The ring 4020 can be attached to the ventricle wall or papillary muscle or ventricular septum with a distal attachment assembly as described in more detail below.

The loops of artificial chordae 4015 can be a single strand of material that freely slides through the patch 4010 and the ring 4020 such that the loops 4015 can self-equalize to evenly distribute the load. A single loop 4015 can thread through the patch 4010 and the ring 4020, for example three times, such that one loop is short and there are two other loops that are long. Pulling the ring 4020 away from the patch 4010 will engage the short loop and redistribute the long loops to the length of the shortest loop such that the three loops are equally long and equally distribute the force. The loops of artificial chordae 4015 are not fixed such that they can slip and distribute the force equally between them. This self-equalizing characteristic along with the flexible patch 4010 reduces the stress on the leaflet LF.

Figure 41A:
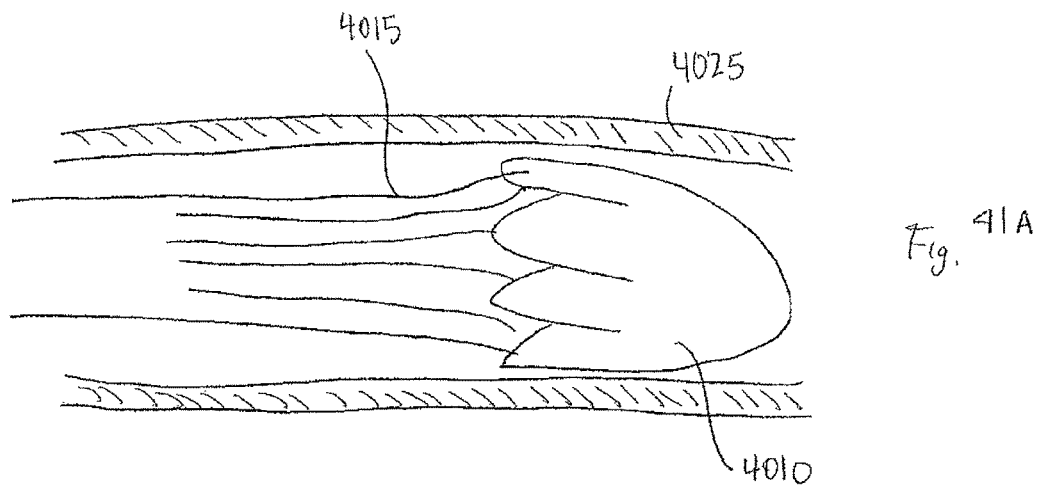
FIGS. 41A-41B show a cross-sectional view of the chordal replacement device of FIGS. 40A-40B being deployed.
Figure 41B:
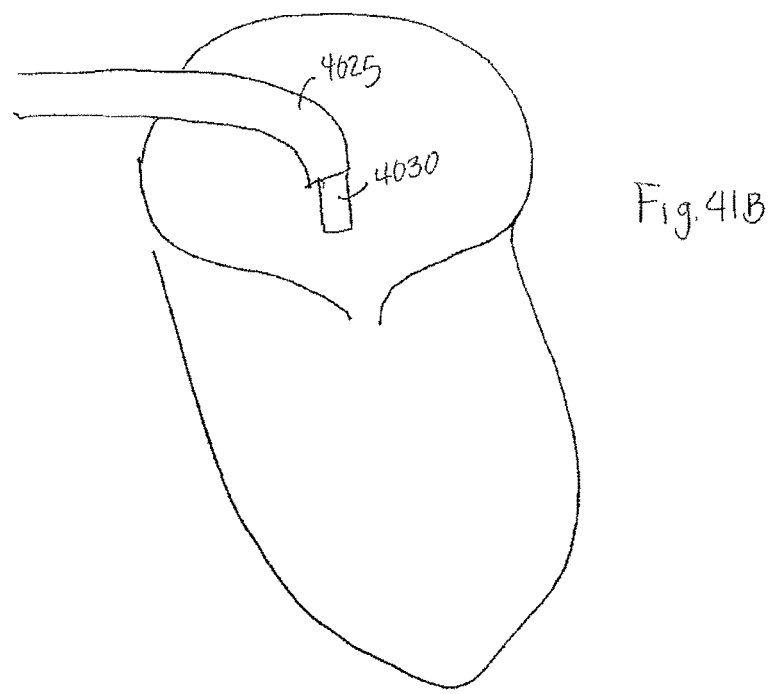
Figure 41C:
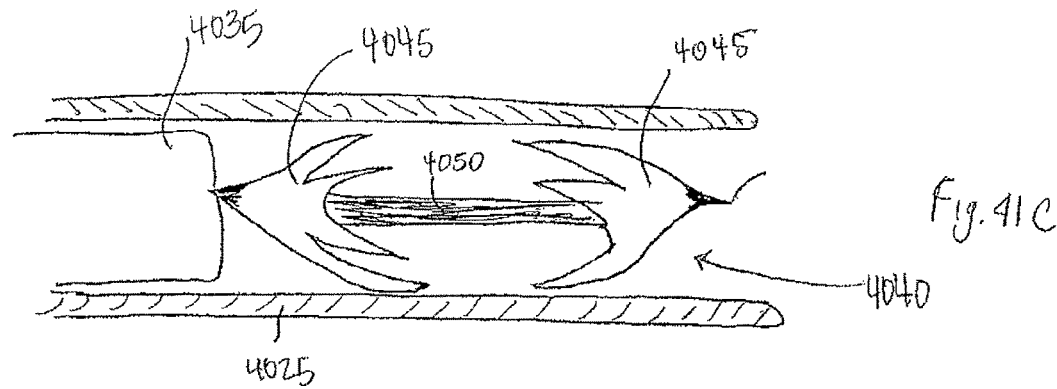
FIGS. 41C-41E show an embodiment of an attachment device fixing a chordal replacement device to a valve leaflet.

As shown in FIGS. 41A-41B, the device 4005 can be delivered to the valve leaflet (posterior or anterior). The patch 4010 can be folded and loaded into a delivery catheter 4025 such that the artificial chordae 4015 trail behind and are delivered through a guide catheter 4030 to the vicinity of the valve. A mandrel or pusher tube 4035 can push the patch 4010 out the distal end of the delivery catheter 4025 (see FIG. 41C).

Figure 41D:
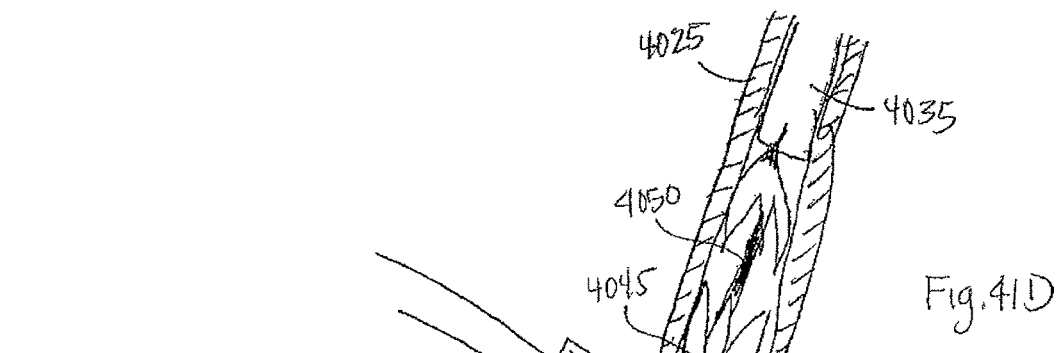
Figure 41E:
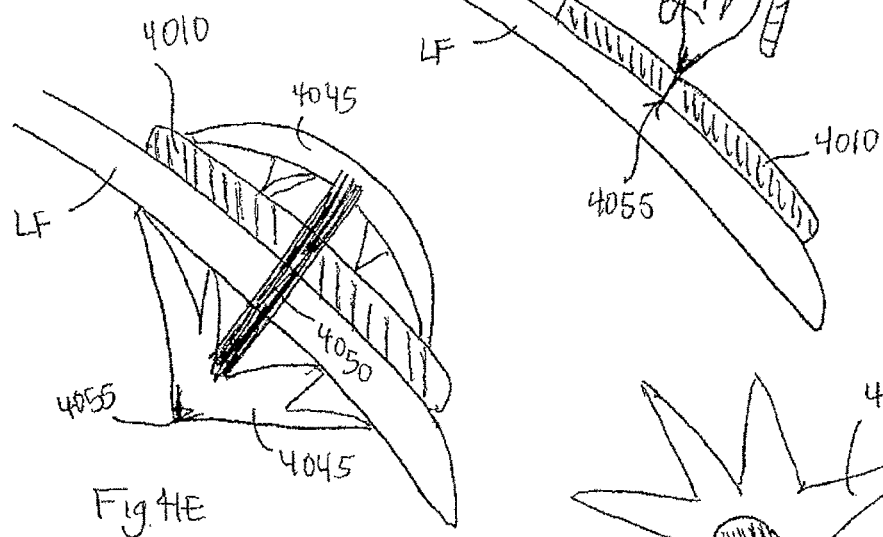

The leaflet LF can be stabilized using a vacuum or a hook attached to a guidewire or another stabilizing device. In an embodiment shown in FIGS. 41G-41N, the leaflet LF can be captured and/or stabilized using a guidewire 4141 having a distal end that has a needle point. The needle point guidewire 4141 can be delivered using a protective sheath or delivery catheter 4143 that prevents pricking of the vessel as it is passed therethrough. The sheath or delivery catheter 4143 can be retracted slightly exposing the distal needle point to the leaflet LF. The distal needle point can be urged through the leaflet LF near an edge or positioned closer to the valve annulus. The needle point guidewire 4141 can be pre-formed to have a hook shape such that when it is advanced out of the sheath 4143 and extends through the leaflet LF it can curve upward back toward the sheath 4143 to form a hook. In another embodiment shown in FIGS. 41O-41P, the guidewire 4141 can include a thicker needle point 4145 attached to a more flexible cable 4147 or guidewire or thinner wire. The needle point 4145 can also be preformed such that it takes on a sharper curve or hook shape when advanced beyond the distal end of the delivery catheter 4143. The needle point 4145 can be formed of a variety of materials such as Nitinol or other shape memory alloy or other suitable material.

Tension can be applied to the needle point guidewire 4141 such that the leaflet LF remains hooked and stabilized. Alternatively, the chordae can provide the resistance allowing the needle point guidewire 4141 to puncture the leaflet LF. The needle point guidewire 4141 as it forms the hook shape can penetrate the leaflet LF a second time (see FIG. 41K) although it should be appreciated that the guidewire need only penetrate the leaflet LF a single time to effect capture and stabilization (see FIG. 41M). To release the leaflet LF from the needle point guidewire 4141, the sheath 4143 can be advanced distally back over the needle point as shown in FIG. 41N. The portion of the guidewire 4141 penetrating the leaflet LF is slowly withdrawn as the sheath 4143 is advanced distally.

The patch 4010 can be affixed to the valve leaflet LF by activating a leaflet attachment device 4040 through the guide catheter 4030. In an embodiment, the leaflet attachment device 4040 can include a pair of expandable elements 4045 connected centrally by a rod 4050. One or more of the expandable elements 4045 can have a sharp needle point 4055. The patch 4010 can lie on top of the valve leaflet LF and the sharp needle point 4055 of the leading expandable element 4045 can pierce through the patch 4010 and the leaflet LF such that the leading expandable element 4045 emerges from the underneath side of the leaflet LF and the rod 4050 extends through the leaflet (see FIGS. 41D and 41E). The patch 4010 on the upper surface of the leaflet LF can be sandwiched between the leading and trailing expandable elements 4045 of the leaflet attachment device 4040. The leaflet attachment device 4040 and each of the expandable elements 4045 can be a shape-memory metal (e.g. Nitinol, Nitinol alloys) or some other spring material. The spring material of the expandable elements 4045 allows them to spring out as the leaflet attachment device 4040 is advanced from the distal end of the delivery catheter 4025. The leaflet attachment can be facilitated by stabilizing the leaflet as described above. The position of the patch prior to securement of the exapandable element 4045 can be maintained for example, by attaching the patch to the first expandable element prior to being deployed from the delivery catheter. The delivery catheter can then be used to maneuver into position the patch prior to deploying the first expandable element.

Figure 41F:
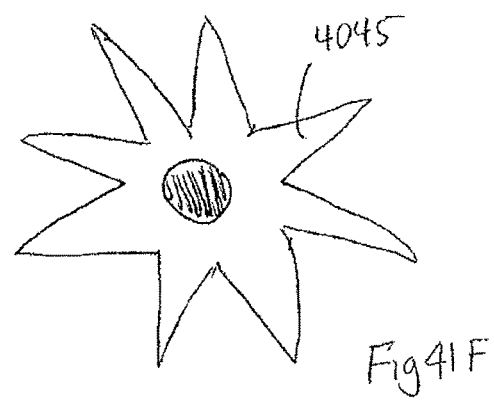
FIG. 41F shows an embodiment of an expandable feature of an attachment device having a star-shaped design.
Figure 41G:
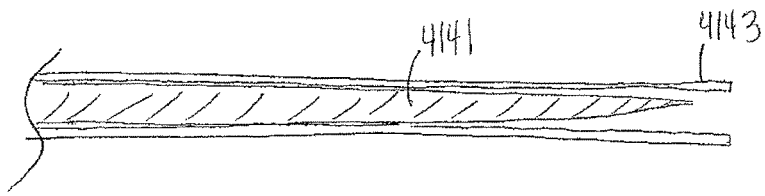
FIGS. 41G-41P show embodiments of a leaflet stabilizing mechanism.
Figure 41H:
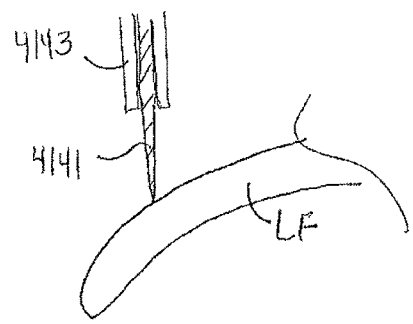
Figure 41L:
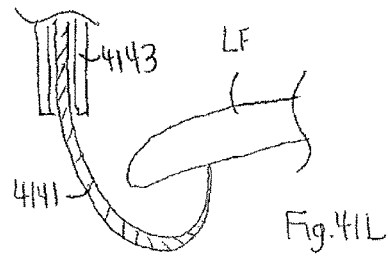
Figure 41I:
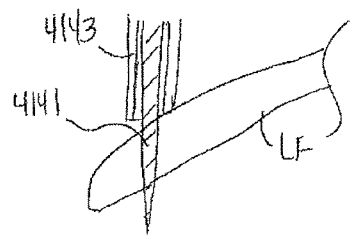
Figure 41M:
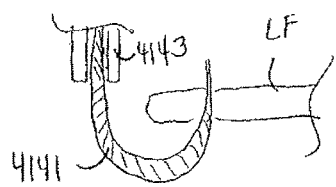
Figure 41J:
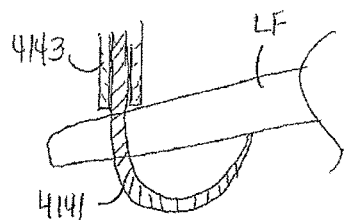
Figure 41K:
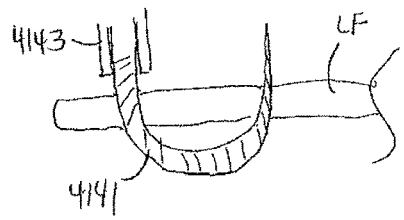
Figure 41N:
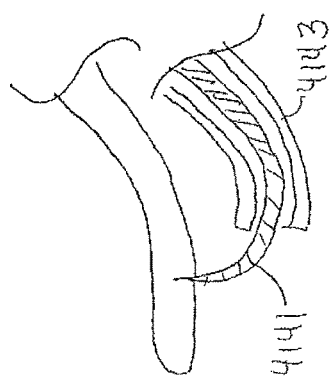
Figure 41O:
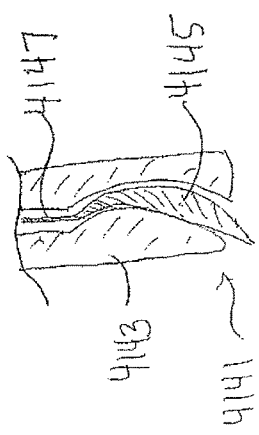
Figure 41P:
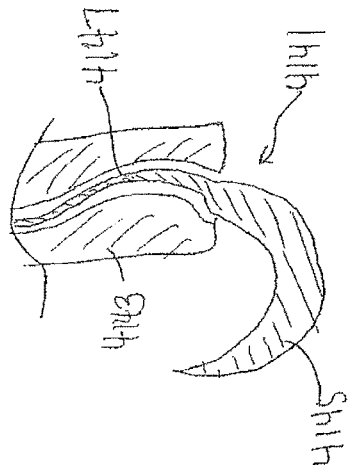

FIG. 41F shows a top view of an expandable element 4045 deployed on the upper surface of the leaflet. The embodiment is shown having barbed arms in a star-shaped configuration although it should be appreciated that other shapes and configurations are considered. For example, as shown in FIGS. 42A-42B, the leaflet attachment device 4040 can include expandable elements 4045 of a spring metal mesh. The spring metal mesh expandable element 4045 can form a web shape and flatten out as it is deployed. Alternatively, the Nitinol or other spring material can spring into an expandable element 4045 shaped like a mesh ball (see FIG. 42C). Upon expansion, the mesh ball expandable element 4045 can protectively cover the sharp needle point 4055 on the underneath side of the valve leaflet. It should also be appreciated that the leaflet attachment device 4040 can include expandable elements 4045 that are a combination of configurations including flat mesh design, ball mesh design, a star-shaped design or other configuration. For example, one expandable element 4045 can have a star-shaped design and the other expandable element 4045 can have a mesh ball design (see FIG. 42D). The expandable devices such as the mesh ball design can be collapsed sufficiently small to pass through a needle hole without ripping the leaflet. In an embodiment, the needle bore can be a larger hypotube such that insertion of the tube needle can punch a hole in the leaflet. The patch 4010 can cover the hole such that leaks are avoided. Further, the hypotube can be dull at the base of the bore such that punched out tissue remains attached to avoid creation of an embolism.

It should be appreciated that more than one leaflet attachment device 4040 can be used to affix a patch 4010 to the valve leaflet LF. As shown in FIG. 43A, the patch 4010 can be attached to the atrial side of the valve leaflet LF with multiple leaflet attachment devices 4040 oriented side-by-side on the upper and lower surface of the leaflet LF. Using multiple leaflet attachment devices 4040 to affix the patch 4010 reduces stress in the leaflet LF, in part, due to distribution of forces across multiple attachment locations. As shown in FIG. 43B, the multiple leaflet attachment devices 4040 can be stacked and deployed in series from a delivery catheter 4025. In another embodiment, the multiple leaflet attachment devices 4040 can be deployed using a guide wire between deployments of each leaflet attachment device 4040. For example, the patch 4010 can be deployed followed by the first leaflet attachment device 4040. The delivery catheter 4025 can be withdrawn leaving a guide wire 4060 in place. Another catheter with the second leaflet attachment device 4040 can then be advanced along the guide wire 4060 and the second leaflet attachment device 4040 deployed. The process can be repeated depending on the number of attachment devices desired to be deployed.

Figure 44A:
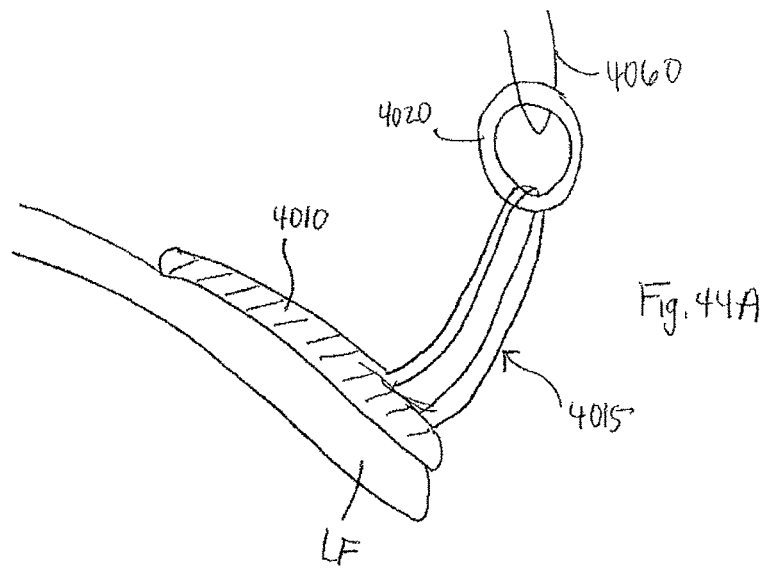
FIGS. 44A-44D show various steps in the deployment of an embodiment of a chordal replacement device.
Figure 44B:
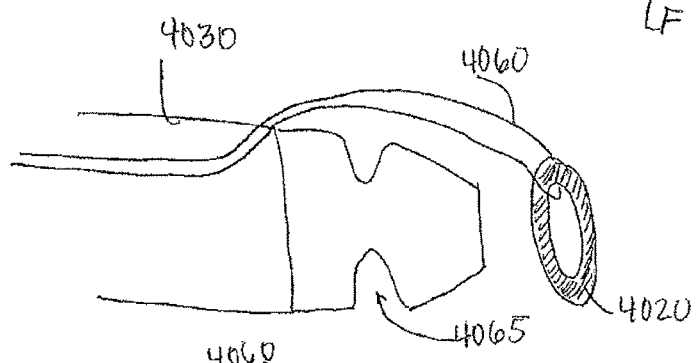
Figure 44C:
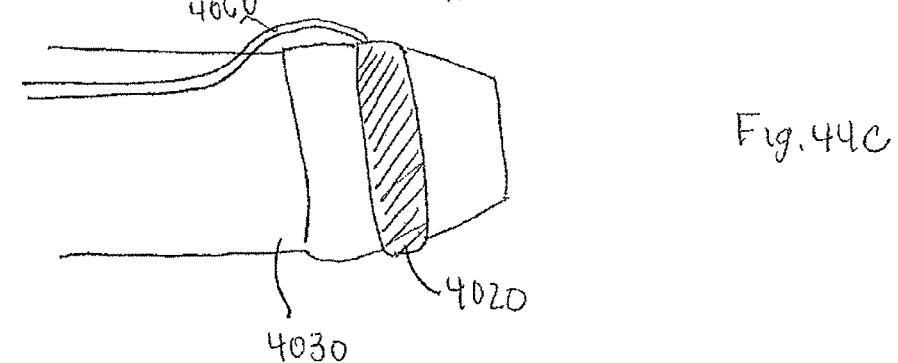
Figure 44D:
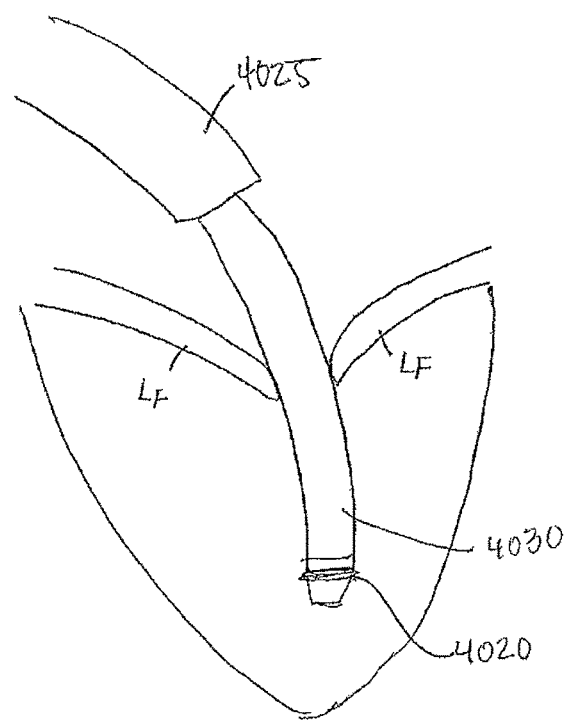

Once the patch 4010 is positioned and affixed to the leaflet LF, such as with the leaflet attachment device(s) 4040, the loops of artificial chordae 4015 can be deployed distally within the ventricle such as to the ventricular wall, septum or papillary muscle. As shown in FIG. 44A, the delivery catheter 4025 that deployed the patch 4010 and leaflet attachment device(s) 4040 can be removed from the guide catheter 4030 leaving a guide wire 4060 attached to a ring 4020 through which the artificial chordae 4015 loop (attachment device(s) are not shown in the figure for simplicity). The guide wire 4060 can be previously looped through the ring 4020, for example, during manufacturing. Another catheter can be advanced over the guide wire 4060 through the guide catheter 4030. In an embodiment, the ring 4020 is attached to the distal end of the catheter 4030 as shown in FIG. 44B-44C. For example, the ring 4020 can be inserted or snapped into a flanged channel 4065 near the distal end of the catheter 4030 using the guide wire 4060 looped through the ring 4020. The catheter 4030 with the ring 4020 in the channel 4065 can advance through the valve distally into the ventricle (see FIG. 44D).

As shown in FIGS. 45A-45D, the ring 4020 with the attached loops of artificial chordae 4015 can be anchored to the ventricular wall or papillary muscle forming a distal attachment assembly 4070 of the chordal replacement device. In an embodiment a coil screw 4075 is coupled to the distal attachment assembly 4070. The coil screw 4075 can be advanced like a cork screw through the distal end of the catheter 4030 into the ventricular tissue, for example, by rotating an actuator knob on the proximal end of the catheter. The rotation of the actuator knob can rotate the coil screw, advancing it out of the catheter and into the ventricular tissue.

Figure 45A:
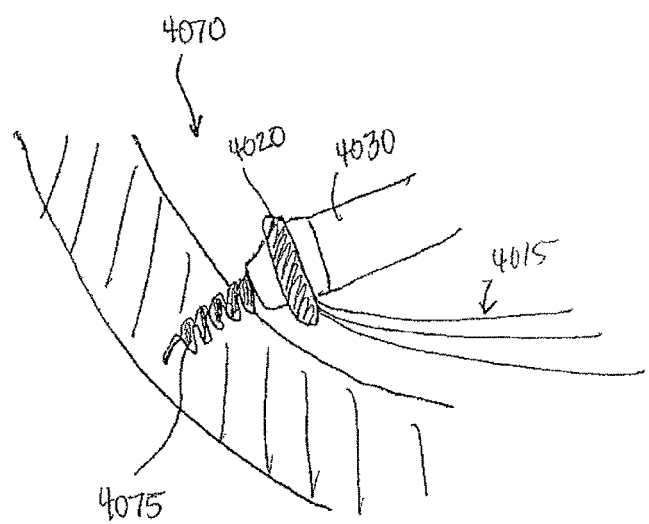
FIGS. 45A-45D show various embodiments of a distal attachment assembly deployed in the ventricle wall.
Figure 45B:
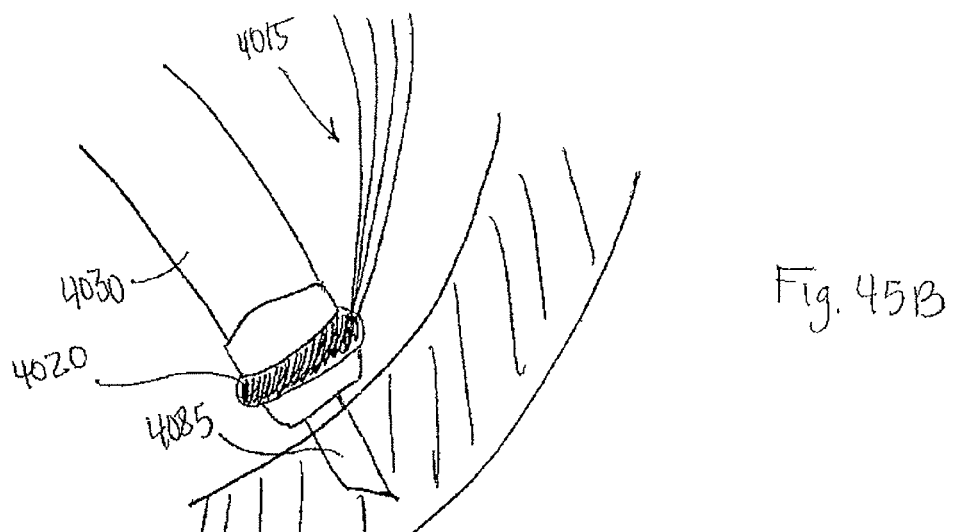
Figure 45C:
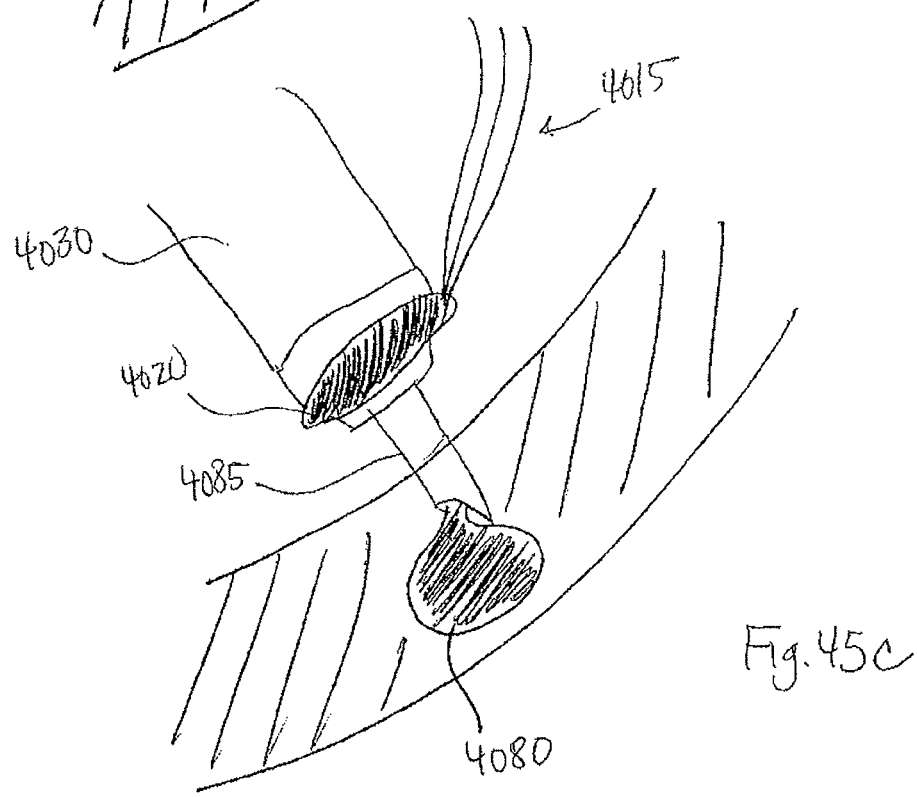
Figure 45D:
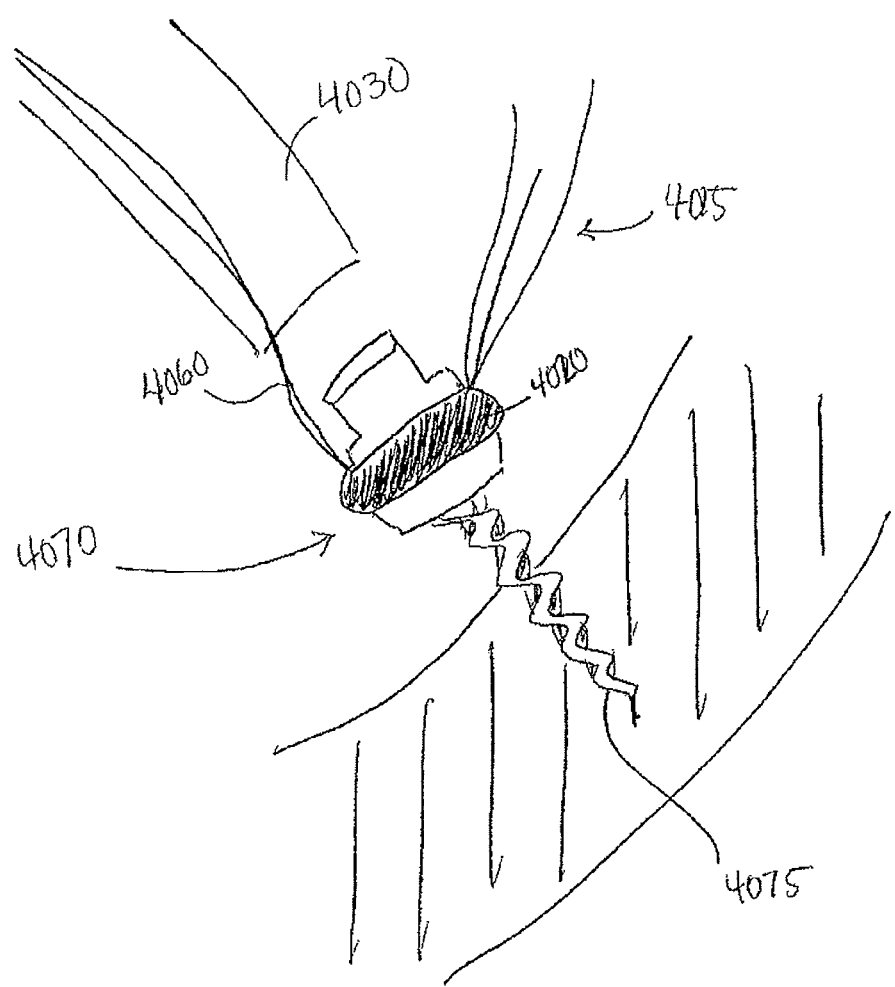

In another embodiment, the distal attachment assembly 4070 can be coupled to or can include a fillable element 4080 delivered through a hollow needle 4085 that pierces the ventricular wall (See FIGS. 45B-45C). The fillable element 4080 can include a balloon or mesh bag or other expandable element. A hardening agent or other material can be used to fill the element 4080 expanding it such that it anchors the artificial chordae 4015 and the distal attachment assembly 4070 to the ventricle. The needle 4085 can be retracted leaving the filled element 4080 inserted in the ventricle wall and coupled to the distal attachment assembly 4070. The hardening agent can be a two-part hardening agent, such that a small quantity of a second agent can be delivered through another smaller tube in the catheter to activate the first part and main bulk of the hardening agent.

After the distal anchor (e.g. coil screw 4075 or filled element 4080) of the distal attachment assembly 4070 is attached to the ventricular wall or papillary muscle, the distal attachment assembly 4070 can be released from the guide catheter 4030. The assembly 4070 can be released, for example, using a mandrel that runs through the catheter and has a threaded end that threads into the distal attachment assembly. In another embodiment, the distal end of the catheter can be a sleeve that pinches circumferentially onto the attachment assembly and then by retracting a lever proximally, a mandrel is retracted which pulls the pinching sleeve backwards over the catheter slightly, expanding the pinching sleeve and releasing the attachment assembly. The two ends of the guide wire 4060 can extend all the way up through the guide catheter 4030. As the delivery catheter 4025 is removed, the guide wire 4060 can still be looped through the ring 4020. The guide wire 4060 can be removed before, during or after the delivery catheter 4025 is removed. The guide wire 4060 can be removed by pulling one end, allowing the trailing end to pull through the ring 4020 and then out of the guide catheter 4030 leaving the distal attachment assembly 4070 anchored in the ventricle and the artificial chordae 4015 extending up to the valve leaflet LF where the patch 4010 is affixed to the leaflet LF with the leaflet attachment device(s) 4040.

Figure 46A:
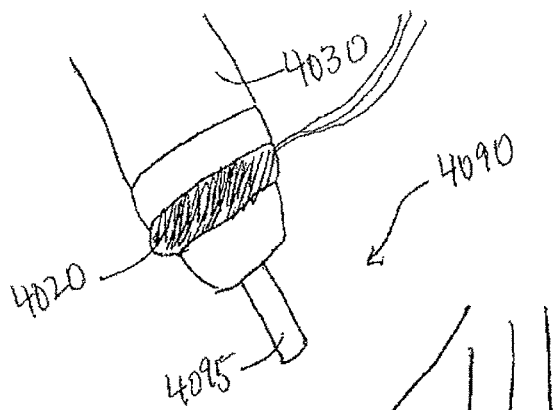
FIGS. 46A-46B show an embodiment of a sensor used in the adjustment of artificial chordae tension.
Figure 46B:
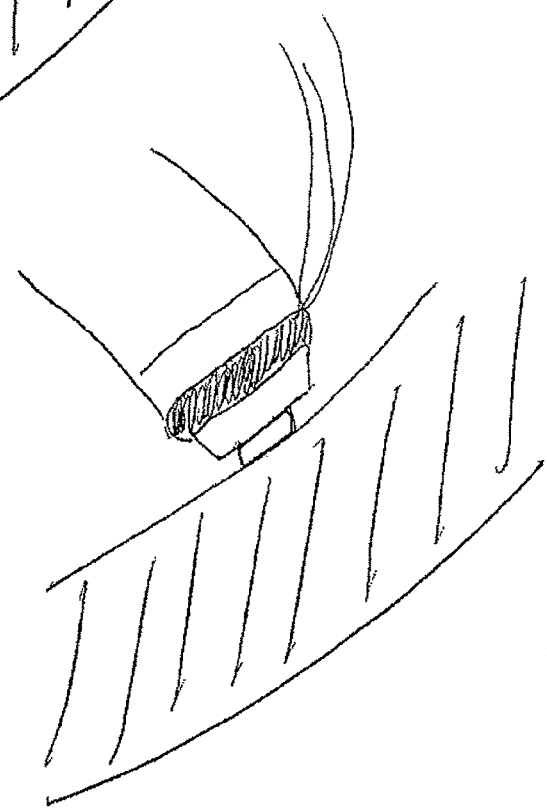

Once the chordal replacement device is deployed, the tension of the artificial chordae 4015 can be adjusted. In an embodiment, a sensor 4090 such as a pin or pressure sensor can be used to adjust tension in the artificial chordae 4015. The sensor 4090 can provide the user with information regarding contact between the guide catheter 4030 and the ventricular wall. As shown in FIG. 46A-46B, the sensor 4090 can include a pin 4095 near the distal tip of the catheter 4030. The pin 4095 is shown in FIG. 46A as fully extended indicating no contact with the ventricular wall. Upon contact with the wall as shown in FIG. 46B, the pin 4095 can compress and activate delivery of a signal to the user such as an electrical signal or visual signal indicating that contact is made with the wall of the ventricle. If the sensor 4090 indicates contact with the ventricular wall and an echocardiogram suggests no flail or prolapse and mitral regurgitation (MR) is reduced then the distal anchor (e.g. coil screw 4075 or element 4080) can be advanced into the ventricular wall to secure attachment. If the sensor 4090 indicates contact with the ventricular wall, but the echocardiogram suggests flail and/or prolapse and poor MR results, the catheter 4030 can be moved further down into the ventricle to increase tension on the artificial chordae 4015 and the test repeated. If the sensor 4090 indicates contact with the ventricular wall, and the echocardiogram suggests no flail and/or prolapse but the MR results are still poor, the leaflet is pulled down too far and the catheter 4030 can be moved proximally to release tension on the artificial chordae 4015. The test can be repeated until desirable results are achieved.

Figure 47:
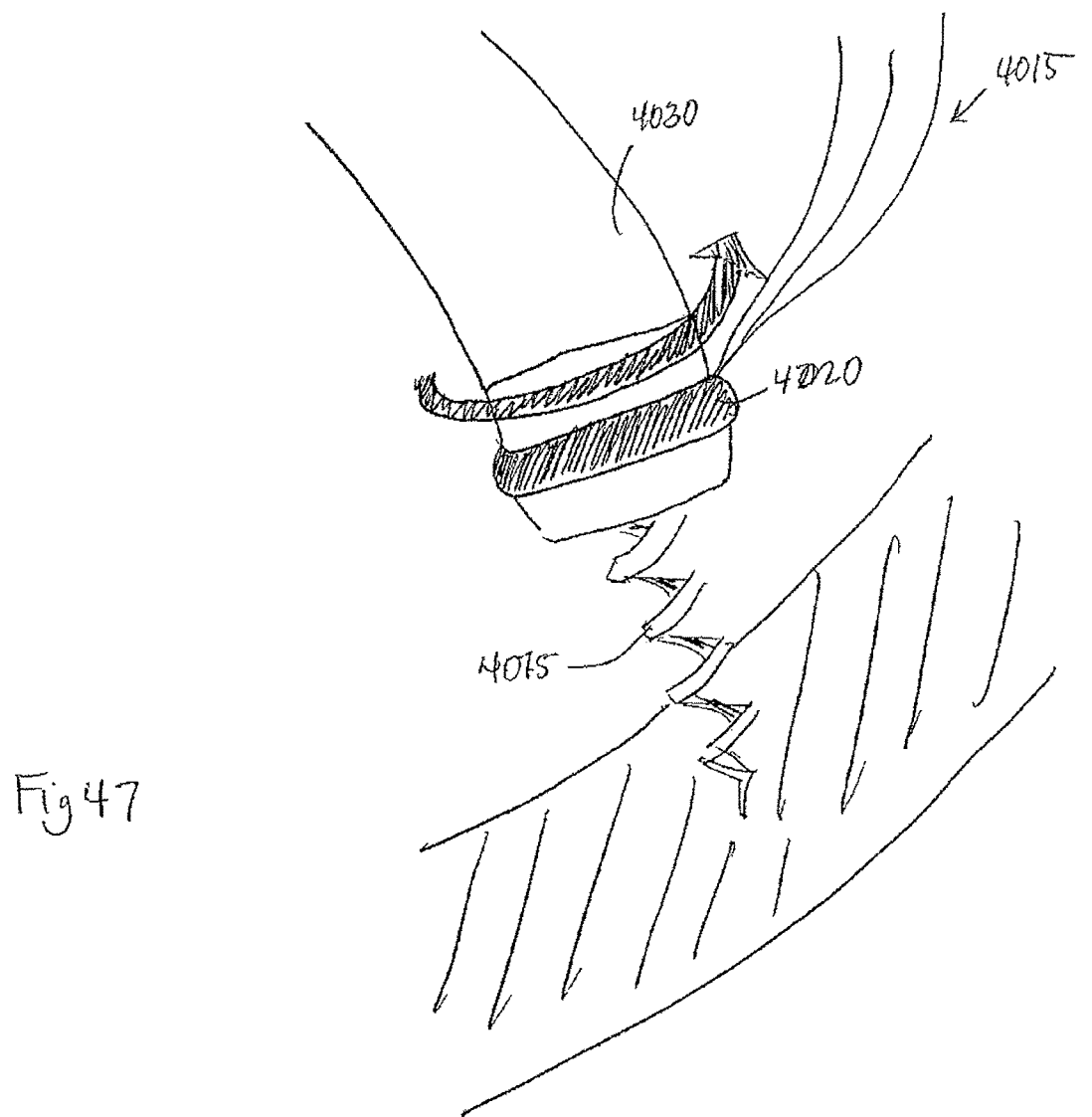
FIG. 47 illustrates an embodiment of fine-tuning the tension on the artificial chordae.

Once the distal anchor is advanced into the ventricular wall and adequate results are obtained, fine-tuning of the tension can be performed (see FIG. 47). In an embodiment, the distal anchor can be a coil screw 4075 that is advanced and locked. The distal attachment assembly 4070 can be rotated clockwise by the catheter 4030 to draw the ring 4020 slightly closer to the ventricular wall. The distal attachment assembly 4070 can also be rotated by the catheter 4030 in a counter-clockwise direction to push the ring 4020 away such that the valve leaflet LF can rise up slightly.

In another embodiment as shown in FIGS. 48A-48B, the distal anchor can be an expandable element, such as a balloon anchor filled with a two-part epoxy as described above. This embodiment can also be fine-tuned. As the expandable element 4080 expands within the ventricular wall, the distal attachment assembly 4070 attached to the expandable element 4080 is pulled toward the ventricular wall. The material of the expandable element 4080 can be finitely expanded such that fine-tuning of the distance between the distal attachment assembly 4070 and the ventricular wall can be performed. As the expandable element 4080 is unexpanded the artificial chordae 4015 can pull the distal attachment assembly 4070 away from ventricular wall and the valve leaflet can rise slightly. Once gross adjustments are performed, fine-tuning the tension on the artificial chordae 4015 attached to the valve leaflet can be performed. The first part epoxy (i.e. prior to hardening) can be used to fill the expandable element 4080 and also fine-tune the positioning and tension on the chordae 4015. Once the proper position is confirmed, the second part of the epoxy can be infused such that it hardens and sets in place the chordae. It should be appreciated that the epoxy can be embedded directly into the attachment site or can be used to fill a expandable element pre-embedded in the distal attachment site. Ideally, very little of the second part epoxy is used so as not to interfere with the fine-tuning achieved.

Figure 49A:
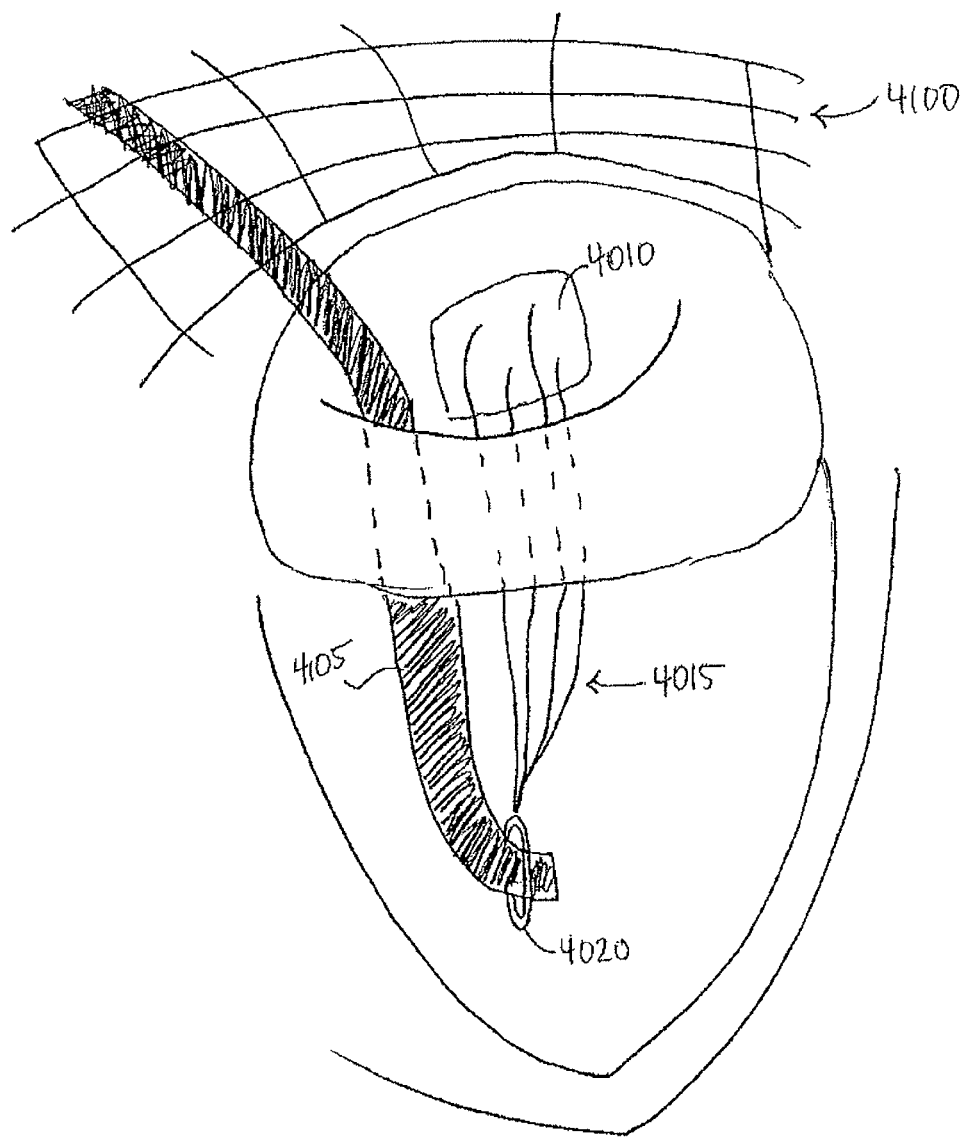
FIGS. 49A-49B show another embodiment of an attachment assembly for a chordal replacement device.
Figure 49B:
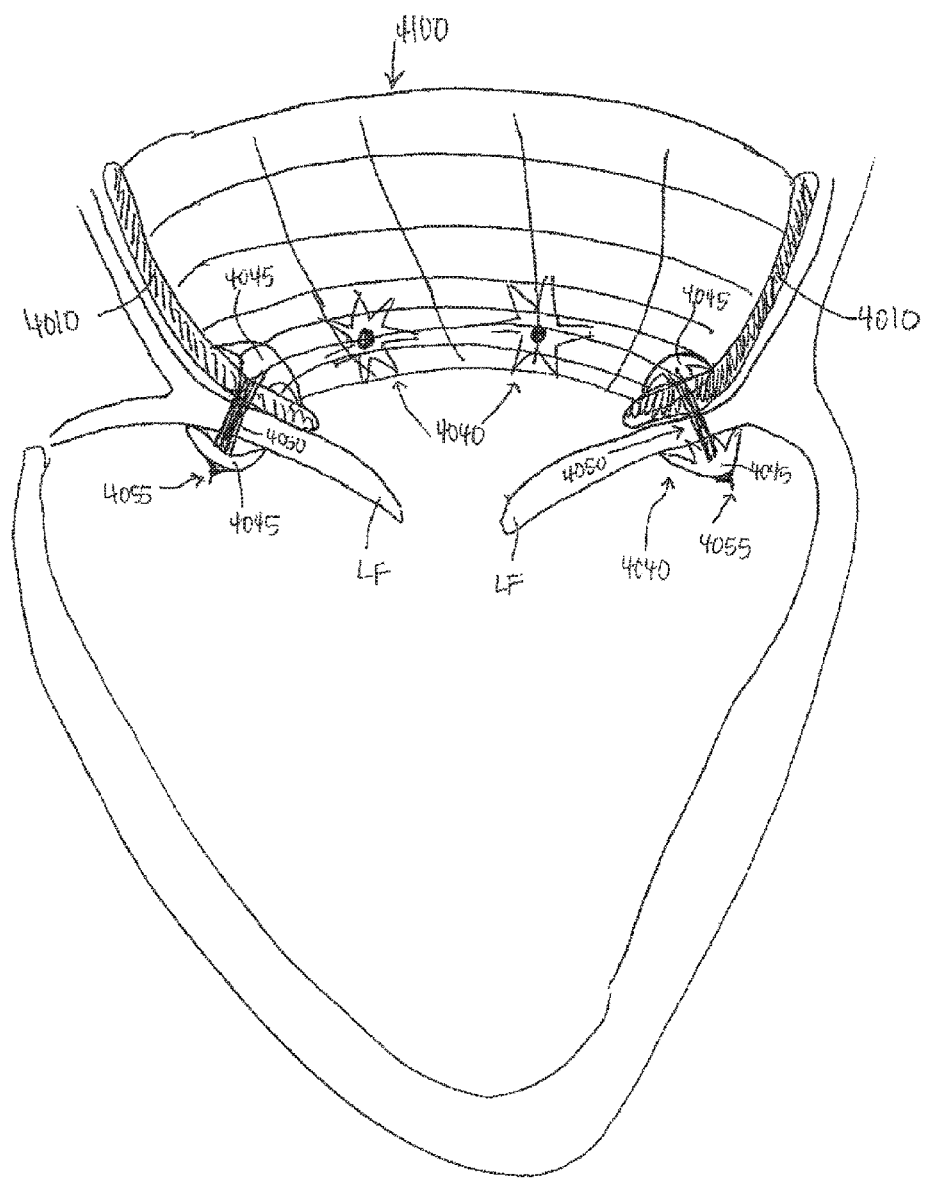

The chordal replacement device need not include a distal attachment assembly 4070 (see FIGS. 49A-49B). For example, the chordal replacement device can be attached to an attachment assembly that is deployed proximal to the valve. In an embodiment, the chordal replacement device can include a ring 4020 and loops of artificial chordae 4015 attached to a rod 4105 extending from a spring material (e.g. shape-memory metal such as Nitinol or other material) that forms a stent-like mesh 4100 deployed in the left atrium, just above the mitral valve. The rod 4105 can be attached to the mesh 4100 and extend from the mesh 4100 through the mitral valve such as at one of the commissures into the ventricle. The rod 4105 can be straight or curved or jointed. The distal end of the rod 4105 can be attached to the ring 4020 such as by extending through the ring 4020. Rod 4105 and mesh 4100 can be moved to adjust tension on the artificial chordae 4015. Once in a desirable location and the desired tension is achieved, the mesh 4100 and rod 4105 can be secured within the atrium or to the valve leaflets, for example using the leaflet attachment devices 4040 discussed above (see FIG. 49B; note the rod, ring and replacement chordae are not shown).

Figure 50A:
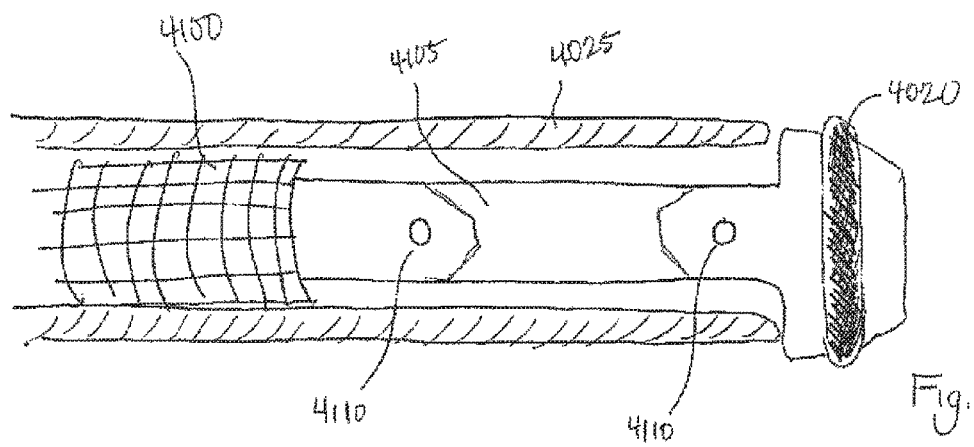
FIGS. 50A-50B show another embodiment of an attachment assembly for a chordal replacement device.

As shown in FIG. 50A, the rod 4105 and mesh 4100 can be delivered through a delivery catheter 4025 in which the mesh 4100 is collapsed. As mentioned above, the rod 4105 can be jointed. The joints 4110 can lock in place once the rod 4105 is deployed and/or can have limited travel around the joint 4110. As shown in FIGS. 50C-50E, one or more of the rod joints 4110 can lock into place using a mechanical/physical feature incorporated within the joint 4110. In an embodiment, one or more of the joints 4110 can have a surface feature 4112 such that when the rod 4105 rotates over the surface feature 4112 on the adjacent portion of the joint 4110 it can pop over and lock in place relative to the adjacent portion of the joint 4110.

Figure 50B:
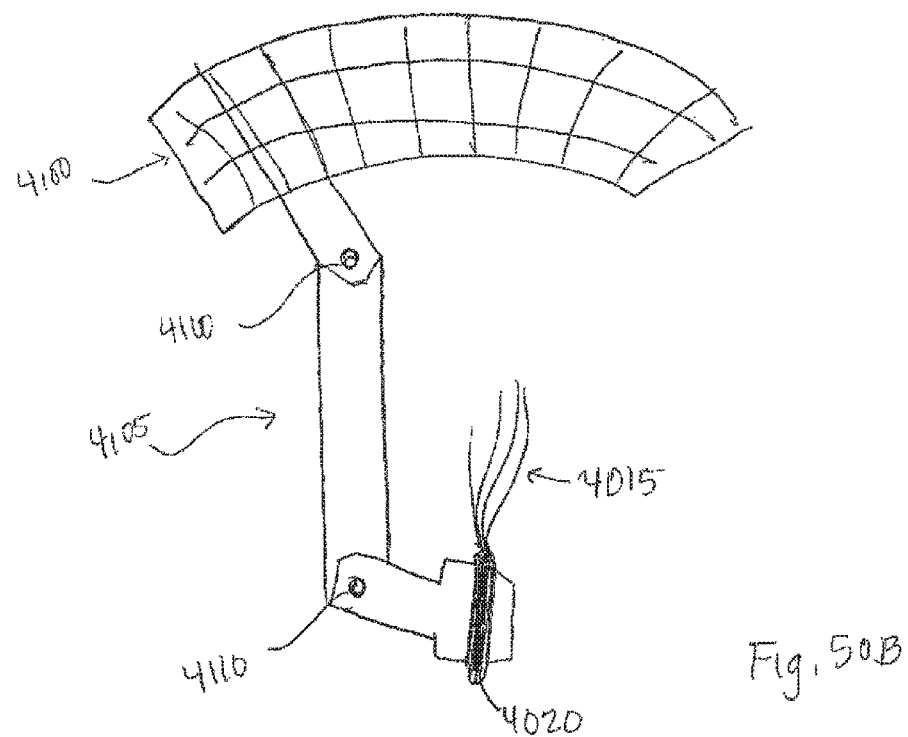
Figure 50F:
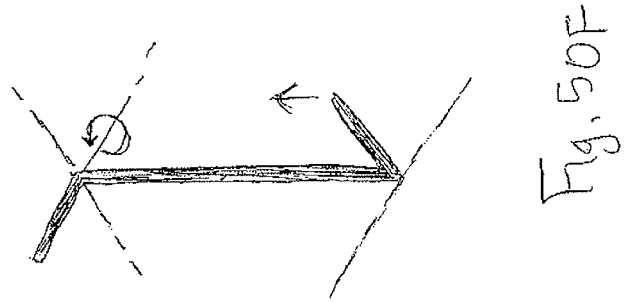
FIG. 50F illustrates the independent pivot axes of a jointed rod system.

Even in the locked position, one or more of the joints 4110 can have limited travel around the joint 4110 to provide the artificial chordae 4015 with some degree of slack (see FIG. 50B). The rod 4105 and mesh 4100 can passively rise and fall with the mitral annulus during the cardiac cycle. In diastole, when the annulus rises, excessive tension on the artificial chordae 4015 can be avoided due to this limited travel around the joint 4110. In an embodiment, the top joint 4110 can lock and the bottom joint does not lock. In this embodiment, the lower joint can pivot without detriment to the system as the annulus rises during diastole. During systole, the lower joint can pivot in the opposite direction due to tension on the chordae until the physical stop incorporated in the joint limits the travel. In this position the rod system can then provide tension to the chordae and hold the leaflets down. As shown in FIG. 50F, the top joint 4110 rather than being fixed can pivot about an axis that is orthogonal to the axis of the bottom joint. This arrangement can prevent the forces of the cardiac cycle from bending the top joint once deployed.

Figure 51A:
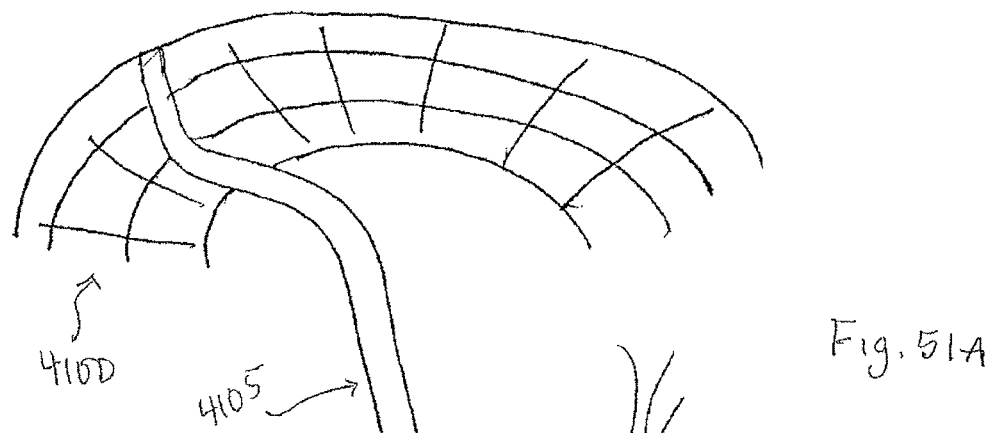
FIGS. 51A-51B show another embodiment of an attachment assembly for a chordal replacement device.
Figure 51B:
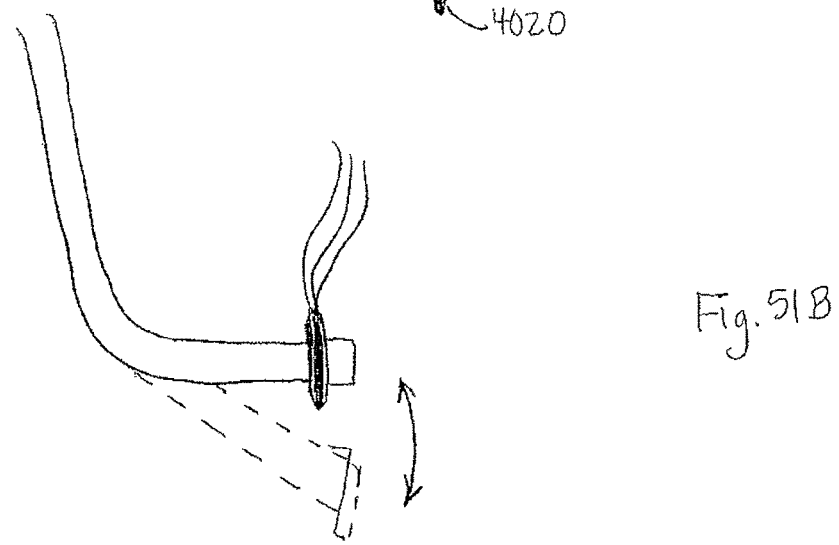

With reference to FIGS. 51A-51B, rather than using a jointed rod, the rod 4105 can be flexible so that it can fit in a delivery catheter 4025 and expand to its spring-formed shape when deployed from the delivery catheter 4025. Flexibility of rod 4105 can be designed so that it provides a predictable spring force on the artificial chordae 4015. The rod 4105 can deflect and provide consistent tension on the artificial chordae 4015.

Figure 52A:
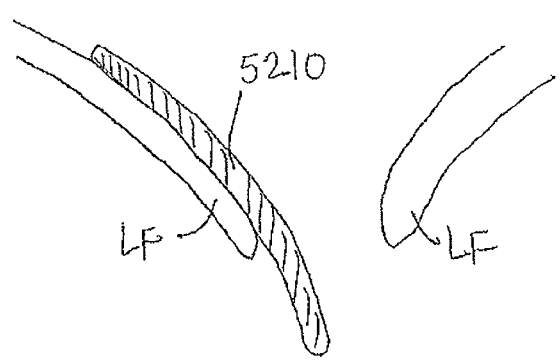
FIGS. 52A-52C show an embodiment of a leaflet extension device blocking valve leaflet flail.
Figure 52B:
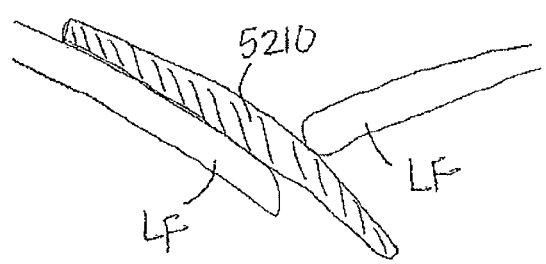
Figure 52C:
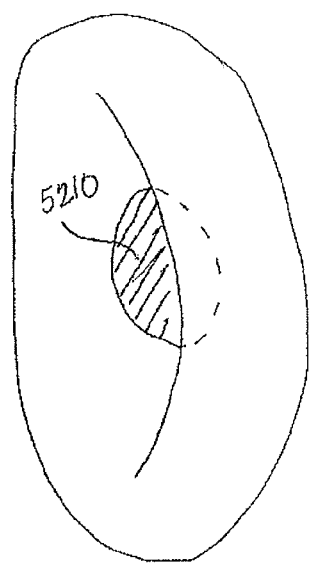

It should be appreciated that in addition to a chordal replacement system, the leaflet attachment devices 4040 described above can be used to attach a leaflet extension patch for the treatment of mitral valve prolapse or flail. As shown in FIGS. 52A-52C, the leaflet extension patch 5210 can be attached to the atrial side of the valve leaflet. The leaflet extension patch 5210 can be a stiff or a flexible material. The leaflet extension patch 5210 can prevent mitral regurgitation in the case of prolapse or flail in that it can block the leaflet from flailing upwards into the atrium. For functional mitral regurgitation, the leaflet extension patch 5210 can bridge any coaptation gap between the leaflets.

FIG. 52A shows the leaflet extension patch 5210 during diastole. The patch 5210 can follow the leaflet downwards such that flow through the valve is not impeded. During systole, the leaflet extension patch 5210 can block flow by coapting with the opposite leaflet LF as well as prevent flail or prolapse by physically blocking it from moving upwards into the atrium (see FIGS. 52B and 52C).

Figure 14:
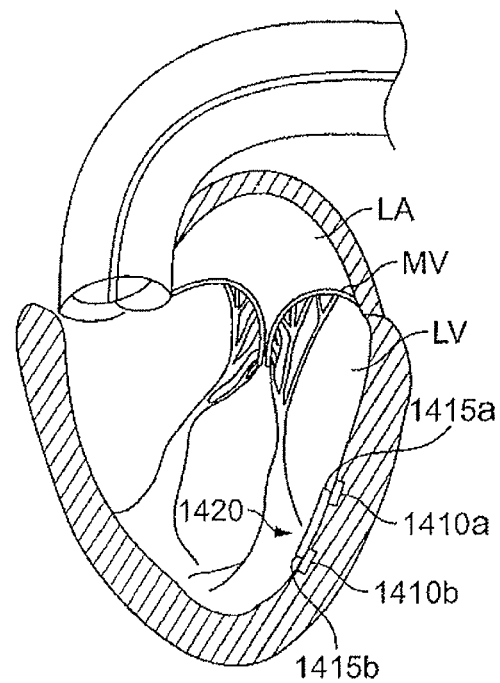
FIG. 14 shows a cross-sectional view of the heart with a first and second anchor attached to a wall of the heart.

Other embodiments are directed to atrial or ventricular remodeling to alter the shape of an atrium or ventricle. Now with respect to FIG. 14 which shows a cross-sectional view of the heart with a first and second anchor attached to a wall of the heart. The system includes a first anchor 1410a having a screw portion 1415 for screwing into a wall of the heart and a connector portion. The connector portion is rotatable around an axis of rotation. The first anchor includes a power source to power rotation of the connector portion and a receiver for receiving telemetric signals from an external controller for controlling the rotation of the connector portion. The system includes a second anchor 1410b having a screw portion 1415b for screwing into a wall of the heart and a connector portion. Also included is a tether 1420 having two free ends. One of the free ends is coupled to the connector portion of the first anchor, and the other free end is coupled to the connector portion of the second anchor. An external controller is also included. The external controller has a telemetric transmitter for communicating with the receiver and controls the rotation of the connector portion. Alternatively, the anchors may be placed with a torqueable catheter.

In another embodiment, a method of altering a geometry of a heart includes introducing a first coupler into a heart chamber. The first coupler has an anchor portion and a connector portion. The connector portion is rotatable around an axis of rotation and is connected to a power source to power rotation of the connector portion. The power source is in communication with a telemetric signal receiver. The first coupler is secured to the wall of the heart chamber by anchoring the anchor portion to the wall. A second coupler is introduced into the heart chamber. The second coupler includes an anchor portion and a connector portion. The second coupler is secured to the wall of the heart chamber by anchoring the anchor portion to the wall at a distance from the first coupler.

A tensile member is introduced into the heart chamber. One end of the tensile member is connected to the connector portion of the first coupler, and another end of the tensile member is connected to the connector portion of the second coupler. The distance between the first and second couplers is adjusted by transmitting a telemetric signal to the receiver, thus causing the connector portion to rotate around the axis of rotation and threading the tensile member around the connector portion to reduce the distance between the first and second couplers.

In another embodiment, a system for altering the geometry of a heart chamber includes a planar tensile member having substantially inelastic material. At least two anchors are included for anchoring the planar tensile member to an inner wall of a heart chamber. The planar tensile member is substantially shorter in length than a left ventricle of a heart so that when the planar tensile member is anchored in a caudal direction along a length of the left ventricle a tensile force exerted by the planar tensile member between the two anchors prevents the left ventricle from dilating caudally.

In another embodiment, a method for altering the geometry of a heart includes providing a tensile member having a substantially inelastic material. The tensile member is substantially shorter in length than a left ventricle of a heart.

The tensile member is inserted into the left ventricle of the heart and a proximal end of the tensile member is anchored to the left ventricle adjacent the mitral valve. A distal end of the tensile member is anchored to the left ventricle caudal the proximal end so that a tensile force exerted by the tensile member between the two anchors prevents the left ventricle from dilating caudally.

Figure 15:
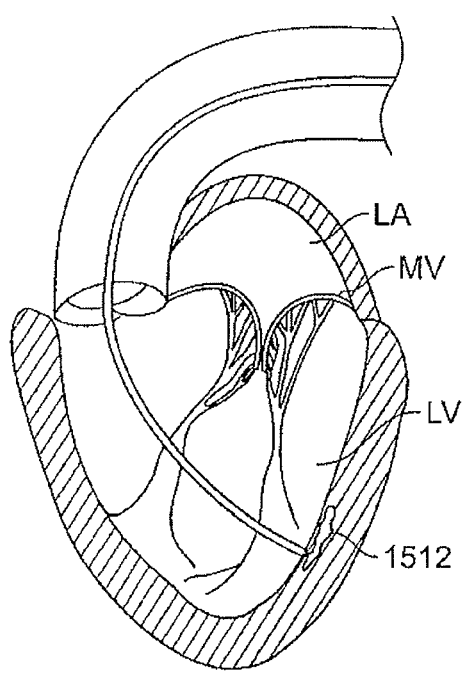
FIG. 15 shows a catheter that has been introduced into the heart.

Other embodiments are directed to strengthening or reshaping the left ventricle of the heart. In one embodiment in particular, a method of reinforcing the left ventricle includes injecting a strengthening agent into a wall of the left ventricle in an enlarged region of the ventricle, as shown in FIG. 15. FIG. 15 shows a catheter 1510 that has been introduced into the heart. The catheter 1510 has an internal lumen through which the strengthening agent 1512 can be injected. A proximal end of the catheter is connected to a source of the strengthening agent and a distal end of the catheter is configured to release the strengthening agent. As shown in FIG. 15, the distal end of the catheter is positioned at or near a wall of the heart and the strengthening agent 1512 is injected into the wall of the heart.

In another embodiment, a method is directed to altering the geometry of a heart. The method includes injecting a polymerizing agent into a pericardial space adjacent a left ventricle, thereby exerting a medial (inward) force against the left ventricle.

In yet another embodiment, a method of altering the geometry of a heart includes inserting a balloon into a pericardial space adjacent to a left ventricle of the heart, or extend into the pericardium of the heart. The balloon is inflated by injecting it with a fluid, and it exerts a medial force against the left ventricle upon inflation. In certain embodiments, the balloon can be inflated at the time of implantation, or at a later time. If inflated at a later time, the balloon would be self-sealing, and may be inflated by accessing the balloon with a needle placed through the chest wall.

Figure 16:
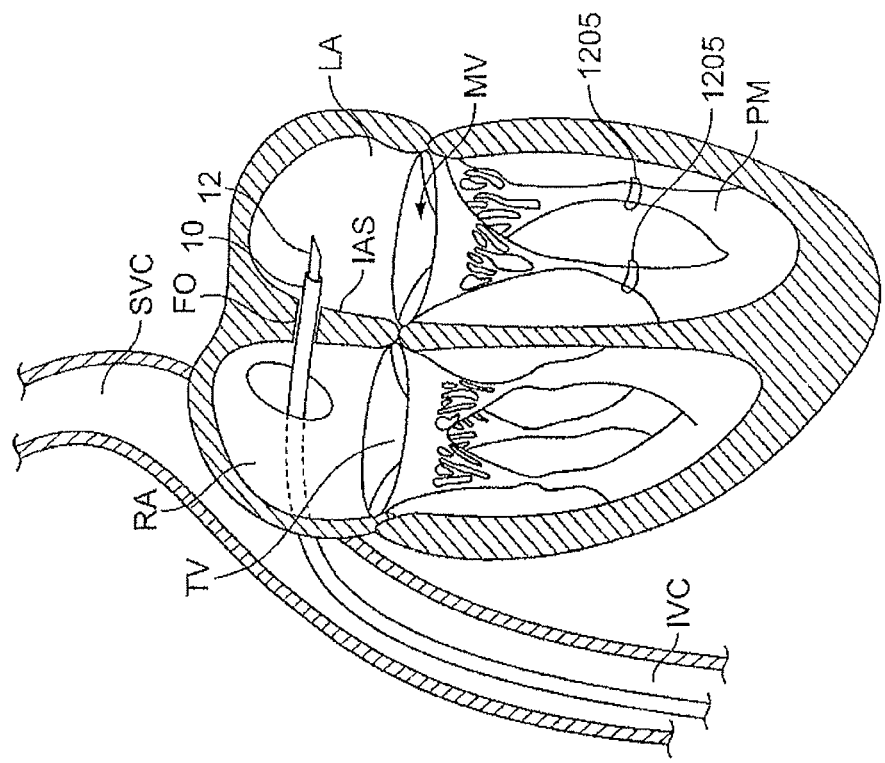
FIG. 16 shows a schematic view of a papillary muscle with a ring positioned over the muscle.

Other embodiments are directed to adjusting the length or orientation of papillary muscles. FIG. 16 shows a schematic view of the heart showing the papillary muscles PM. With reference to FIG. 16, a method of treating heart disease includes inserting an anchor, cuff or sleeve 1205 into the left ventricle of an individual's heart, and sliding a cuff or sleeve around a papillary muscle PM. The size of the cuff or sleeve is reduced so that the cuff or sleeve squeezes the papillary muscle. As the size of the cuff or sleeve is reduced, the papillary muscle stretches and increased in length.

In yet another embodiment, a method of treating heart disease includes obtaining access to a papillary muscle in a left ventricle of the heart. The papillary muscle is cut and reattached at a new location on an inner wall of the ventricle closer to the mitral valve.

Figure 17:
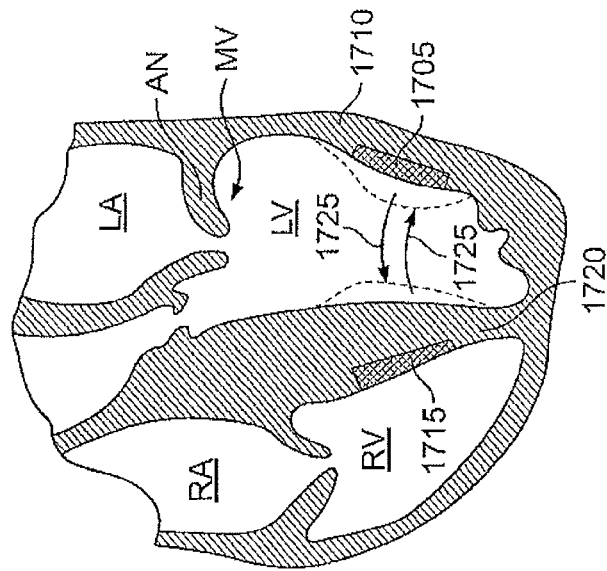
FIG. 17 shows a cross-sectional view of the heart with one or more magnets attached to a wall of the left ventricle.

Additional embodiments that employ magnets in the heart are now described with reference to FIGS. 17-19, which show cross-sectional views of the heart. With reference to FIG. 17, in one embodiment one or more magnets 1705 are implanted or otherwise attached to a wall 1710 of the left ventricle LV. One or more other magnets 1715 are implanted or otherwise attached to a wall 1720 of the right ventricle. The magnets 1705 and 1715 are attached to the walls 1710 and 1720 such that they assert an attractive magnetic force (as represented by the arrows 1725 in FIG. 17) toward each other. The magnetic force 1725 assists in remodeling of the left ventricle during pumping of the heart. That is, the magnets 1705 and 1715 are urged toward one another (thereby also urging the walls 1710 and 1720 toward one another) to re-shape either the annulus AN or the left ventricle LV. The annulus or the left ventricle LV are re-shaped in a manner that reduces or eliminates backflow through the mitral valve MV. It should be appreciated that a similar procedure can be performed on the right ventricle RV and associated valves.

Figure 18A:
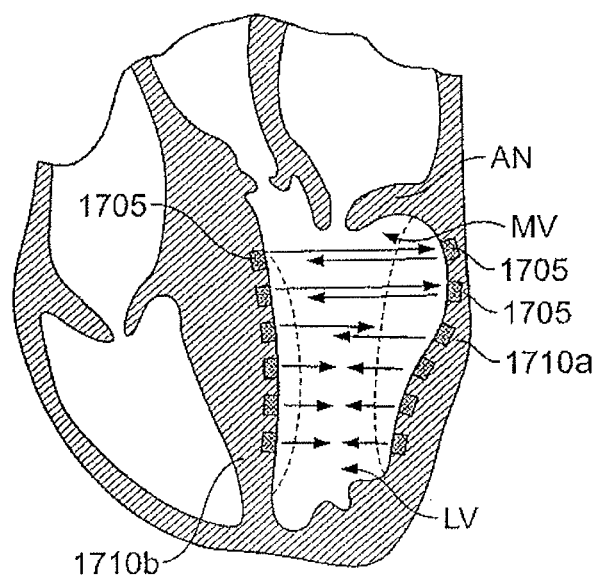
FIG. 18A shows another embodiment of a procedure wherein magnets are implanted in the heart to geometrically reshape the annulus or the left ventricle.

FIG. 18A shows another embodiment of a procedure wherein magnets are implanted in the heart to geometrically reshape the annulus or the left ventricle. One or more magnets 1705 are implanted or otherwise attached to a first wall 1710a of the left ventricle LV. One or more magnets 1705 are also implanted or otherwise attached to a second, opposed wall 1710b of the left ventricle. The magnets on the opposed walls 1710a, 1710b exert an attractive magnetic force toward one another to draw the walls 1710a, 1710b toward one another and re-shape the left ventricle LV or the annulus AN.

Another embodiment of a procedure uses magnets to anchor tethers within the heart at various locations to optimize the shape of cardiac structures to improve cardiac function. The tethers are placed to either reshape the cardiac structure or to prevent dilatation of the structure over time. The tethers must be securely anchored to the heart structures. A method of anchoring which enables tethering in various positions and directions within the cardiac structures is important for the clinician to optimize cardiac reshaping based on each individual patient anatomy and disease state. A method of anchoring which is atraumatic is also desirable.

Figure 18B:
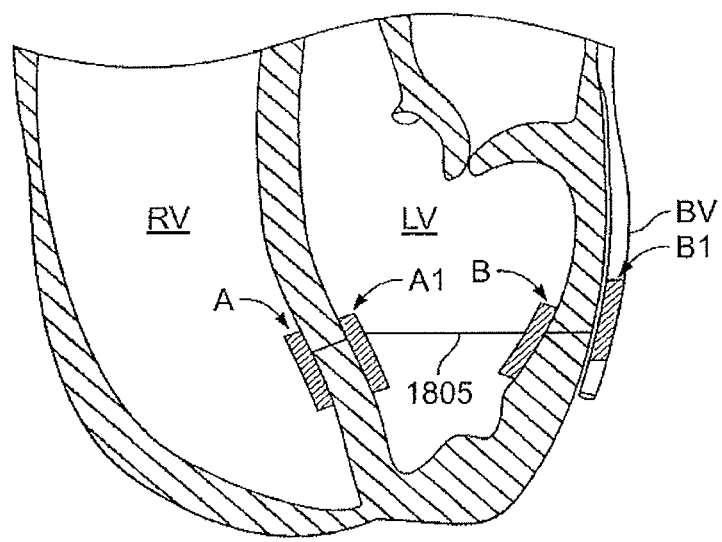
FIG. 18B shows the heart wherein tethered magnets are implanted in various locations to geometrically reshape the annulus or the left ventricle.

FIG. 18B shows a side view of the heart with sets of magnets A, A1, B, and B1 positioned to various locations of the heart or to anatomical structures adjacent the heart. In one embodiment, at least one magnet A is placed on the interventricular septum within the right ventricle RV. At least one magnet A1 is placed within the left ventricle LV opposite magnet A. The magnetic force between A and A1 maintains the position of the magnets. The magnets may be enclosed in materials that will promote tissue in-growth and healing to the interventricular septum to ensure stability of location and to eliminate the need for long term anticoagulation. Additionally, the enclosure material which is flexible and can be delivered in a low profile can be significantly larger in size than the magnets to increase the surface area of contact with the heart wall which will increase the tension that can ultimately be placed on the anchor over time.

A second set of magnets B and B1 are then delivered to another location selected within or adjacent to the heart. The set of magnets A/A1 are attached to the set of magnets B/B1 using at least one tether 1805, as shown in FIG. 18B. The tether 1805 can be attached to either or both of the magnets A/A1 at one end and to either of both of the magnets B/B1 at an opposite end. When the set of magnets B/B1 are tethered under tension to the set of magnets A/A1, a change in the shape of the cardiac structure results to improve cardiac function. FIG. 18B shows magnet B positioned in the LV and B1 positioned in a blood vessel BV adjacent to the heart. The magnetic force between B and B1 maintains the location of B and B1. Magnets B and B1 are delivered on or within materials and structures which promote healing and increase the amount of tension that can be placed on the anchor over time. For example, magnet B1 can be delivered on a stent which is of a length, diameter and material which will heal within the BV to provide sufficient resistance to forces placed on it by the tethers.

The tethers may be pre-attached to the magnets A and B1 or they may be attached after A and B1 have been positioned. The tether length may be shortened and/or adjusted after placement of the anchors. Alternatively the final tether length may be pre-selected based on the patient's cardiac structure geometry and the effect the clinician desires. Placing sets of magnets in this method, enables anchoring of tethers within the heart in various positions and angles which provides increased flexibility and variation for clinicians to select optimal re-shaping of the cardiac structures based on specific patient characteristics.

Examples which demonstrate the flexibility of this approach include placing anchors at the annulus and at the apex of the heart and tethered to shorten the length of the LV; anchors can be placed in the around the annulus and tethered to change the shape of the annulus. More specifically, one or more sets of magnets can be placed in the RA and LA at the level of the mitral valve annulus (on the anterior side of the annulus) and one or more sets of magnets can be placed in the LA and LV on opposite sides of the annulus on the posterior portion of the annulus. The posterior sets of magnets can then be tethered to the anterior sets of magnets to change the shape of the annulus. Alternatively, the magnet anchors can be placed at the level of the annulus in the LA and in a BV adjacent to the heart at the level of the annulus and these then tethered to the anterior annulus magnet anchor described above.

The magnets A and A1 can also be a single magnet that extends through the interventricular septum. Moreover, only one of the magnets A or A1 need be implanted. One or more magnets B and/or B2 are located opposite the location of the magnet(s) A and/or A1. The magnet(s) B is located within the left ventricle opposite the magnets A/A1, such as on the left ventricular wall. The magnet B1 is located on an anatomical structure adjacent the heart, such as on a blood vessel BV.

Figure 18C:
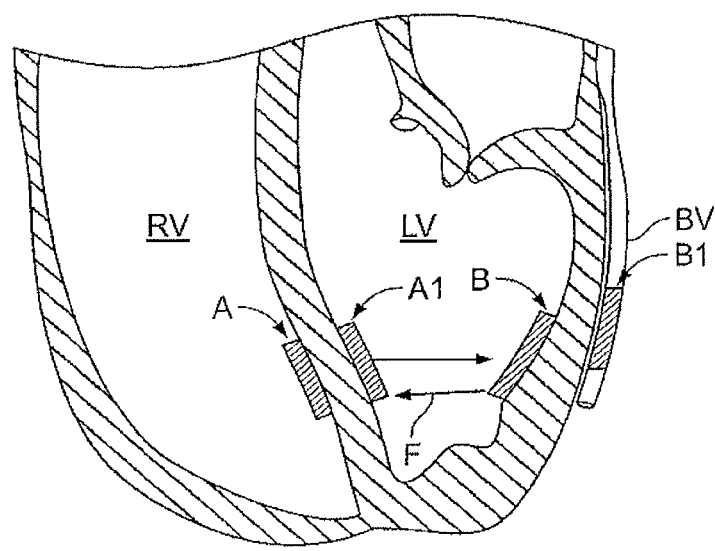
FIG. 18C shows the heart wherein magnets are implanted in various locations to geometrically reshape the annulus or the left ventricle.

In another embodiment shown in FIG. 18C, the magnets A, A1, B, and B1, or combinations thereof, are implanted in the heart without tethers. The magnets A, A1, B, and B1 can be positioned in various combinations so as to exert magnetic attractions to one another to re-shape the left ventricle or the mitral valve annulus. For example, the magnets A and B can be implanted such that they exert an attractive magnetic force relative to one another. The magnets A and B2 can alternately be implanted. Other possible combinations are the magnets A1 and B or the magnets A1 and B2. The magnets can be implanted without tethers such that an attractive magnetic force F causes the magnets and the attached region of the heart to move toward one another to re-shape the heart. Alternately, the magnets can be attached to one another with tethers.

Figure 19:
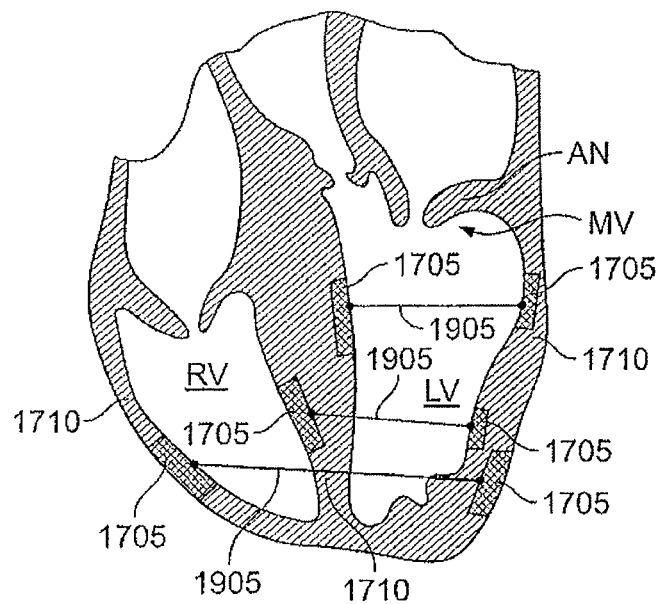
FIG. 19 shows another embodiment of a procedure wherein magnets are implanted in the heart to geometrically reshape the annulus or the left ventricle.

In yet another embodiment, one or more magnets 1705 are implanted in the walls 1710 of the left ventricle LV and/or the right ventricle RV, as shown in FIG. 19. The magnets 1705 are positioned in opposed locations on the walls 1710 and one or more tethers 1905 attach opposed pairs of magnets 1705 to one another. One or more of the tethers 1905 extend through the interventricular septum to connect a first magnet disposed in the left ventricle and a second magnet disposed in the right ventricle. In certain embodiments, magnet elements do not include tethers, but rely on the magnetic attraction to each other to remodel the tissue between them. For example, a magnetic element may be placed on either side of the interventricular septum, or one element within the septum. Another magnetic element may be placed on or within the opposite left ventricular wall, or in an adjacent vessel on the left ventricular wall. The electromagnetic field of such elements can then interact to cause a remodeling of the left ventricle to assist with ventricular function.

The tethers 1905 can be elastic so to exert an attractive force between the attached magnets 1705 and re-shape the left ventricle LV or annulus AN. Alternately, or in combination with elastic tethers, the tethers 1905 can be shortened in length after placement to thereby pull the walls of the left ventricle LV toward one another and re-shape the left ventricle LV or the annulus AN. In combination with the force provided by the tethers 1905, the magnets 1705 exert an attractive magnetic force toward one another to assist in pulling the heart walls toward each other.

It should be appreciated that one or more magnets can be positioned in other locations of the heart or adjacent anatomical structures for re-shaping of the heart. For example, one or more magnets can be positioned around the annulus AN or can be positioned in the coronary sinus in such a manner that the magnets exert attractive forces toward one another to cause re-shaping of a desired portion of the heart.

In another embodiment, cardiac re-shaping is achieved through percutaneous placement of one or more tethers that are cinched or anchored in the walls of the left ventricle LV. The tethers provide tension between the walls of the left ventricle to reshape the left ventricle LV in a desired manner. FIG. 20 shows a cross-sectional view of the left ventricle LV with a tether 2010 positioned therein. The tether 2010 has a first end anchored to a first wall of the left ventricle LV and a second end anchored to an opposed wall of the left ventricle LV. The tether 2010 is tensioned to pull the walls toward one another (as represented by the phantom lines 2012 in FIG. 20) and re-shape the left ventricle LV. It should be appreciated that the phantom lines 2012 in FIG. 20 are merely representative of the geometric re-shaping. The left ventricle LV can be re-shaped in various manners and the amount of re-shaping can vary depending on the tension applied to the tether 2010 and the location of attachment to the walls of the left ventricle LV. The tether may be inelastic or somewhat elastic.

The tether 2010 can be anchored or otherwise attached to the walls in various manners. In an exemplary embodiment, a patch 2015 (shown in FIG. 20) of material is positioned on an exterior surface of the ventricular wall and is attached to one end of the tether 2010. A similar patch can also be positioned on the opposed wall and attached to the opposite end of the tether.

With reference to FIG. 21, the patch is delivered to a desired location using a catheter 2105 having a sharpened distal end 2110 that is positioned within the left ventricle LV. The catheter 2105 can be delivered to the left ventricle LV in various manners, including trans-aortically (via the aorta), trans-septally (by piercing the interventricular septum), and trans-atrially (via the left atrium LA) pursuant to well-known methods. As shown in FIG. 22, the sharpened distal end 2110 pierces the ventricular wall such that the distal end 2110 is positioned exterior to the ventricular wall. The catheter 2105 has an internal delivery lumen having an opening at the distal end 2110. The patch 2015 is configured to be transported in a contracted state through the delivery lumen and delivered out of the opening at the distal end 2110, where the patch 2015 expands into an expanded state at the exterior of the ventricular wall to seal against the exterior of the left ventricular wall.

When positioned at the exterior of the ventricular wall, the patch 2015 is configured to act as a reservoir that receives a fluid material that can be delivered to the patch via the delivery lumen of the catheter 2105. The fluid material has a first viscous state of sufficient fluidity such that the material can flow through the delivery lumen of the catheter 2105 and out of the distal end 2110 to the location of the patch 2015. The fluid material changes to a second viscous state when positioned exterior to the ventricular wall at the patch 2015. The second viscous state is of greater viscosity (i.e., more resistant to flow) than the first viscous state such that the fluid material provides support and a level of rigidity to the patch 2015 and to the left ventricular wall. The fluid material can change to the second viscous state after a predetermined time period, after contact with the patch, or when the patch is completely filled. A catalyst can be injected into the fluid material to cause it to change to the second viscous state.

As shown in FIG. 23, the catheter 2105 can then be disengaged from the patch 2015 such that the patch 2015 is disposed exterior to the ventricular wall. The patch 2015 can be firmly attached to the ventricular wall (such as using an adhesive) to minimize wear or friction between the patch and the ventricular wall. Next, an end of the tether 2010 is attached to the patch 2015. The catheter 2105 can be used to deliver the tether 2010 to the patch 2015 or, alternately, a second catheter can be used. In one embodiment, the tether 2010 is already positioned in a delivery lumen of the catheter 2105 while the patch 2015 is being delivered. The catheter 2105 is then pulled back while the end of the tether 2010 remains attached to the patch 2015 to thereby let the tether 2010 out from the catheter 2105, as shown in FIG. 23.

Figures 24, 25:
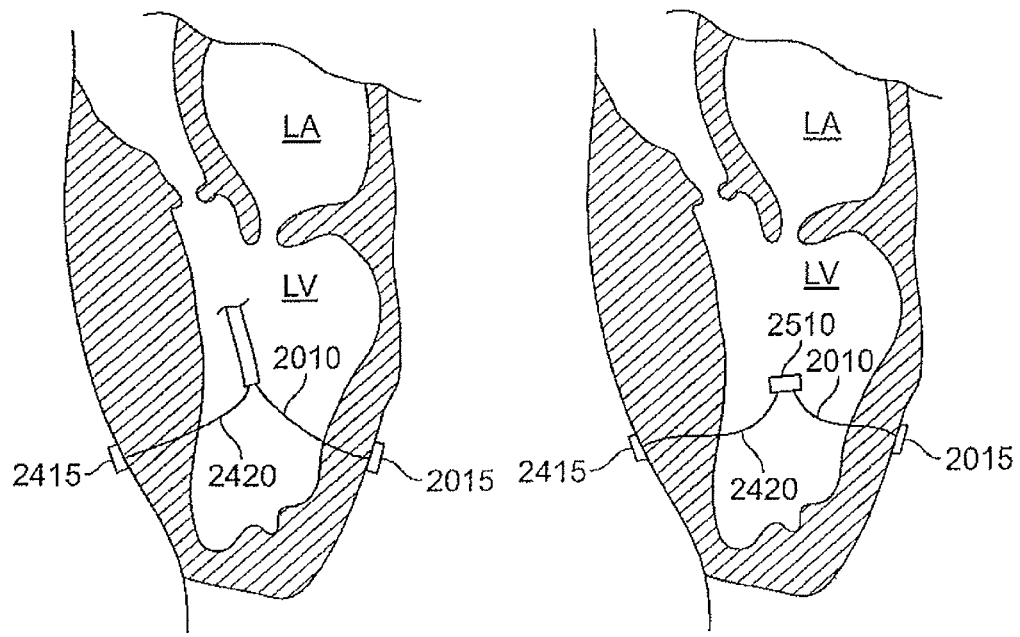
FIG. 24 shows a cross-sectional view of the left ventricle with the delivery penetrating delivering a second patch.
FIG. 25 shows a cross-sectional view of the left ventricle with two tethers attached together at opposite ends from the patches mounted in the heart.

With reference now to FIG. 24, a second patch 2415 is deployed in or exterior to an opposed ventricular wall in a manner similar to that described above. The opposite end of the tether 2010 is then attached to the second patch 2415 such that the tether 2010 extends between the two patches, as shown in FIG. 20. Alternately, as shown in FIG. 24, a second tether 2420 is attached at a first end to the second patch 2415. As shown in FIG. 25, the two tethers 2010 and 2420 can then be attached together at opposite ends from the patches, such as by using a clip 2510, to form a single attachment tether between the patches 2015 and 2415. The tethers 2010 and 2420 can be twisted or adjusted within the clip 2510 to tension the resulting attachment tether between the patches 2415 and 2015 and pull the ventricular walls toward one another via the tether. Once properly tensioned, the tether can be clipped or clamped to maintain its position.

Figures 26, 27:
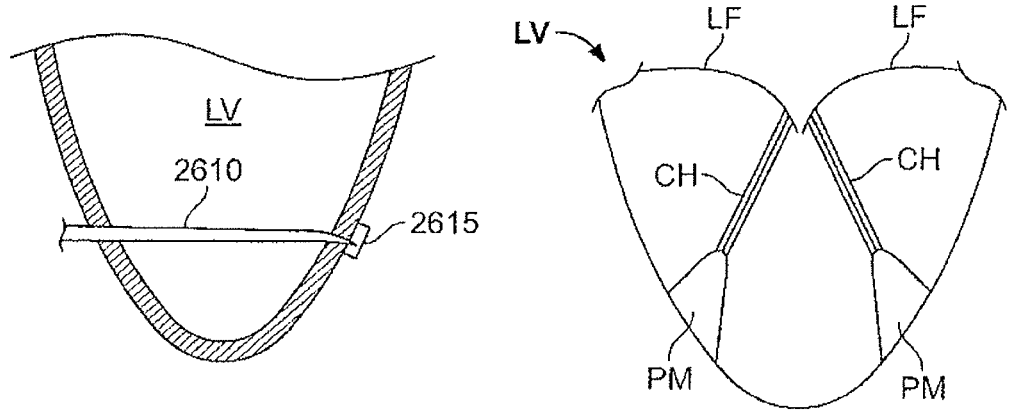
FIG. 26 shows a cross-sectional view of the left ventricle with a needle or delivery catheter passed transthoracically into the left ventricle LV to deliver a patch to the exterior of the ventricular wall.
FIG. 27 shows a schematic, cross-sectional view of the left ventricle in a healthy state with the mitral valve closed.

In another embodiment, shown in FIG. 26, a needle 2610 or delivery catheter is passed trans-thoracically into the left ventricle LV to deliver a patch 2615 to the exterior of the ventricular wall, as described above. A sealing means, such as a sealing balloon, can be used to seal one or more puncture holes in the wall of the left ventricle caused by the needle 2610 during delivery of the patch 2615. Visualization means, such as fluoroscopy, can be used to visualize proper placement of the needle 2610. A second patch is attached to an opposed wall to form a tether attachment between the walls, as shown in FIG. 20. The tether is then tensioned to pull the walls together and re-shape the left ventricle or annulus of the mitral valve in a desired manner.

In other embodiments, described with reference to FIGS. 27-31, cardiac re-shaping is achieved by manipulation of the papillary muscles. FIG. 27 shows a schematic, cross-sectional view of the left ventricle LV in a healthy state with the mitral valve closed. The valve chordae CH connect the leaflets LF of the mitral valve to the papillary muscles PM. The papillary muscles PM and the and chordae CH are positioned such that at least a portion of the leaflets LF contact one another when the mitral valve is in the closed state, resulting in functional coaptation of the leaflets.

Figures 28, 29:
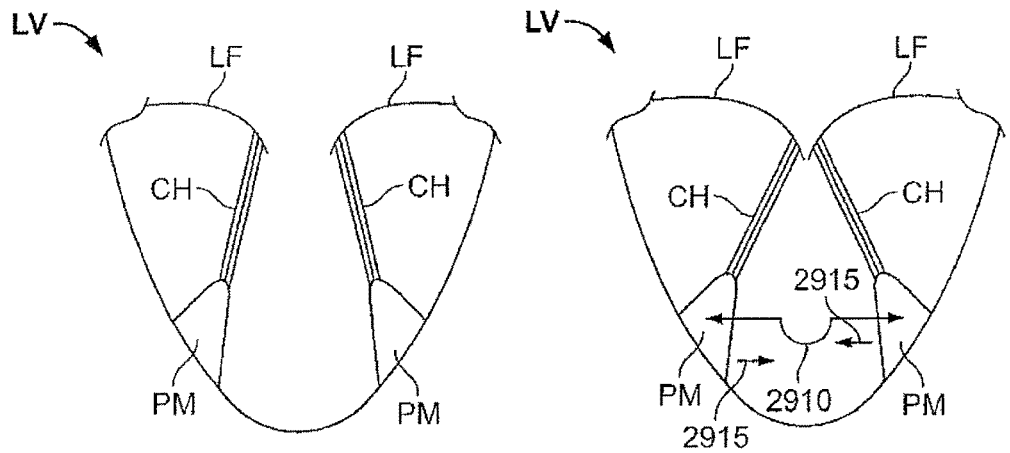
FIG. 28 shows the left ventricle in a dysfunctional state.
FIG. 29 shows the left ventricle with a biasing member mounted between the papillary muscles.

FIG. 28 shows the left ventricle LV in a dysfunctional state. The valve chordae CH or the papillary muscles PM are damaged or otherwise dysfunctional such that the leaflets LF do not properly coapt (contact one another). The dysfunction can be manifested by excess tension in the chordae CH such that a gap is located between the leaflets LF, or in some cases one leaflet may function at a different level from the other (e.g. lower (prolapse) or higher (flail)) thereby limiting the ability of the mitral valve to close resulting in mitral regurgitation. The dysfunctional left ventricle LV and in some cases leaflet prolapse or flail, can be treated by manipulating papillary muscles PM to adjust the position of the leaflets LF. In one embodiment, the papillary muscles PM are repositioned toward one another to reduce the distance between the papillary muscles PM.

In an embodiment described with reference to FIG. 29, a biasing member, such as a rod of adjustable length, or a spring 2910, is mounted between the papillary muscles PM with a first end of the spring 2910 attached to a first papillary muscle and a second end of the spring 2910 attached to a second papillary muscle. The spring 2910 has a pre-load such that the spring 2910 provides a biasing force (represented by the arrows 2915 in FIG. 29) that pulls the papillary muscles PM toward one another. Such a spring may be covered with polyester fabric or other coating to promote ingrowth into the muscle tissue and minimize the potential for clot formation. The repositioning of the papillary muscles PM re-shapes the left ventricle and/or changes the distance that the leaflets need to move on the chordae CH such that the leaflets LF contact one another to close the mitral valve. The tension provided by the spring 2910 can be varied or different springs can be used to achieve a proper repositioning of the papillary muscles PM. The tension may be modified at the time of the procedure or during a subsequent procedure if it is determined that additional coaptation is required.

In another embodiment, described with reference to FIG. 30, a suture 3010 is mounted between the papillary muscles PM with a first end of the suture 3010 attached to a first papillary muscle and a second end of the suture 3010 attached to a second papillary muscle. The suture 3010 can be attached to the papillary muscles in various manners. For example, an attachment device 3015, such as an anchor, cuff or sleeve, can be positioned around or partially around each of the papillary muscles. The ends of the suture 3010 are attached to the attachment devices 3015 to secure the suture 3010 to the suture to the papillary muscles.

The suture 3010 is tensioned such that it provides a force that pulls the papillary muscles PM toward one another. The suture 3010 can be tensioned, for example, by twisting the suture 3010 to reduce its the overall length and thereby reduce the distance between the papillary muscles PM, and fixing the suture with a crimping element or other stay element. The amount of twisting or shortening can be varied to vary the tension provided by the suture 3010. In addition, a crimping member may be used to fix the sutures once a desired tension between the muscles is reached. Exemplary crimping members are described in International Patent Publication Number WO 2003/073913, which is incorporated herein by reference in its entirety. As in the previous embodiment, the repositioning of the papillary muscles PM re-shapes the left ventricle and/or changes the tension on the chordae CH such that the leaflets LF contact one another to close the mitral valve. Cuffs or sleeves may be placed around the papillary muscles PM to such as those previously described, to affect the repositioning.

Figures 30, 31:
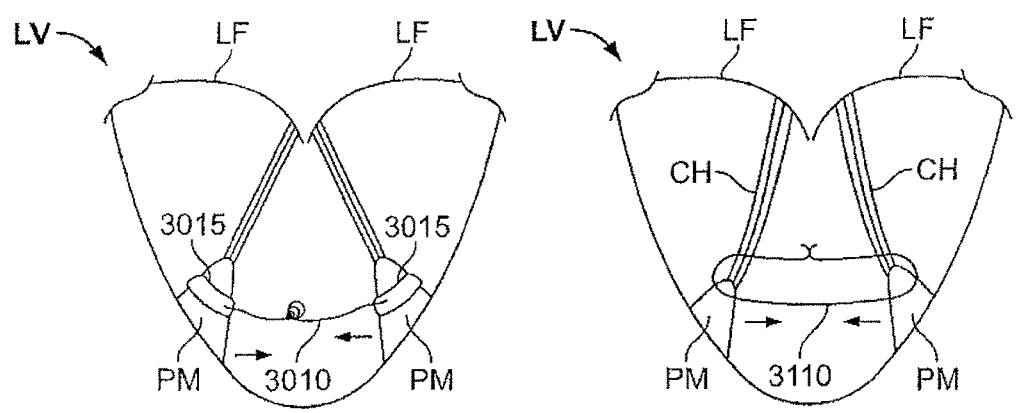
FIG. 30 shows the left ventricle with a suture mounted between the papillary muscles.
FIG. 31 shows the left ventricle with a snare positioned around the chordae at or near the location where the chordae attach with the papillary muscles.

With reference now to FIG. 31, the papillary muscles PM can also be repositioned by snaring the papillary muscles. A snare 3110 comprised of a looped strand of material is positioned around the chordae CH at or near the location where the chordae attach with the papillary muscles PM. The snare 3110 is tightened to draw the papillary muscles PM toward one another and re-shape the left ventricle and/or changes the distance that the leaflets need to travel during systole such that the leaflets LF contact one another to close the mitral valve.

Figure 36:
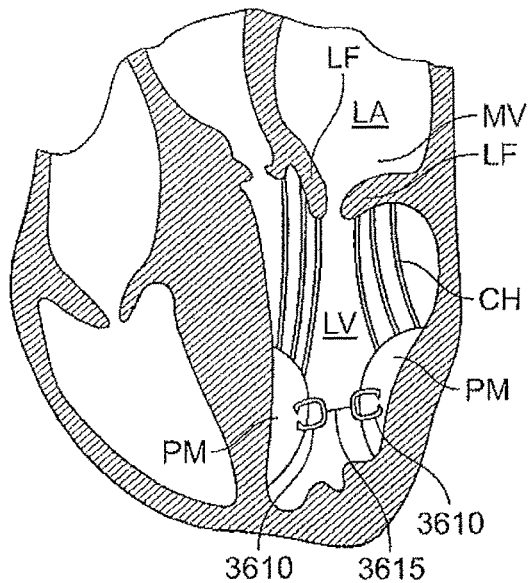
FIG. 36 shows a cross-sectional view of the heart with one or more clips clipped to each of the papillary muscles.

In yet another embodiment, shown in FIG. 36, one or more clips 3610 are clipped to each of the papillary muscles PM. The structure of the clips 3610 can vary. A tether 3615 attaches the clips 3610 to one another. The tether 3615 is cinched to shorten the length of the tether 3615 and pull the papillary muscles PM toward one another and re-shape the left ventricle and/or changes the distance that the leaflets need to travel during systole such that the leaflets LF contact one another to close the mitral valve.

Figure 37:
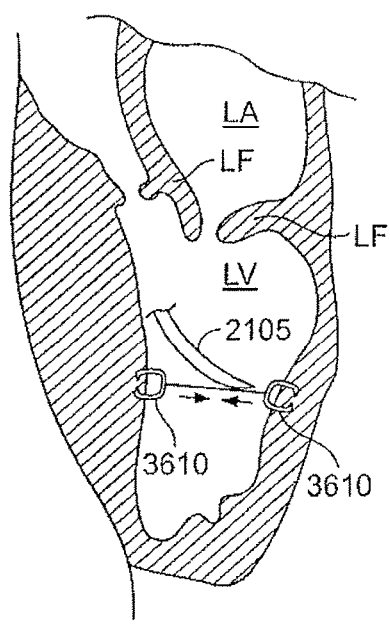
FIG. 37 shows a cross-sectional view of the heart with tethered clips attached to opposed walls of the left ventricle.

In yet another embodiment, shown in FIG. 37, one or more clips 3610 are clipped to opposed walls of the left ventricle LV. The clips 3610 can be delivered to the left ventricle using a delivery catheter 2105. A tether attaches the clips to one another. The tether is cinched to shorten the length of the tether and pull the ventricular walls toward one another and re-shape the left ventricle and/or changes the distance that the leaflets need to travel during systole such that the leaflets LF contact one another to close the mitral valve.

In all embodiments, once the papillary muscles are fixed or repositioned, it may be advantageous to further treat the area by selectively elongating or shortening the chordae tendinae to achieve further optimal valve function. In addition, a mitral valve clip may be deployed to augment the desired valve function, either before papillary or chordal manipulation, or after, if the desired leaflet coaptation is not achieved with one particular approach.

As discussed above with reference to FIG. 28, a dysfunctional left ventricle can be manifested by excess tension in the chordae CH such that a gap is positioned between the valve leaflets LF. It can be desirable to eliminate or relieve the excess tension by cutting the chordae CH, and/or cutting the chordae and replacing them with artificial chordae. Prior to cutting the chordae, it can be desirable to evaluate the placement of the artificial chordae to confirm that implantation of the chordae will indeed provide the desired clinical result. This process is now described with reference to FIGS. 32-35.

Figure 32:
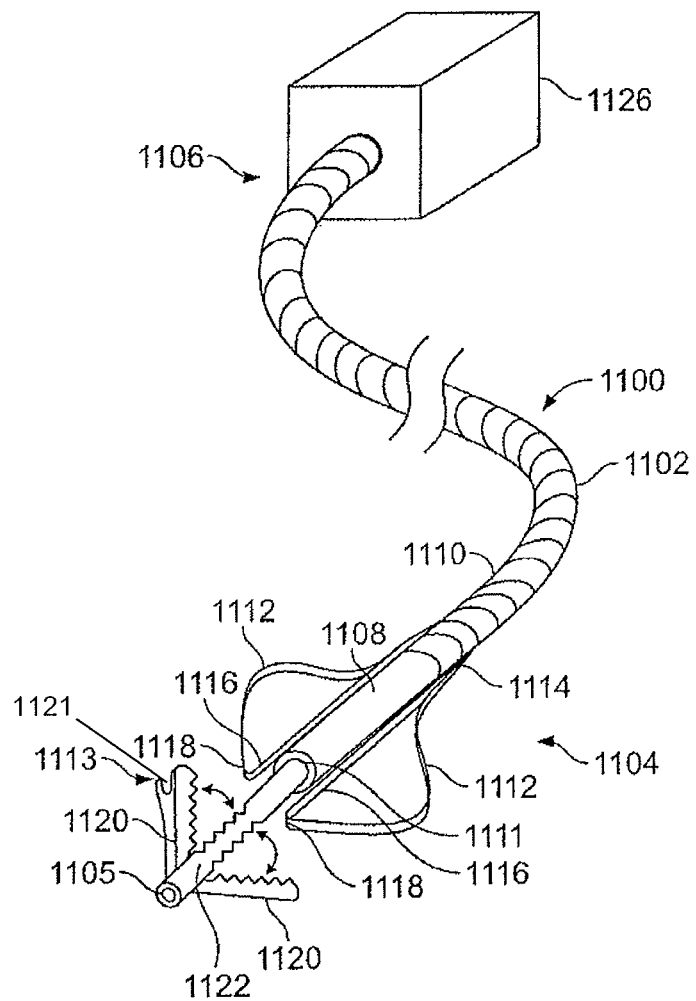
FIG. 32 shows a leaflet grasping device that is configured to grasp and secure the leaflets of the mitral valve.

FIG. 32 shows a leaflet grasping device 1100 that is configured to grasp and secure the leaflets of the mitral valve. The device 1100 and corresponding methods of use are described in more detail in U.S. Patent Publication No. 2004/0030382, entitled "Methods and Apparatus For Cardiac Valve Repair", which is incorporated herein by reference in its entirety. Additional leaflet grasping devices are described in U.S. Patent Publication No. 2004/0092962, U.S. Pat. No. 6,269,819, issued Aug. 7, 2001, and U.S. Pat. No. 6,461,366, issued Oct. 8, 2002, all of which are expressly incorporated by reference herein.

Referring to FIG. 32, the device 1100 is comprised of a catheter shaft 1102 having a distal end 1104 and a proximal end 1106. The catheter shaft 1102 is comprised of, among others, a conduit 1108, a coaxial outer sheath 1110, a central lumen 1111 through which a double-jaw grasper 1113 may be inserted, and a central guidewire lumen 1105. The catheter shaft 1102 can have additional lumens for the passage of one or more needles, as described more fully below.

Toward the distal end 1104, an optional pair of stabilizers 1112 are fixedly mounted on the outer sheath 1110 at their proximal end 1114 and fixedly attached to extenders 1116 at their distal end 1118. The stabilizers 1112 are shown in an outwardly bowed position, however they may be inwardly collapsed by either extending the extenders 1116 or retracting the outer sheath 1110. Bowing may be achieved by the reverse process.

The double-jaw grasper 1113 is comprised of two articulating jaw arms 1120 which may be opened and closed against the central shaft 1122 (movement depicted by arrows) either independently or in tandem. The grasper 1113 is shown in the open position in FIG. 32. The surfaces of the jaw arms 1120 and central shaft 1122 may be toothed, as shown, or may have differing surface textures for varying degrees of friction. The jaw arms 1120 each include a needle passageway 1121 comprised of a cutout or a slot that extends at least partially along the length of each jaw arm 1120. As described in more detail below, the needle passageway provides a location where a needle can pass through the jaw arm 1120 during manipulation of the papillary muscle.

The above described components may be manipulated and controlled by a handle 1126 connected to the proximal end 1106 of the catheter shaft 1102, as shown in FIG. 32 the handle 1026 permits independent control of the components described above.

Figure 33A:
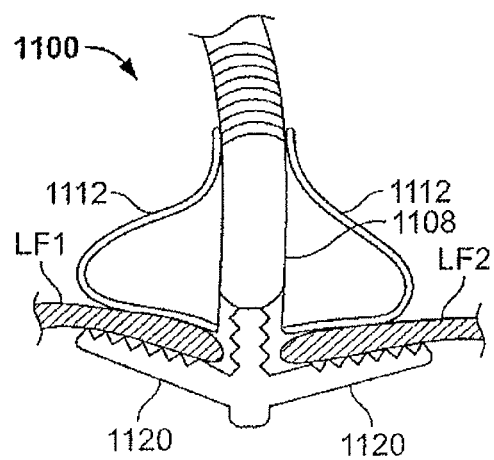
FIGS. 33A-33C show the leaflet grasping device grasping leaflets of the mitral valve.
Figure 33B:
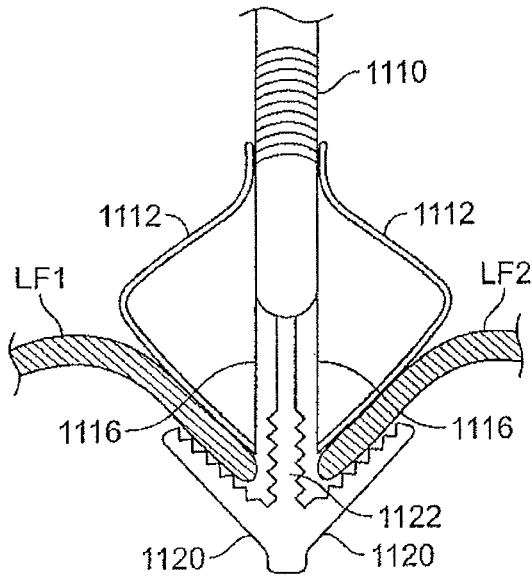
Figure 33C:
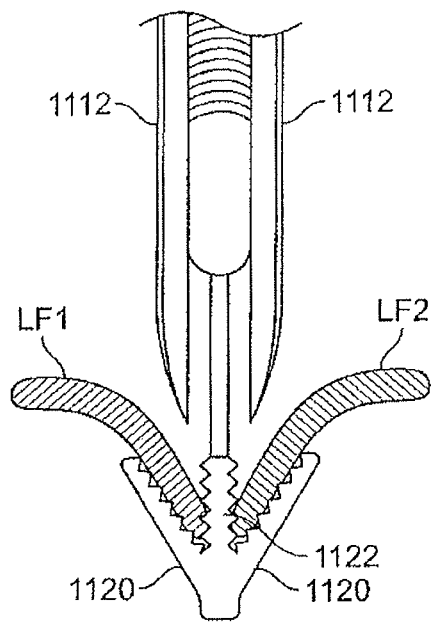

Referring to FIGS. 33A-C, the device 1100 may be used at least temporarily grasp and restrain the valve leaflets LF of the mitral valve MV. The double-jaw grasper 1113 extends through the valve such that the leaflets LF1, LF2 are grasped from below. Thus, the device 1100 is termed "atrial-ventricular."

Referring to FIG. 33A, the atrial device 1100 may be stabilized against the mitral valve MV. The stabilizers 1112 may be positioned on the superior surface of the valve leaflets LF1, LF2 at a 90 degree angle to the line of coaptation. The grasper 1113 may be advanced in its closed position from the conduit 1108 between the leaflets LF1, LF2 until the jaw arms 1120 are fully below the leaflets in the ventricle. At this point, the grasper 1113 may be opened and retracted so that the jaw arms 1120 engage the inferior surface of the leaflets LF1, LF2. In this manner, the leaflets are secured between the stabilizers 1112 and the jaw arms 1120.

Referring to FIG. 33B, the grasper 1113 will gradually close, drawing the leaflets LF1, LF2 together while maintaining a secure hold on the leaflets between the jaw arms 1120 and the stabilizers 1112. This may be accomplished by number of methods. For example, the stabilizers 1112 may be gradually collapsed by either extending the extenders 1116 or retracting the outer sheath 1110. As the stabilizers 1112 collapse, the jaw arms 1120 may collapse due to spring loading to gradually close the grasper 1113. Alternatively, the jaw arms 1120 may be actuated to close against the central shaft 1122 applying force to the stabilizers 1112 causing them to collapse. In either case, such action allows the stabilizers 1112 to simultaneously vertically retract and withdraw from the leaflets as the leaflets are clamped between the jaw arms 1120 and the central shaft 1122. In this manner, the leaflets are effectively "transferred" to the grasper 1113. Referring to FIG. 33C, once the collapsed stabilizers 1112 are completely withdrawn, the leaflets LF1, LF2 are held in vertical opposition by the grasper 1113 in a more natural coaptation geometry.

Figure 34:
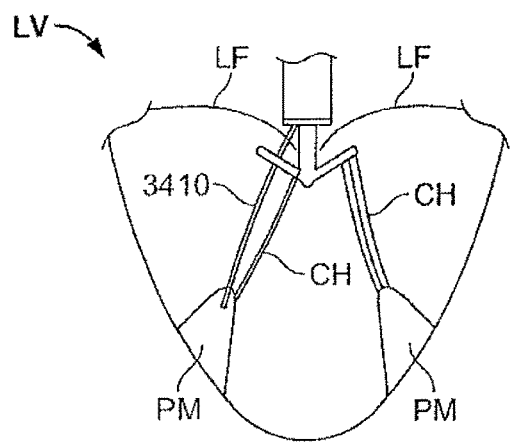
FIG. 34 shows the left ventricle with a needle being advanced from the left atrium into the left ventricle via the leaflet grasping device.

With reference now to FIG. 34, a needle 3410 is advanced from the left atrium into the left ventricle. The needle 3410 can be passed through a lumen in the device 1100 or it can be passed external to the device 1100. In any event, the needle 3410 passes through a leaflet LF and into a papillary muscle PM. As mentioned, the jaw arms 1120 have needle passageways 1121 (shown in FIG. 32) that permit passage of the needle through the jaw arms 1120.

The needle 3410 is attached to a suture 3415 that extends distally through the device 1100. The suture 3415 is then anchored to the papillary muscle PM such that the suture 3415 provides an attachment for holding, pulling, or otherwise manipulating the papillary muscle PM. The tension in the suture 3415 can be adjusted to re-position the papillary muscle PM such that the leaflets LF contact one another to close the mitral valve. The same process can be performed with the other papillary muscle.

Figure 35:
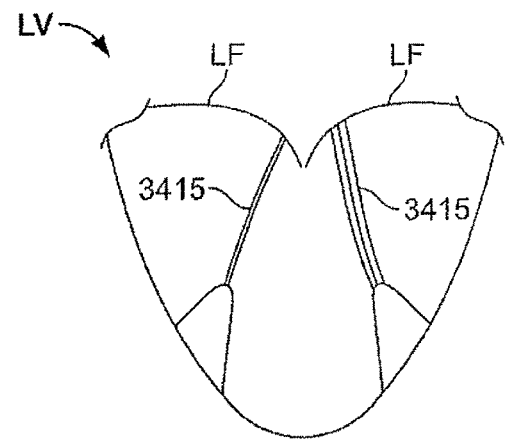
FIG. 35 shows the left ventricle with sutures holding the papillary muscles in a desired position.

With the sutures 3415 holding the papillary muscles PM in a desired position, as shown in FIG. 35, the chordae CH may be cut. The sutures 3415 function as artificial chordae that retain the leaflets LF and papillary muscles PM in a desired orientation.

A fixation device such as a clip can then be attached to the leaflets using methods and device described in U.S. Patent Publication Nos. 2004/0030382, filed Aug. 5, 2003, and 2004/0092962, filed May 19, 2003, U.S. Pat. No. 6,269,819, issued Aug. 7, 2001, and U.S. Pat. No. 6,461,366, issued Oct. 8, 2002, all of which are expressly incorporated by reference herein. The sutures 3415 can be attached to the clip 3510 or directly to the leaflets LF. It should be appreciated that any quantity of sutures 3415 can be used as artificial chordae between the leaflets and the papillary muscles. It should be appreciated that the leaflet clips can also be used in conjunction with cutting, elongating, or shortening of the chordae pursuant to the methods described above.

Prior to permanently placing the chordae or clips, the result can be previewed on ultrasound (TEE, ICE, echocardiography), to determine if the appropriate valve coaptation is restored. In addition, it is within the scope of the present invention to implant a mitral valve clip in addition to performed papillary muscle approximation or chordal implantation.

As will be apparent to those of skill in the art upon reading this disclosure, each of the individual embodiments described and illustrated herein has discrete components and features which may be readily separated from or combined with the features of any of the other several embodiments without departing from the scope of the subject matter described herein. Any recited method can be carried out in the order of events recited or in any other order which is logically possible.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. A method of attaching a chordal replacement device, the method comprising:
   advancing a proximal anchor into a heart;
   attaching a flexible patch of the proximal anchor to the heart;
   attaching a leaflet attachment device of the proximal anchor to an upper surface of a portion of a leaflet;
   advancing a distal anchor of the chordal replacement device into a ventricle of the heart, the distal anchor including a balloon;
   positioning the balloon at least partially into a sidewall of the ventricle; and
   filling the balloon with fluid to increase tension on a flexible tether, which is coupled to and tensioned between the proximal and distal anchors,
   wherein the filled balloon of the distal anchor remains at least partially within the sidewall of the ventricle.

2. The method of claim 1, wherein the proximal anchor further comprises a mesh stent deployable within an atrium.

3. The method of claim 2, wherein the mesh stent is coupled to a flexible rod that is configured to extend through a valve commissure and into the ventricle.

4. The method of claim 3, wherein a distal end of the flexible rod couples to the distal anchor and is configured to provide consistent tension on the tether during a heart cycle.

5. The method of claim 3, wherein the flexible rod has a deflectable, spring-formed shape.

6. The method of claim 3, wherein the flexible rod is jointed.

* * * * *